US010716510B2

(12) United States Patent
Connor

(10) Patent No.: US 10,716,510 B2
(45) Date of Patent: Jul. 21, 2020

(54) SMART CLOTHING WITH CONVERGING/DIVERGING BEND OR STRETCH SENSORS FOR MEASURING BODY MOTION OR CONFIGURATION

(71) Applicant: Robert A. Connor, Burnsville, MN (US)

(72) Inventor: Robert A. Connor, Burnsville, MN (US)

(73) Assignee: Medibotics, St. Paul, MN (US)

( * ) Notice: Subject to any disclaimer, the term of this patent is extended or adjusted under 35 U.S.C. 154(b) by 478 days.

(21) Appl. No.: 15/702,081

(22) Filed: Sep. 12, 2017

(65) Prior Publication Data

US 2018/0008196 A1    Jan. 11, 2018

Related U.S. Application Data

(63) Continuation-in-part of application No. 14/795,373, filed on Jul. 9, 2015, now abandoned, which is a continuation-in-part of application No. 14/736,652, filed on Jun. 11, 2015, now abandoned, which is a continuation-in-part of application No. 14/664,832, filed on Mar. 21, 2015, now Pat. No. 9,582,072, application No. 15/702,081, which is a continuation-in-part of application No. 15/227,254, filed on Aug. 3, 2016, now Pat. No. 10,321,873, which is a continuation-in-part of application No.
(Continued)

(51) Int. Cl.
*A61B 5/00* (2006.01)
*A61B 5/0488* (2006.01)
*A61B 5/11* (2006.01)
*G06F 3/01* (2006.01)

(52) U.S. Cl.
CPC .......... *A61B 5/6804* (2013.01); *A61B 5/0488* (2013.01); *A61B 5/112* (2013.01); *A61B 5/1114* (2013.01); *A61B 5/1116* (2013.01); *A61B 5/1126* (2013.01); *A61B 5/4528* (2013.01); *A61B 5/6828* (2013.01); *G06F 3/011* (2013.01)

(58) Field of Classification Search
CPC ... A61B 5/6804; A61B 5/1114; A61B 5/6828; A61B 5/4528; A61B 5/1116; A61B 5/1126; A61B 5/112; A61B 5/0488; G06F 3/011
See application file for complete search history.

(56) References Cited

U.S. PATENT DOCUMENTS 3,974,491 A    8/1976    Sipe
4,542,291 A    9/1985    Zimmerman
(Continued)

OTHER PUBLICATIONS

"Embedded 3D Printing of Strain Sensors within Highly Stretchable Elastomers", by Muth et al., see attached publication. (Year: 2014).*

*Primary Examiner* — Xin Y Zhong

(57) ABSTRACT

This invention is smart clothing with stretch and/or bend sensors for measuring changes in a person's body configuration. This smart clothing has an elastic nonconductive layer onto which helical converging/diverging conductive pathways are printed using ink which is a mixture of elastic nonconductive material and conductive material. Changes in the transmission of electromagnetic energy through the pathway are analyzed to measure changes in the configuration of the person's body.

20 Claims, 10 Drawing Sheets

Related U.S. Application Data

14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/227,254 is a continuation-in-part of application No. 15/079,447, filed on Mar. 24, 2016, now Pat. No. 10,234,934, which is a continuation-in-part of application No. 14/463,741, filed on Aug. 20, 2014, now Pat. No. 9,588,582, said application No. 15/079,447 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/227,254 is a continuation-in-part of application No. 15/130,995, filed on Apr. 17, 2016, now Pat. No. 9,891,718, said application No. 15/227,254 is a continuation-in-part of application No. 14/736,652, filed on Jun. 11, 2015, now abandoned, which is a continuation-in-part of application No. 14/664,832, filed on Mar. 21, 2015, now Pat. No. 9,582,072.

(60) Provisional application No. 62/014,747, filed on Jun. 20, 2014, provisional application No. 62/100,217, filed on Jan. 6, 2015, provisional application No. 62/065,032, filed on Oct. 17, 2014, provisional application No. 62/086,053, filed on Dec. 1, 2014, provisional application No. 62/182,473, filed on Jun. 20, 2015, provisional application No. 62/187,906, filed on Jul. 2, 2015, provisional application No. 61/878,893, filed on Sep. 17, 2013, provisional application No. 61/976,650, filed on Apr. 8, 2014, provisional application No. 62/150,886, filed on Apr. 22, 2015, provisional application No. 62/357,957, filed on Jul. 2, 2016, provisional application No. 62/449,735, filed on Jan. 24, 2017, provisional application No. 62/538,793, filed on Jul. 30, 2017.

(56) References Cited

U.S. PATENT DOCUMENTS

| | | |
|---|---|---|
| 5,012,819 A | 5/1991 | Marras et al. |
| 5,086,785 A | 2/1992 | Gentile et al. |
| 5,184,009 A | 2/1993 | Wright et al. |
| 5,184,319 A | 2/1993 | Kramer |
| 5,280,265 A | 1/1994 | Kramer et al. |
| 5,316,017 A | 5/1994 | Edwards et al. |
| 5,337,758 A | 8/1994 | Moore et al. |
| 5,375,610 A | 12/1994 | LaCourse et al. |
| 5,442,729 A | 8/1995 | Kramer et al. |
| 5,474,088 A | 12/1995 | Zaharkin et al. |
| 5,516,249 A | 5/1996 | Brimhall |
| 5,533,531 A | 7/1996 | Edwards et al. |
| 5,592,401 A | 1/1997 | Kramer |
| 5,615,132 A | 3/1997 | Horton et al. |
| 5,640,971 A | 6/1997 | Martin, Jr. |
| 5,656,904 A | 8/1997 | Lander |
| 5,676,157 A * | 10/1997 | Kramer .................. A61B 5/103 600/595 |
| 5,694,497 A | 12/1997 | Sansone |
| 5,813,406 A | 9/1998 | Kramer et al. |
| 5,819,206 A | 10/1998 | Horton et al. |
| 5,915,673 A | 6/1999 | Kazerooni |
| 5,930,741 A | 7/1999 | Kramer |
| 5,961,541 A | 10/1999 | Ferrati |
| 5,980,472 A | 11/1999 | Seyl |
| 5,989,700 A | 11/1999 | Krivopal |
| 6,003,340 A | 12/1999 | Borak et al. |
| 6,005,548 A | 12/1999 | Latypov et al. |
| 6,018,705 A | 1/2000 | Gaudet et al. |
| 6,032,530 A | 3/2000 | Hock |
| 6,035,274 A | 3/2000 | Kramer et al. |
| 6,042,555 A | 3/2000 | Kramer et al. |
| 6,050,962 A | 4/2000 | Kramer et al. |
| 6,059,576 A | 5/2000 | Brann |
| 6,095,991 A | 8/2000 | Krausman et al. |
| 6,104,379 A | 8/2000 | Petrich et al. |
| 6,110,130 A | 8/2000 | Kramer |
| 6,119,516 A | 9/2000 | Hock |
| 6,127,672 A | 10/2000 | Danisch |
| 6,148,280 A | 11/2000 | Kramer |
| 6,162,190 A | 12/2000 | Kramer |
| 6,162,191 A | 12/2000 | Foxlin |
| 6,210,301 B1 | 4/2001 | Abraham-Fuchs et al. |
| 6,239,784 B1 | 5/2001 | Holmes |
| 6,246,390 B1 | 6/2001 | Rosenberg |
| 6,304,840 B1 | 10/2001 | Vance et al. |
| 6,334,852 B1 | 1/2002 | Seyl |
| 6,341,504 B1 | 1/2002 | Istook |
| 6,360,615 B1 | 3/2002 | Smela |
| 6,361,507 B1 | 3/2002 | Foxlin |
| 6,389,187 B1 | 5/2002 | Greenaway et al. |
| 6,409,687 B1 | 6/2002 | Foxlin |
| 6,413,229 B1 | 7/2002 | Kramer et al. |
| 6,428,490 B1 | 8/2002 | Kramer et al. |
| 6,429,421 B1 | 8/2002 | Meller et al. |
| 6,466,200 B1 | 10/2002 | Anton et al. |
| 6,487,906 B1 | 12/2002 | Hock |
| 6,497,672 B2 | 12/2002 | Kramer |
| 6,513,532 B2 | 2/2003 | Mault et al. |
| 6,563,107 B2 | 5/2003 | Danisch et al. |
| 6,579,248 B1 | 6/2003 | Cascone et al. |
| 6,611,141 B1 | 8/2003 | Schulz et al. |
| 6,611,789 B1 | 8/2003 | Darley |
| 6,621,948 B1 | 9/2003 | Devenyi |
| 6,640,202 B1 | 10/2003 | Dietz et al. |
| 6,666,831 B1 | 12/2003 | Edgerton et al. |
| 6,673,027 B2 | 1/2004 | Fischer |
| 6,691,074 B1 | 2/2004 | Moriya et al. |
| 6,700,499 B2 | 3/2004 | Kubo et al. |
| 6,701,296 B1 | 3/2004 | Kramer et al. |
| 6,703,939 B2 | 3/2004 | Lehrman et al. |
| 6,728,431 B2 | 4/2004 | Ames et al. |
| 6,731,268 B2 | 5/2004 | Anton et al. |
| 6,786,877 B2 | 9/2004 | Foxlin |
| 6,834,436 B2 | 12/2004 | Townsend et al. |
| 6,836,744 B1 | 12/2004 | Asphahani et al. |
| 6,864,796 B2 | 3/2005 | Lehrman et al. |
| 6,866,643 B2 | 3/2005 | Kramer |
| 6,871,413 B1 | 3/2005 | Arms et al. |
| 6,890,312 B1 | 5/2005 | Priester et al. |
| 6,912,475 B2 | 6/2005 | Moriya et al. |
| 6,940,062 B2 | 9/2005 | Kwon et al. |
| 6,957,164 B2 | 10/2005 | Dietz et al. |
| 6,964,205 B2 | 11/2005 | Papakostas et al. |
| 6,979,164 B2 | 12/2005 | Kramer |
| 6,985,134 B2 | 1/2006 | Suprun et al. |
| 7,020,508 B2 | 3/2006 | Stivoric et al. |
| 7,028,547 B2 | 4/2006 | Shiratori et al. |
| 7,070,571 B2 | 7/2006 | Kramer et al. |
| 7,082,570 B1 | 7/2006 | von Wiegand et al. |
| 7,095,331 B2 | 8/2006 | Lehrman et al. |
| 7,135,227 B2 | 11/2006 | Karayianni et al. |
| 7,141,026 B2 | 11/2006 | Aminian et al. |
| 7,145,461 B2 | 12/2006 | Lehrman et al. |
| 7,149,584 B1 | 12/2006 | Koh et al. |
| 7,153,242 B2 | 12/2006 | Goffer |
| 7,167,743 B2 | 1/2007 | Heruth et al. |
| 7,191,652 B2 | 3/2007 | Pristup et al. |
| 7,191,803 B2 | 3/2007 | Orr et al. |
| 7,209,028 B2 | 4/2007 | Boronkay et al. |
| 7,210,240 B2 | 5/2007 | Townsend et al. |
| 7,212,943 B2 | 5/2007 | Aoshima et al. |
| 7,219,033 B2 | 5/2007 | Kolen |
| 7,245,292 B1 | 7/2007 | Custy |
| 7,258,026 B2 | 8/2007 | Papakostas et al. |
| 7,261,690 B2 | 8/2007 | Teller et al. |
| 7,264,554 B2 | 9/2007 | Bentley |

(56) References Cited

U.S. PATENT DOCUMENTS

| | | |
|---|---|---|
| 7,285,090 B2 | 10/2007 | Stivoric et al. |
| 7,292,151 B2 | 11/2007 | Ferguson et al. |
| 7,292,223 B2 | 11/2007 | Suprun et al. |
| 7,295,184 B2 | 11/2007 | Suprun et al. |
| 7,296,469 B2 | 11/2007 | Simonenko et al. |
| 7,313,440 B2 | 12/2007 | Miesel |
| 7,324,714 B1 | 1/2008 | Cranch et al. |
| 7,330,760 B2 | 2/2008 | Heruth et al. |
| 7,383,728 B2 | 6/2008 | Noble et al. |
| 7,390,157 B2 | 6/2008 | Kramer |
| 7,394,385 B2 | 7/2008 | Franco et al. |
| 7,395,113 B2 | 7/2008 | Heruth et al. |
| 7,395,181 B2 | 7/2008 | Foxlin |
| 7,410,338 B2 | 8/2008 | Schiele et al. |
| 7,413,802 B2 | 8/2008 | Karayianni et al. |
| 7,421,369 B2 | 9/2008 | Clarkson |
| 7,447,545 B2 | 11/2008 | Heruth et al. |
| 7,450,002 B2 | 11/2008 | Choi et al. |
| 7,451,056 B2 | 11/2008 | Flentov et al. |
| 7,471,290 B2 | 12/2008 | Wang et al. |
| 7,479,890 B2 | 1/2009 | Lehrman et al. |
| 7,487,043 B2 | 2/2009 | Adams |
| 7,492,268 B2 | 2/2009 | Ferguson et al. |
| 7,500,853 B2 | 3/2009 | Bevirt et al. |
| 7,509,870 B2 | 3/2009 | Aebersold et al. |
| 7,512,515 B2 | 3/2009 | Vock et al. |
| 7,565,295 B1 | 7/2009 | Hernandez-Rebollar |
| 7,602,301 B1 | 10/2009 | Stirling et al. |
| 7,602,310 B2 | 10/2009 | Mann et al. |
| 7,627,451 B2 | 12/2009 | Vock et al. |
| 7,630,591 B2 | 12/2009 | Allen et al. |
| 7,634,379 B2 | 12/2009 | Noble |
| 7,647,196 B2 | 1/2010 | Kahn et al. |
| 7,653,214 B2 | 1/2010 | Schroeder et al. |
| 7,653,508 B1 | 1/2010 | Kahn et al. |
| 7,661,200 B2 | 2/2010 | Bonnet et al. |
| 7,665,288 B2 | 2/2010 | Karayianni et al. |
| 7,668,588 B2 | 2/2010 | Kovacs |
| 7,672,781 B2 | 3/2010 | Churchill et al. |
| 7,689,378 B2 | 3/2010 | Kolen |
| 7,698,101 B2 | 4/2010 | Alten et al. |
| 7,698,830 B2 | 4/2010 | Townsend et al. |
| 7,703,333 B2 | 4/2010 | Hayakawa et al. |
| 7,725,279 B2 | 5/2010 | Luinge et al. |
| 7,742,894 B2 | 6/2010 | Chen et al. |
| 7,753,861 B1 | 7/2010 | Kahn et al. |
| 7,771,318 B2 | 8/2010 | Narayanaswami |
| 7,772,541 B2 | 8/2010 | Froggatt et al. |
| 7,781,724 B2 | 8/2010 | Childers et al. |
| 7,792,583 B2 | 9/2010 | Miesel et al. |
| 7,805,196 B2 | 9/2010 | Miesel et al. |
| 7,811,333 B2 | 10/2010 | Jonsson et al. |
| 7,815,376 B2 | 10/2010 | Rogers et al. |
| 7,821,407 B2 | 10/2010 | Shears et al. |
| 7,825,815 B2 | 11/2010 | Shears et al. |
| 7,827,000 B2 | 11/2010 | Stirling et al. |
| 7,845,228 B2 | 12/2010 | Bremer et al. |
| 7,850,574 B2 | 12/2010 | Narayanaswami |
| 7,854,174 B2 | 12/2010 | Aebersold et al. |
| 7,881,902 B1 | 2/2011 | Kahn et al. |
| 7,899,556 B2 | 3/2011 | Nathan et al. |
| 7,901,756 B2 | 3/2011 | Burr et al. |
| 7,902,095 B2 | 3/2011 | Hassonjee et al. |
| 7,911,620 B2 | 3/2011 | Digonnet et al. |
| 7,926,254 B2 | 4/2011 | Karayianni et al. |
| 7,930,065 B2 | 4/2011 | Larkin et al. |
| 7,952,483 B2 | 5/2011 | Ferguson et al. |
| 7,978,081 B2 | 7/2011 | Shears et al. |
| 7,980,141 B2 | 7/2011 | Connor et al. |
| 7,981,057 B2 | 7/2011 | Stewart |
| 7,981,058 B2 | 7/2011 | Akay |
| 7,998,092 B2 | 8/2011 | Avni et al. |
| 7,999,946 B2 | 8/2011 | Andersen et al. |
| 8,010,308 B1 | 8/2011 | Churchill |
| 8,011,229 B2 | 9/2011 | Lieberman et al. |
| 8,025,632 B2 | 9/2011 | Einarsson |
| 8,033,916 B2 | 10/2011 | Caldwell et al. |
| 8,036,850 B2 | 10/2011 | Kulach et al. |
| 8,036,851 B2 | 10/2011 | Vock et al. |
| 8,055,021 B2 | 11/2011 | Caritu et al. |
| 8,060,337 B2 | 11/2011 | Kulach et al. |
| 8,068,231 B2 | 11/2011 | Digonnet |
| 8,073,707 B2 | 12/2011 | Teller et al. |
| 8,075,499 B2 | 12/2011 | Nathan et al. |
| 8,083,693 B1 | 12/2011 | McKeon et al. |
| 8,099,258 B2 | 1/2012 | Alten et al. |
| 8,109,149 B2 | 2/2012 | Kotovsky |
| 8,111,165 B2 | 2/2012 | Ortega et al. |
| 8,116,601 B2 | 2/2012 | Prisco |
| 8,125,448 B2 | 2/2012 | Ranta et al. |
| 8,135,473 B2 | 3/2012 | Miesel et al. |
| 8,140,339 B2 | 3/2012 | Hernandez-Rebollar |
| 8,150,531 B2 | 4/2012 | Skelton |
| 8,151,648 B2 | 4/2012 | Yu et al. |
| 8,152,694 B2 | 4/2012 | Srinivasan et al. |
| 8,157,730 B2 | 4/2012 | Leboeuf et al. |
| 8,157,731 B2 | 4/2012 | Teller et al. |
| 8,157,752 B2 | 4/2012 | Fischer |
| 8,159,354 B2 | 4/2012 | Ferguson et al. |
| 8,161,826 B1 | 4/2012 | Taylor |
| 8,162,857 B2 | 4/2012 | Lanfermann et al. |
| 8,165,840 B2 | 4/2012 | Hatlestad et al. |
| 8,165,844 B2 | 4/2012 | Luinge et al. |
| 8,171,570 B2 | 5/2012 | Adarraga |
| 8,175,720 B2 | 5/2012 | Skelton et al. |
| 8,180,591 B2 | 5/2012 | Yuen et al. |
| 8,180,592 B2 | 5/2012 | Yuen et al. |
| 8,182,158 B2 | 5/2012 | Rogers et al. |
| 8,187,182 B2 | 5/2012 | Kahn et al. |
| 8,200,340 B2 | 6/2012 | Skelton et al. |
| 8,203,455 B2 | 6/2012 | Lee et al. |
| 8,203,487 B2 | 6/2012 | Hol et al. |
| 8,206,325 B1 | 6/2012 | Najafi et al. |
| 8,209,028 B2 | 6/2012 | Skelton et al. |
| 8,209,147 B2 | 6/2012 | Solinsky |
| 8,219,206 B2 | 7/2012 | Skelton et al. |
| 8,231,555 B2 | 7/2012 | Skelton et al. |
| 8,233,151 B2 | 7/2012 | Digonnet |
| 8,240,207 B2 | 8/2012 | Andersen et al. |
| 8,249,718 B2 | 8/2012 | Skelton et al. |
| 8,275,635 B2 | 9/2012 | Stivoric et al. |
| 8,280,517 B2 | 10/2012 | Skelton et al. |
| 8,280,681 B2 | 10/2012 | Vock et al. |
| 8,282,580 B2 | 10/2012 | Skelton et al. |
| 8,284,847 B2 | 10/2012 | Adermann |
| 8,301,575 B2 | 10/2012 | Bonnet et al. |
| 8,311,769 B2 | 11/2012 | Yuen et al. |
| 8,311,770 B2 | 11/2012 | Yuen et al. |
| 8,315,710 B2 | 11/2012 | Skelton et al. |
| 8,316,719 B2 | 11/2012 | Majidi et al. |
| 8,323,218 B2 | 12/2012 | Davis et al. |
| 8,328,718 B2 | 12/2012 | Tran |
| 8,332,041 B2 | 12/2012 | Skelton et al. |
| 8,342,045 B2 | 1/2013 | Maxwell et al. |
| 8,352,211 B2 | 1/2013 | Vock et al. |
| 8,358,883 B2 | 1/2013 | Prisco |
| 8,362,882 B2 | 1/2013 | Heubel et al. |
| 8,366,641 B2 | 2/2013 | Wang et al. |
| 8,382,590 B2 | 2/2013 | Stivoric et al. |
| 8,384,551 B2 | 2/2013 | Ross et al. |
| 8,386,008 B2 | 2/2013 | Yuen et al. |
| 8,388,555 B2 | 3/2013 | Panken et al. |
| 8,395,109 B2 | 3/2013 | Muravsky |
| 8,396,554 B2 | 3/2013 | Miesel et al. |
| 8,396,565 B2 | 3/2013 | Singhal et al. |
| 8,397,568 B2 | 3/2013 | Cardarelli |
| 8,401,666 B2 | 3/2013 | Skelton et al. |
| 8,414,507 B2 | 4/2013 | Asada |
| 8,416,088 B2 | 4/2013 | Ortega et al. |
| 8,416,102 B2 | 4/2013 | Yin |
| 8,421,448 B1 | 4/2013 | Tran et al. |
| 8,421,854 B2 | 4/2013 | Zerkin |
| 8,427,325 B2 | 4/2013 | Ferguson et al. |
| 8,427,651 B2 | 4/2013 | Digonnet |

(56) References Cited

U.S. PATENT DOCUMENTS

| | | |
|---|---|---|
| 8,435,177 B2 | 5/2013 | Lanfermann et al. |
| 8,436,737 B1 | 5/2013 | Trout |
| 8,437,824 B2 | 5/2013 | Moon et al. |
| 8,437,861 B2 | 5/2013 | Skelton et al. |
| 8,437,980 B2 | 5/2013 | Yuen et al. |
| 8,446,275 B2 | 5/2013 | Utter |
| 8,447,401 B2 | 5/2013 | Miesel et al. |
| 8,447,411 B2 | 5/2013 | Skelton et al. |
| 8,459,128 B2 | 6/2013 | Bhat et al. |
| 8,460,197 B1 | 6/2013 | Brady et al. |
| 8,463,573 B2 | 6/2013 | Flentov et al. |
| 8,463,576 B2 | 6/2013 | Yuen et al. |
| 8,463,577 B2 | 6/2013 | Yuen et al. |
| 8,504,150 B2 | 8/2013 | Skelton |
| 8,515,549 B2 | 8/2013 | Panken et al. |
| 8,515,550 B2 | 8/2013 | Skelton et al. |
| 8,520,472 B2 | 8/2013 | Murray et al. |
| 8,527,217 B2 | 9/2013 | Moodie |
| 8,543,185 B2 | 9/2013 | Yuen et al. |
| 8,543,351 B2 | 9/2013 | Yuen et al. |
| 8,548,740 B2 | 10/2013 | Hesch et al. |
| 8,548,770 B2 | 10/2013 | Yuen et al. |
| 8,554,297 B2 | 10/2013 | Moon et al. |
| 8,579,834 B2 | 11/2013 | Davis et al. |
| 8,583,252 B2 | 11/2013 | Skelton et al. |
| 8,583,402 B2 | 11/2013 | Yuen et al. |
| 8,616,782 B2 | 12/2013 | Rogers et al. |
| 8,616,989 B2 | 12/2013 | Bentley |
| 8,626,472 B2 | 1/2014 | Solinsky |
| 8,643,494 B1 | 2/2014 | Trout |
| 8,651,964 B2 | 2/2014 | Brick |
| 8,655,117 B2 | 2/2014 | Donlagic et al. |
| 8,655,618 B2 | 2/2014 | Flaction et al. |
| 8,657,772 B2 | 2/2014 | Einarsson |
| 8,661,915 B2 | 3/2014 | Taylor |
| 8,665,241 B2 | 3/2014 | Heubel et al. |
| 8,670,953 B2 | 3/2014 | Yuen et al. |
| 8,678,979 B2 | 3/2014 | Stark et al. |
| 8,708,825 B2 | 4/2014 | Crisco |
| 8,708,904 B2 | 4/2014 | Stivoric et al. |
| 8,712,723 B1 | 4/2014 | Kahn et al. |
| 8,760,392 B2 | 6/2014 | Lloyd et al. |
| 8,764,651 B2 | 7/2014 | Tran |
| 8,777,878 B2 | 7/2014 | Deitz |
| 8,780,339 B2 | 7/2014 | Udd |
| 8,784,303 B2 | 7/2014 | Laby et al. |
| 8,784,342 B2 | 7/2014 | Hyde et al. |
| 8,788,055 B2 | 7/2014 | Gerber et al. |
| 8,795,137 B2 | 8/2014 | Ellis et al. |
| 8,818,748 B2 | 8/2014 | Hatlestad et al. |
| 8,821,417 B2 | 9/2014 | McGregor et al. |
| 8,823,490 B2 | 9/2014 | Libbus et al. |
| 8,849,610 B2 | 9/2014 | Molettiere et al. |
| 8,876,738 B1 | 11/2014 | Kahn et al. |
| 8,904,876 B2 | 12/2014 | Taylor et al. |
| 8,905,948 B2 | 12/2014 | Davis et al. |
| 8,909,543 B2 | 12/2014 | Tropper et al. |
| 8,928,484 B2 | 1/2015 | Chang et al. |
| 8,929,966 B2 | 1/2015 | LeBoeuf et al. |
| 8,932,236 B1 | 1/2015 | McKeon et al. |
| 8,944,939 B2 | 2/2015 | Clark et al. |
| 8,947,441 B2 | 2/2015 | Hodgins et al. |
| 8,949,070 B1 | 2/2015 | Kahn et al. |
| 8,958,885 B2 | 2/2015 | Panken et al. |
| 2001/0003712 A1 | 6/2001 | Roelofs |
| 2001/0020140 A1 | 9/2001 | Kramer |
| 2001/0049470 A1 | 12/2001 | Mault et al. |
| 2002/0024656 A1 | 2/2002 | Kwon et al. |
| 2002/0088931 A1 | 7/2002 | Danisch et al. |
| 2002/0151824 A1 | 10/2002 | Fischer |
| 2002/0198472 A1 | 12/2002 | Kramer |
| 2003/0023192 A1 | 1/2003 | Foxlin |
| 2003/0045816 A1 | 3/2003 | Foxlin |
| 2003/0047002 A1 | 3/2003 | Arms et al. |
| 2003/0054923 A1 | 3/2003 | Brassil et al. |
| 2003/0083596 A1 | 5/2003 | Kramer et al. |
| 2003/0091966 A1 | 5/2003 | Collodi |
| 2003/0120448 A1 | 6/2003 | Moriya et al. |
| 2005/0126026 A1 | 6/2005 | Townsend et al. |
| 2005/0140651 A1 | 6/2005 | Suprun et al. |
| 2006/0022833 A1 | 2/2006 | Ferguson et al. |
| 2006/0059976 A1 | 3/2006 | Simonenko et al. |
| 2006/0059988 A1 | 3/2006 | Pristup |
| 2006/0059990 A1 | 3/2006 | Simonenko et al. |
| 2006/0059991 A1 | 3/2006 | Pristup et al. |
| 2006/0070443 A1 | 4/2006 | Pristup |
| 2006/0130347 A1 | 6/2006 | Bergamasco et al. |
| 2006/0135883 A1 | 6/2006 | Jonsson et al. |
| 2006/0166737 A1 | 7/2006 | Bentley |
| 2006/0167564 A1 | 7/2006 | Flaherty et al. |
| 2006/0184336 A1 | 8/2006 | Kolen |
| 2006/0189899 A1 | 8/2006 | Flaherty et al. |
| 2006/0212097 A1 | 9/2006 | Varadan et al. |
| 2006/0217233 A1 | 9/2006 | Lee |
| 2006/0240953 A1 | 10/2006 | Shahinpoor |
| 2006/0241521 A1 | 10/2006 | Cohen |
| 2006/0282017 A1 | 12/2006 | Avni et al. |
| 2006/0284979 A1 | 12/2006 | Clarkson |
| 2007/0000324 A9 | 1/2007 | Pristup et al. |
| 2007/0038038 A1 | 2/2007 | Stivoric et al. |
| 2007/0073482 A1 | 3/2007 | Churchill et al. |
| 2007/0100666 A1 | 5/2007 | Stivoric et al. |
| 2007/0123997 A1 | 5/2007 | Herr et al. |
| 2007/0132722 A1 | 6/2007 | Kim et al. |
| 2007/0169364 A1 | 7/2007 | Townsend et al. |
| 2007/0173705 A1 | 7/2007 | Teller et al. |
| 2007/0214889 A1 | 9/2007 | Pristup |
| 2007/0219744 A1 | 9/2007 | Kolen |
| 2007/0256502 A1 | 11/2007 | Aebersold et al. |
| 2007/0270214 A1 | 11/2007 | Bentley |
| 2008/0036737 A1 | 2/2008 | Hernandez-Rebollar |
| 2008/0061949 A1 | 3/2008 | Ferguson et al. |
| 2008/0084385 A1 | 4/2008 | Ranta et al. |
| 2008/0167535 A1 | 7/2008 | Stivoric et al. |
| 2008/0285805 A1 | 11/2008 | Luinge et al. |
| 2009/0025483 A1 | 1/2009 | Connor et al. |
| 2009/0030345 A1 | 1/2009 | Bonnet et al. |
| 2009/0076419 A1 | 3/2009 | Namineni et al. |
| 2009/0149257 A1 | 6/2009 | Ferguson et al. |
| 2009/0171180 A1 | 7/2009 | Pering et al. |
| 2009/0188325 A1 | 7/2009 | Aebersold et al. |
| 2009/0204031 A1 | 8/2009 | McNames et al. |
| 2009/0278791 A1 | 11/2009 | Slycke et al. |
| 2010/0026809 A1 | 2/2010 | Curry |
| 2010/0036288 A1 | 2/2010 | Lanfermann et al. |
| 2010/0076348 A1 | 3/2010 | McNames et al. |
| 2010/0176952 A1 | 7/2010 | Bajcsy et al. |
| 2010/0183297 A1 | 7/2010 | Barboutis et al. |
| 2010/0198113 A1 | 8/2010 | Coulston |
| 2010/0211349 A1 | 8/2010 | Flaction et al. |
| 2010/0225473 A1 | 9/2010 | Leuthardt et al. |
| 2010/0225474 A1 | 9/2010 | Leuthardt et al. |
| 2010/0225490 A1 | 9/2010 | Leuthardt et al. |
| 2010/0225491 A1 | 9/2010 | Leuthardt et al. |
| 2010/0225498 A1 | 9/2010 | Leuthardt et al. |
| 2010/0228153 A1 | 9/2010 | Leuthardt et al. |
| 2010/0228154 A1 | 9/2010 | Leuthardt et al. |
| 2010/0228158 A1 | 9/2010 | Leuthardt et al. |
| 2010/0228159 A1 | 9/2010 | Leuthardt et al. |
| 2010/0228487 A1 | 9/2010 | Leuthardt et al. |
| 2010/0228488 A1 | 9/2010 | Leuthardt et al. |
| 2010/0228489 A1 | 9/2010 | Leuthardt et al. |
| 2010/0228490 A1 | 9/2010 | Leuthardt et al. |
| 2010/0228492 A1 | 9/2010 | Leuthardt et al. |
| 2010/0228493 A1 | 9/2010 | Leuthardt et al. |
| 2010/0228494 A1 | 9/2010 | Leuthardt et al. |
| 2010/0228495 A1 | 9/2010 | Leuthardt et al. |
| 2010/0271200 A1 | 10/2010 | Leuthardt et al. |
| 2010/0309209 A1 | 12/2010 | Hodgins et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |

(56) References Cited

U.S. PATENT DOCUMENTS

| | | |
|---|---|---|
| 2010/0324389 A1 | 12/2010 | Moon et al. |
| 2010/0324456 A1 | 12/2010 | Jonsson et al. |
| 2011/0025562 A1 | 2/2011 | Hol et al. |
| 2011/0028865 A1 | 2/2011 | Luinge et al. |
| 2011/0040216 A1 | 2/2011 | Herr et al. |
| 2011/0046518 A1 | 2/2011 | Fischer |
| 2011/0046915 A1 | 2/2011 | Hol et al. |
| 2011/0052005 A1 | 3/2011 | Selner |
| 2011/0181422 A1 | 7/2011 | Tran |
| 2011/0201428 A1 | 8/2011 | Ferguson et al. |
| 2011/0208444 A1 | 8/2011 | Solinsky |
| 2011/0248773 A1 | 10/2011 | Poupyrev et al. |
| 2011/0313705 A1 | 12/2011 | Esser et al. |
| 2012/0046901 A1 | 2/2012 | Green et al. |
| 2012/0089348 A1 | 4/2012 | Perlin et al. |
| 2012/0092156 A1 | 4/2012 | Tran |
| 2012/0108917 A1 | 5/2012 | Libbus et al. |
| 2012/0116257 A1 | 5/2012 | Leuthardt et al. |
| 2012/0118066 A1 | 5/2012 | Majidi et al. |
| 2012/0172126 A1 | 7/2012 | Padovani et al. |
| 2012/0178534 A1 | 7/2012 | Ferguson et al. |
| 2012/0223880 A1 | 9/2012 | Birnbaum et al. |
| 2012/0274554 A1 | 11/2012 | Kinoshita et al. |
| 2012/0316455 A1 | 12/2012 | Rahman et al. |
| 2012/0319940 A1 | 12/2012 | Bress et al. |
| 2012/0323501 A1 | 12/2012 | Sarrafzadeh et al. |
| 2013/0015976 A1 | 1/2013 | Chang et al. |
| 2013/0068017 A1 | 3/2013 | Perkins et al. |
| 2013/0072765 A1 | 3/2013 | Kahn et al. |
| 2013/0073248 A1 | 3/2013 | Perkins et al. |
| 2013/0110011 A1 | 5/2013 | McGregor et al. |
| 2013/0113506 A1 | 5/2013 | Poupyrev et al. |
| 2013/0123665 A1 | 5/2013 | Mariani et al. |
| 2013/0158444 A1 | 6/2013 | Herr et al. |
| 2013/0158686 A1 | 6/2013 | Zhang et al. |
| 2013/0173171 A1 | 7/2013 | Drysdale et al. |
| 2013/0204411 A1 | 8/2013 | Clark et al. |
| 2013/0204435 A1 | 8/2013 | Moon et al. |
| 2013/0207889 A1 | 8/2013 | Chang et al. |
| 2013/0211291 A1 | 8/2013 | Tran |
| 2013/0215230 A1 | 8/2013 | Miesnieks et al. |
| 2013/0222565 A1 | 8/2013 | Guerin et al. |
| 2013/0253875 A1 | 9/2013 | Flentov et al. |
| 2013/0275057 A1 | 10/2013 | Perlin et al. |
| 2013/0289932 A1 | 10/2013 | Baechler |
| 2013/0303286 A1 | 11/2013 | Ferguson et al. |
| 2013/0324888 A1 | 12/2013 | Solinsky |
| 2014/0031698 A1 | 1/2014 | Moon et al. |
| 2014/0070957 A1 | 3/2014 | Longinotti-Buitoni et al. |
| 2014/0142733 A1 | 5/2014 | Tropper et al. |
| 2014/0143031 A1 | 5/2014 | Tropper et al. |
| 2014/0143038 A1 | 5/2014 | Tropper et al. |
| 2014/0159894 A1 | 6/2014 | Tropper et al. |
| 2014/0171834 A1 | 6/2014 | Degoede et al. |
| 2014/0172134 A1* | 6/2014 | Meschter ............ A61B 5/6804 700/91 |
| 2014/0188499 A1 | 7/2014 | Bell et al. |
| 2014/0194781 A1 | 7/2014 | Einarsson |
| 2014/0197946 A1 | 7/2014 | Park |
| 2014/0197963 A1 | 7/2014 | Park et al. |
| 2014/0197965 A1 | 7/2014 | Park et al. |
| 2014/0206327 A1 | 7/2014 | Ziemianska et al. |
| 2014/0213856 A1 | 7/2014 | Teller et al. |
| 2014/0213857 A1 | 7/2014 | Teller et al. |
| 2014/0221769 A1 | 8/2014 | Teller et al. |
| 2014/0223407 A1 | 8/2014 | Teller et al. |
| 2014/0240103 A1 | 8/2014 | Lake et al. |
| 2014/0240122 A1 | 8/2014 | Roberts et al. |
| 2014/0249381 A1 | 9/2014 | LeBoeuf et al. |
| 2014/0275812 A1 | 9/2014 | Stivoric et al. |
| 2014/0275813 A1 | 9/2014 | Stivoric et al. |
| 2014/0288875 A1 | 9/2014 | Donaldson |
| 2014/0288877 A1 | 9/2014 | Donaldson |
| 2014/0288878 A1 | 9/2014 | Donaldson |
| 2014/0342844 A1 | 11/2014 | Mooney |
| 2014/0366675 A1 | 12/2014 | Gosselin et al. |
| 2015/0005608 A1 | 1/2015 | Evans et al. |
| 2015/0015417 A1 | 1/2015 | Libbus et al. |
| 2015/0019135 A1 | 1/2015 | Kacyvenski et al. |
| 2015/0045699 A1 | 2/2015 | Mokaya et al. |

* cited by examiner

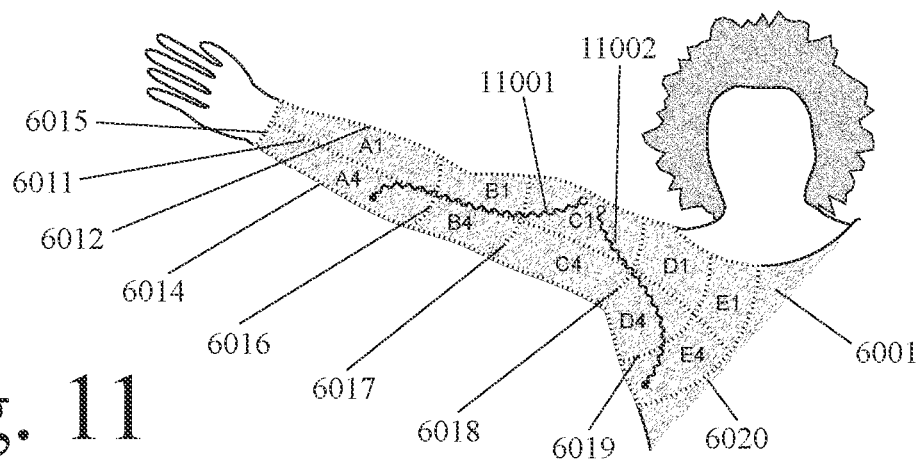
Fig. 11
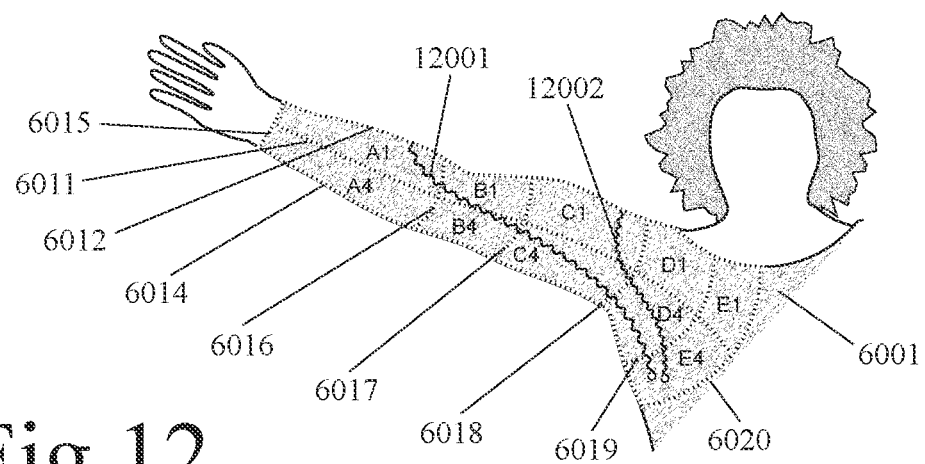
Fig. 12
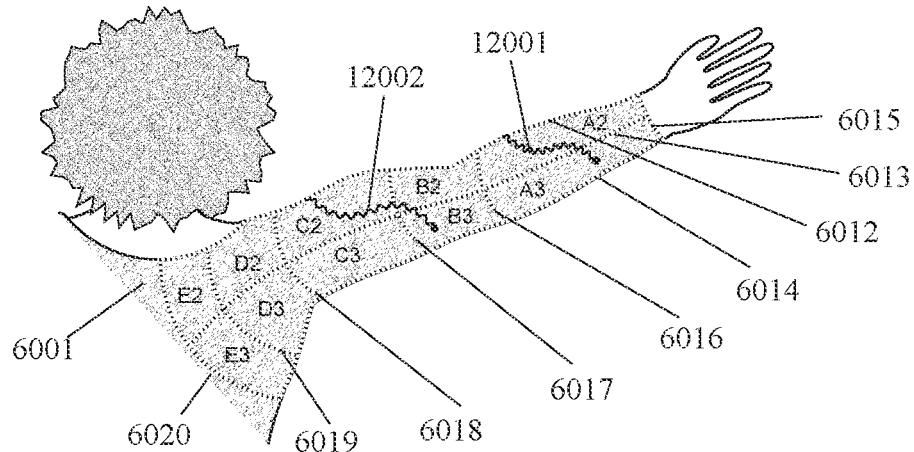

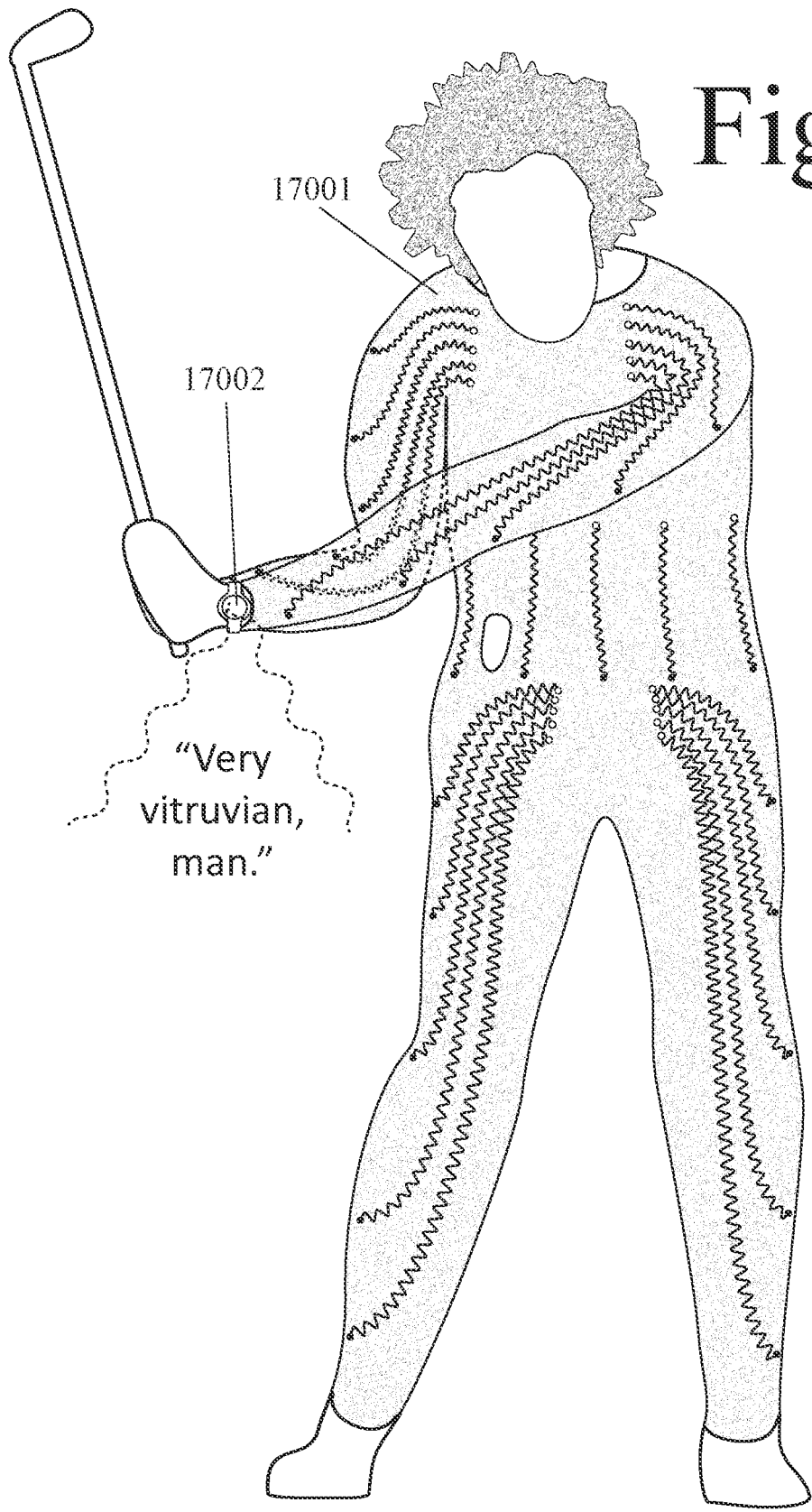

SMART CLOTHING WITH CONVERGING/DIVERGING BEND OR STRETCH SENSORS FOR MEASURING BODY MOTION OR CONFIGURATION

CROSS-REFERENCE TO RELATED APPLICATIONS

This patent application:

(A) is a continuation-in-part of U.S. patent application Ser. No. 14, 795,373 entitled "Electromyographic Clothing" by Robert A. Connor filed on Jul. 9, 2015 which, in turn: (1) is a continuation-in-part of U.S. patent application Ser. No. 14, 736,652 entitled "Smart Clothing with Human-to-Computer Textile Interface" by Robert A. Connor filed on Jun. 11, 2015 which: is a continuation-in-part of U.S. patent application Ser. No. 14, 664,832 entitled "Motion Recognition Clothing [™] with Flexible Electromagnetic, Light, or Sonic Energy Pathways" by Robert A. Connor filed on Mar. 21, 2015, claims the priority benefit of U.S. Provisional Patent Application 62/014,747 entitled "Modular Smart Clothing" by Robert A. Connor filed on Jun. 20, 2014, and claims the priority benefit of U.S. Provisional Patent Application 62/100,217 entitled "Forearm Wearable Device with Distal-to-Proximal Flexibly-Connected Display Modules" filed by Robert A. Connor on Jan. 6, 2015; (2) claims the priority benefit of U.S. Provisional Patent Application 62/065,032 entitled "Electromyographic Clothing: Work In Progress" by Robert A. Connor filed on Oct. 17, 2014; (3) claims the priority benefit of U.S. Provisional Patent Application 62/086,053 entitled "Electromyographic Clothing" by Robert A. Connor filed on Dec. 1, 2014; (4) claims the priority benefit of U.S. Provisional Patent Application 62/182,473 entitled "Customized Electromyographic Clothing with Adjustable EMG Sensor Configurations" by Robert A. Connor filed on Jun. 20, 2015; and (5) claims the priority benefit of U.S. Provisional Patent Application 62/187,906 entitled "Introduction and Further Examples of Electromyographic Clothing" by Robert A. Connor filed on Jul. 2, 2015;

(B) is a continuation-in-part of U.S. patent application Ser. No. 15, 227,254 entitled "Smart Clothing for Ambulatory Human Motion Capture" by Robert A. Connor filed on Aug. 3, 2016 which, in turn: (1) is a continuation in part of U.S. patent application Ser. No. 14, 664,832 entitled "Motion Recognition Clothing(™) with Flexible Electromagnetic, Light, or Sonic Energy Pathways" by Robert A. Connor filed on Mar. 21, 2015 which is: a continuation in part of U.S. patent application Ser. No. 14, 463,741 by Robert A. Connor et al. filed on Aug. 20, 2014 which claims the priority benefit of U.S. Provisional Patent Application No. 61/878,893 by Robert A. Connor et al. filed on Sep. 17, 2013; and claims the priority benefit of U.S. Provisional Patent Application No. 61/976,650 by Robert A. Connor filed on Apr. 8, 2014; (2) is a continuation in part of U.S. patent application Ser. No. 15, 079,447 entitled "Sensor Array Spanning Multiple Radial Quadrants to Measure Body Joint Movement" by Robert A. Connor filed on Mar. 24, 2016 which in turn was: a continuation in part of U.S. patent application Ser. No. 14, 463,741 by Robert A. Connor et al. filed on Aug. 20, 2014 which claims the priority benefit of U.S. Provisional Patent Application No. 61/878,893 by Robert A. Connor et al. filed on Sep. 17, 2013; a continuation in part of U.S. patent application Ser. No. 14, 664,832 by Robert A. Connor filed on Mar. 21, 2015, which is a continuation in part of U.S. patent application Ser. No. 14, 463,741 by Robert A. Connor et al. filed on Aug. 20, 2014 which claims the priority benefit of U.S. Provisional Patent Application No. 61/878,893 by Robert A. Connor et al. filed on Sep. 17, 2013 and claims the priority benefit of U.S. Provisional Patent Application No. 61/976,650 by Robert A. Connor filed on Apr. 8, 2014; and claims the priority benefit of U.S. Provisional Patent Application No. 62/150,886 by Robert A. Connor filed on Apr. 22, 2015; (3) is a continuation in part of U.S. patent application Ser. No. 15, 130,995 entitled "Nerd of the Rings—Devices for Measuring Finger Motion and Recognizing Hand Gestures" by Robert A. Connor filed on Apr. 17, 2016 which claims the priority benefit of U.S. Provisional Patent Application No. 62/150,886 by Robert A. Connor filed on Apr. 22, 2015; (4) is a continuation in part of U.S. patent application Ser. No. 14, 736,652 entitled "Smart Clothing with Human-to-Computer Textile Interface" by Robert A. Connor filed on Jun. 11, 2015 which in turn was: a continuation-in-part of U.S. patent application Ser. No. 14, 664,832 by Robert A. Connor filed on Mar. 21, 2015; claims the priority benefit of U.S. Provisional Patent Application No. 62/014,747 by Robert A. Connor filed on Jun. 20, 2014; and claims the priority benefit of U.S. Provisional Patent Application No. 62/100,217 filed by Robert A. Connor on Jan. 6, 2015; and (5) claims the priority benefit of U.S. Provisional Patent Application No. 62/357,957 entitled "Motion Recognition Clothing (™) with a Combination of Inertial Motion Sensors and Stretching/Bending Motion Sensors" by Robert A. Connor filed on Jul. 2, 2016;

(C) claims the priority benefit of U.S. Provisional Patent Application 62/449,735 entitled "Smart Clothing with Converging/Diverging Bend or Stretch Sensors for Measuring Body Motion or Configuration" by Robert A. Connor filed on Jan. 24, 2017; and (D) claims the priority benefit of U.S. Provisional Patent Application 62/538,793 entitled "Motion Recognition Fabric" by Robert A. Connor filed on Jul. 30, 2017.

The entire contents of these applications are incorporated herein by reference.

FEDERALLY SPONSORED RESEARCH

Not Applicable

SEQUENCE LISTING OR PROGRAM

Not Applicable

BACKGROUND-FIELD OF INVENTION

This invention relates to articles of clothing for measuring body motion, posture, and/or configuration.

INTRODUCTION

This invention is smart clothing with converging/diverging bend or stretch sensors for measuring body motion and/or configuration. Such smart clothing can be particularly useful for measuring twisting and/or rotational motion of complex joints such as shoulders and hips. It can be used for athletic training, sports performance analysis, sports motion capture, and fan engagement. It can be used for training and motion capture for: sports which involve extensive and/or complex lower-body motion (such as soccer, bicycling, and running) which are not well measured by single-location (wrist-worn) accelerometers; and also for sports which involve complex upper-body motion (such as golf, basketball, tennis, baseball, Frisbee[™], bogus ball, and fencing) which are not well measured by single-location accelerometers.

Such smart clothing can also be used for health, fitness, and medical applications. It can be used for caloric expenditure measurement, energy balance management, weight management, and caloric intake monitoring applications. It can be used for virtual exercise. It can be used for real-time avoidance of repeated motion injuries, injuries due to poor posture, and stress-related injuries including back injuries and carpal tunnel syndrome. It can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, osculation assessment, respiratory function assessment, plethysmography, cardiac function monitoring, orthopedic therapy, physical therapy, orthotic design and fitting, and pronation analysis. It can be used for telemedicine and/or telesurgery applications.

Such smart clothing can also be used for entertainment, gaming, and artistic purposes. It can be used for animation of an avatar in virtual reality and/or computer gaming. It can be used for animation of an animated character in motion picture making or other visual animation applications. It can be used for dance instruction, dance performance, funky chicken, and other performance art applications. It can be used for instruction and motion capture for playing musical instruments.

Such smart clothing can also be used for communication and computer interface purposes. It can be used for telepresence, teleconferencing, telecommunication, avatar animation, and virtual commerce. It can be used as part of a gesture recognition human-to-computer user interface. This invention be can be used for telerobotics to enable remote control of the actions of a robot.

REVIEW AND CATEGORIZATION OF THE PRIOR ART

There are motion capture technologies in the prior art, but they have limitations compared to this invention. As an example of prior art technology, there are camera-based motion capture systems. Some of these camera-based motion capture systems are very complex, comprising a circle of multiple cameras which each track a moving individual from a different perspective. These multi-camera systems can be accurate, but they also constrain a person to a space comprising the intersection of the fields of vision of these cameras. In addition to being relatively immobile, these multi-camera systems can also be relatively expensive.

There are also single-camera motion capture systems which are designed for home use. Some relatively-simple and reasonably-priced single-camera systems are used for home computer gaming, exercise routines, and other applications. However, these single-camera motion capture systems also restrict a person to remain in the field of vision of the camera. They are not mobile for outdoor activities such as golf or running or swimming. Further, relying on one camera (or even two cameras which are close together) means that the system cannot track the locations of body members when the camera's direct line of sight to them is obscured by other body members or objects.

As another example of prior art technology, there are complex full-body portable motion capture suits comprising a relatively-large number of accelerometers and gyroscopes. However, the more-accurate versions of such full-body motion capture suits tend to be relatively cumbersome and expensive. They can be great for motion capture for specialized purposes such as creating a video game or performance art, but are not well suited for contact sports or sports that involve extensive locational movement.

As another example of prior art technology, there is growing use of inertial sensors in wearable devices. These devices tend to be much less expensive and less intrusive than either the complex camera-based motion capture systems or the sophisticated full-body motion capture suits. They can perform adequately for measuring generalized "activity level", but they are not well-suited for capturing complex full-body motion such as that which occurs in sports like golf or gymnastics. Due to the limitations of camera-based systems, cumbersome full-body motion capture suits, and single-location accelerometer devices in the prior art, there remains a need for a wearable, mobile, reasonably-priced, and relatively-unobtrusive full-body motion-capture system which can be used in diverse environments.

It can be challenging trying to classify prior art in this field into discrete categories. However, classification of the prior art into categories, even if imperfect, can be an invaluable part of reviewing the prior art. Towards this end, I herein identify and briefly discuss 10 categories of prior art related to measurement and modeling of body motion, posture, and/or configuration. For the most relevant categories of prior art, I also provide specific examples of prior art (including patent or patent application number, inventor, publication date, and title). Some examples of prior art disclose multiple concepts and thus appear in more than one category. I hope that the reader finds this review and categorization of the prior art to be useful. The 10 categories of art used for this review and categorization are as follows: (1) wearable GPS for tracking geographic position; (2) fixed-location camera-based motion capture; (3) hand-held game controller, ball, bat, or other held object; (4) wearable RFID or other electromagnetic energy emitters; (5) wearable electromyographic (EMG) sensors; (6) rigid or partially-rigid exoskeleton; (7) wearable inertial sensors; (8) wearable pressure sensors; (9) wearable electromagnetic energy bend sensors and/or electrogoniometers; (10) wearable light energy bend sensors.

1. Wearable GPS for Tracking Geographic Position

Prior art in this category uses a wearable GPS unit to track a person's geographic position and macroscale body movement. Such art can be very useful for tracking movement distance and speed, but is not useful for mobile three-dimensional recognition of body motion, posture, and/or configuration and is less relevant to the technology of this present invention. Accordingly, although the category is mentioned here, specific examples of this large category of art are not listed.

2. Fixed-Location Camera-Based Motion Capture

Prior art in this widely-used category, traditionally known as "motion capture" or "mocap," uses one or more fixed-location cameras to take and analyze images of a person in order to estimate and/or model the person's movement. Such motion capture systems are widely used for animation in motion pictures and video games, using full-body motion for controlling a video game or other computer application, fixed-location sport-related motion analysis, medical body motion diagnostic assessment, and other applications. Such art can be very useful for all of these purposes, but is generally constrains a person to a fixed location and is subject to occlusion when a direct line of sight from the camera to a portion of a person's body is blocked. Accordingly, such art is less useful for mobile, ambulatory, and/or long-duration applications and is less relevant to the technology of this present invention. Thus, although the category is mentioned here, specific examples of art in this large category of prior art are not listed.

3. Hand-Held Game Controller, Ball, Bat, or Other Held Object

Prior art in this widely-used category tracks the location, orientation, and/or configuration of a hand-held game controller, sports ball, bat, club, or other held object in order to analyze the motion dynamics of a particular activity (such as a sport activity), control a computer game, interact with a virtual reality environment, or other motion-related application. Such art can be very useful for these purposes, but since the tracked object is not worn and be only in limited contact with the user's body, it is limited for tracking three-dimensional body motion, posture, and/or configuration. Accordingly, such art is less relevant to this present invention. This category is mentioned here, but specific examples of art in this category are not listed.

4. Wearable RFID or Other Electromagnetic Energy Emitters

Prior art in this category uses an array of wearable RFID or other electromagnetic energy emitters to track body motion and/or configuration in a three-dimensional space. Since this art generally constrains the user to motion within a defined space with fixed-location energy sensors, it is generally subject to similar location constraints as traditional camera-based motion capture. The technology is quite different than that used in the present invention and thus, although the category is mentioned here, specific examples of art in this category are not listed.

5. Wearable ElectroMyoGraphic (EMG) Sensors

Prior art in this category uses wearable sensors to measure electromagnetic energy which is naturally emitted from body muscles and nerves in order to estimate and model body motion. This category of prior art is relatively new and there are few examples in it as compared to the previous categories, but it is growing. Art in this category has the potential to eventually be very useful for mobile three-dimensional recognition of body motion, posture, and configuration. However, the technology is different than the technology used in this present invention. Unlike this present invention, EMG sensors measure naturally emitted electromagnetic energy and thus are less relevant to this present invention. Accordingly, this category is mentioned here, but specific examples of art in this category are not listed.

6. Rigid or Partially-Rigid Exoskeleton

Prior art in this category uses a rigid or partially-rigid exoskeleton which is attached to a person in order to measure and/or affect the person's body motion. Some exoskeletons are used primarily for measuring and modeling body motion. Other exoskeletons are used primarily for affecting body motion, such as with actuators which provide haptic feedback or help the person to move. This present invention focuses on flexible wearable pathways (which can be incorporated into an article of clothing) rather than a rigid or semi-rigid exoskeleton which is attached to a person. This rigid or semi-rigid nature of an exoskeleton can limit the range of body motion and limit its use for long-duration applications. Nonetheless, this category of art is more relevant than the previous categories and thus specific examples of art in this category are now listed.

Examples of prior art which appear to be within this category include the following U.S. Pat. Nos.: 5,012,819 (Marras et al., May 7, 1991, "Apparatus for Monitoring the Motion Components of the Spine"); 5,280,265 (Kramer et al., Jan. 18, 1994, "Strain-Sensing Goniometers, Systems and Recognition Algorithms"); 5,442,729 (Kramer et al., Aug. 15, 1995, "Strain-Sensing Goniometers, Systems and Recognition Algorithms"); 5,474,088 (Zaharkin et al., Dec. 12, 1995, "Device for Measuring Motion Characteristics of a Human Joint"); 5,516,249 (Brimhall, May 14, 1996, "Exoskeleton with Kinesthetic Feedback and Robotic Control"); 5,656,904 (Lander, Aug. 12, 1997, "Movement Monitoring and Control Apparatus for Body Members"); 5,676,157 (Kramer, Oct. 14, 1997, "Determination of Kinematically Constrained Multi-Articulated Structures"); 5,813,406 (Kramer et al., Sep. 29, 1998, "Strain-Sensing Goniometers, Systems and Recognition Algorithms"); 5,915,673 (Kazerooni, Jun. 29, 1999, "Pneumatic Human Power Amplifer Module"); 5,930,741 (Kramer, Jul. 27, 1999, "Accurate, Rapid, Reliable Position Sensing using Multiple Sensing Technologies"); and 5,961,541 (Ferrati, Oct. 5, 1999, "Orthopedic Apparatus for Walking and Rehabilitating Disabled Persons Including Tetraplegic Persons and for Facilitating and Stimulating the Revival of Comatose Patients Through the Use of Electronic and Virtual Reality Units").

Examples of prior art in this category also include U.S. Pat Nos.: 6,005,548 (Latypov et al., Dec. 21, 1999, "Method for Tracking and Displaying User's Spatial Position and Orientation, a Method for Representing Virtual Reality for a User, and Systems of Embodiment of Such Methods"); 6,035,274 (Kramer et al., Mar. 7, 2000, "Strain-Sensing Goniometers, Systems and Recognition Algorithms"); 6,042,555 (Kramer et al., Mar. 28, 2000, "Force-Feedback Interface Device for the Hand"); 6,050,962 (Kramer et al., Apr. 18, 2000, "Goniometer-Based Body-Tracking Device and Method"); 6,104,379 (Petrich et al., Aug. 15, 2000, "Forearm-Supported Exoskeleton Hand-Tracking Device"); 6,110,130 (Kramer, Aug. 29, 2000, "Exoskeleton Device for Directly Measuring Fingertip Position and Inferring Finger Joint Angle"); 6,162,190 (Kramer, Dec. 19, 2000, "Determination of Kinematically Constrained Multi-Articulated Structures"); 6,239,784 (Holmes, May 29, 2001, "Exo-Skeletal Haptic Computer Human/Computer Interface Device"); 6,246,390 (Rosenberg, Jun. 12, 2001, "Multiple Degree-of-Freedom Mechanical Interface to a Computer System"); 6,413,229 (Kramer et al., Jul. 2, 2002, "Force-Feedback Interface Device for the Hand"); and 6,428,490 (Kramer et al., Aug. 6, 2002, "Goniometer-Based Body-Tracking Device and Method").

Examples of prior art in this category also include U.S. Pat Nos.: 6,497,672 (Kramer, Dec. 24, 2002, "Device and Method for Measuring the Position of Animate Links"); 6,666,831 (Edgerton et al., Dec. 23, 2003, "Method, Apparatus and System for Automation of Body Weight Support Training (BWST) of Biped Locomotion Over a Treadmill Using a Programmable Stepper Device (PSD) Operating Like an Exoskeleton Drive System from a Fixed Base"); 6,701,296 (Kramer et al., Mar. 2, 2004, "Strain-Sensing Goniometers, Systems, and Recognition Algorithms"); 6,866,643 (Kramer, Mar. 15, 2005, "Determination of Finger Position"); 6,890,312 (Priester et al., May 10, 2005, "Joint Angle Indication System"); 7,070,571 (Kramer et al., Jul. 4, 2006, "Goniometer-Based Body-Tracking Device"); 7,153,242 (Goffer, Dec. 26, 2006, "Gait-Locomotor Apparatus"); 7,410,338 (Schiele et al., Aug. 12, 2008, "Exoskeleton for the Human Arm, in Particular for Space Applications"); 7, 500, 853 (Bevirt et al., Mar. 10, 2009, "Mechanical Interface for a Computer System"); 7,899,556 (Nathan et al., Mar. 1, 2011, "Orthosis for a Gait Modulation System"); 8,055,021 (Caritu et al., Nov. 8, 2011, "Motion Capture Device and Associated Method"); 8,171,570 (Adarraga, May 8, 2012, "Exoskeleton"); 8,678,979 (Stark et al., Mar. 25, 2014, "Remote Monitoring of a Patient"); 8,708,825 (Crisco, Apr. 29, 2014, "Device Controller with Conformable Fitting System"); and 8,777,878 (Deitz, Jul. 15, 2014, "Devices, Systems, and Methods for Measuring and Evaluating the Motion and Function of Joints and Associated Muscles").

Examples of prior art which appear to be within this category include the following U.S. patent applications: 20010003712 (Roelofs, Jun. 14, 2001, "Exoskeletal Platform for Controlling Multi-Directional Avatar Kinetics in a Virtual Environment"); 20010020140 (Kramer, Sep. 6, 2001, "Device and Method for Measuring the Position of Animate Links"); 20020198472 (Kramer, Dec. 26, 2002, "Determination of Finger Position"); 20030083596 (Kramer et al., May 1, 2003, "Goniometer-Based Body-Tracking Device and Method"); 20030091966 (Collodi, May 15, 2003, "Excercise/Simulation Device"); 20060130347 (Bergamasco et al., Jun. 22, 2006, "Device for Gioniometric Measurements"); 20060167564 (Flaherty et al., Jul. 27, 2006, "Limb and Digit Movement System"); 20060189899 (Flaherty et al., Aug. 24, 2006, "Joint Movement Apparatus"); 20060217233 (Lee, Sep. 28, 2006, "Apparatus and Method for Lower-Limb Rehabilitation Training Using Weight Load and Joint Angle as Variables"); 20060240953 (Shahinpoor, Oct. 26, 2006, "Human Lower Limb Performance Enhancement Outfit"); 20070123997 (Herr et al., May 31, 2007, "Exoskeletons for Running and Walking"); 20070132722 (Kim et al., Jun. 14, 2007, "Hand Interface Glove Using Miniaturized Absolute Position Sensors and Hand Interface System Using the Same"); 20110040216 (Herr et al., Feb. 17, 2011, "Exoskeletons for Running and Walking"); 20130158444 (Herr et al., Jun. 20, 2013, "Robotic System for Simulating a Wearable Device and Method of Use"); 20130204435 (Moon et al., Aug. 8, 2013, "Wearable Robot and Teaching Method of Motion using the Same"); and 20140366675 (Gosselin et al., Dec. 18, 2014, "Articulated Limb for a Robot or Haptic Interface and Robot and Haptic Interface Comprising at Least One Such Articulated Limb").

7. Wearable Inertial Sensors

Prior art in this category uses one or more wearable inertial sensors (such as accelerometers or gyroscopes) to estimate and/or model body motion, posture, and/or configuration. With reductions in the cost and size of inertial sensors, they are now being incorporated into a wide array of wearable devices. Currently, devices in this category most commonly include one or more inertial sensors at a single location on a person's body, wherein movement of the body at that location is used to estimate overall level of activity or infer overall patterns of body motion, posture, and/or configuration. However, there is a growing body of art which uses an array of inertial sensors worn at different locations on a person's body to measure and/or model three-dimensional body motion, posture, and/or configuration. The data processing demands of estimating three-dimensional body motion using a large array of wearable inertial sensors can be challenging, but there is a lot of progress being made in this area. The motion capture technology of this present invention is different than that used in this category, but this category of art is relevant and thus specific examples of art in this category are now listed.

Examples of prior art which appear to be within this category include the following U.S. Pat Nos.: 5,337,758 (Moore et al., Aug. 16, 1994, "Spine Motion Analyzer and Method"); 5,375,610 (LaCourse et al., Dec. 27, 1994, "Apparatus for the Functional Assessment of Human Activity"); 5,592,401 (Kramer, Jan. 7, 1997, "Accurate, Rapid, Reliable Position Sensing using Multiple Sensing Technologies"); 5,615,132 (Horton et al., Mar. 25, 1997, "Method and Apparatus for Determining Position and Orientation of a Moveable Object Using Accelerometers"); 5,819,206 (Horton et al., Oct. 6, 1998, "Method and Apparatus for Determining Position and Orientation of a Moveable Object Using Accelerometers"); 6,018,705 (Gaudet et al., Jan. 25, 2000, "Measuring Foot Contact Time and Foot Loft Time of a Person in Locomotion"); 6,032,530 (Hock, Mar. 7, 2000, "Biofeedback System for Sensing Body Motion and Flexure"); 6,059,576 (Brann, May 9, 2000, "Training and Safety Device, System and Method to Aid in Proper Movement During Physical Activity"); 6,095,991 (Krausman et al., Aug. 1, 2000, "Ambulatory Body Position Monitor"); 6,148,280 (Kramer, Nov. 14, 2000, "Accurate, Rapid, Reliable Position Sensing using Multiple Sensing Technologies"); 6,162,191 (Foxlin, Dec. 19, 2000, "Inertial Orientation Tracker Having Automatic Drift Compensation for Tracking Human Head and Other Similarly Sized Body"); 6,210,301 (Abraham-Fuchs et al., Apr. 3, 2001, "Patient Monitoring System"); and 6,304,840 (Vance et al., Oct. 16, 2001, "Fingerless Glove for Interacting with Data Processing System").

Examples of prior art in this category also include U.S. Pat. Nos.: 6,361,507 (Foxlin, Mar. 26, 2002, "Inertial Orientation Tracker Having Gradual Automatic Drift Compensation for Tracking Human Head and Other Similarly Sized Body"); 6,409,687 (Foxlin, Jun. 25, 2002, "Motion Tracking System"); 6,466,200 (Anton et al., Oct. 15, 2002, "Computer Input Device"); 6,513,532 (Malik et al., Feb. 4, 2003, "Diet and Activity Monitoring Device"); 6,611,141 (Schulz et al., Aug. 26, 2003, "Hybrid 3-D Probe Tracked by Multiple Sensor"); 6,691,074 (Moriya et al., Feb. 10, 2004, "System for Three Dimensional Positioning and Tracking"); 6,700,499 (Kubo et al., Mar. 2, 2004, "Body Motion Detector"); 6,703,939 (Lehrman et al., Mar. 9, 2004, "System and Method for Detecting Motion of a Body"); 6,731,268 (Anton et al., May 4, 2004, "Computer Input Device"); 6,786,877 (Foxlin, Sep. 7, 2004, "Inertial Orientation Tracker Having Automatic Drift Compensation using an at Rest Sensor for Tracking Parts of a Human Body"); 6,834,436 (Townsend et al., Dec. 28, 2004, "Posture and Body Movement Measuring System"); 6,836,744 (Asphahani et al., Dec. 28, 2004, "Portable System for Analyzing Human Gait"); 6,864,796 (Lehrman et al., Mar. 8, 2005, "Systems Within a Communication Device for Evaluating Movement of a Body and Methods of Operating the Same"); 6,871,413 (Arms et al., Mar. 29, 2005, "Miniaturized Inclinometer for Angle Measurement with Accurate Measurement Indicator"); 6,912,475 (Moriya et al., Jun. 28, 2005, "System for Three Dimensional Positioning and Tracking"); 6,985,134 (Suprun et al., Jan. 10, 2006, "Computer Input Device"); and 7,020,508 (Stivoric et al., Mar. 28, 2006, "Apparatus for Detecting Human Physiological and Contextual Information").

Examples of prior art in this category also include U.S. Pat Nos.: 7,028,547 (Shiratori et al., Apr. 18, 2006, "Body Motion Detector"); 7,095,331 (Lehrman et al, Aug. 22, 2006, "System and Method for Detecting Motion of a Body"); 7,141,026 (Aminian et al., Nov. 28, 2006, "Body Movement Monitoring System and Method"); 7,145,461 (Lehrman et al., Dec. 5, 2006, "System and Method for Analyzing Activity of a Body"); 7,149,584 (Koh et al., Dec. 12, 2006, "System and Method for Determining Patient Posture Based on 3-D Trajectory using an Implantable Medical Device"); 7,167,743 (Heruth et al., Jan. 23, 2007, "Collecting Activity Information to Evaluate Therapy"); 7,191,652 (Pristup et al., Mar. 20, 2007, "Magnetofluidic Accelerometer with Partial Filling of Cavity with Magnetic Fluid"); 7,210,240 (Townsend et al., May 1, 2007, "Posture and Body Movement Measuring System"); 7,212,943 (Aoshima et al., May 1, 2007, "Body Motion Detection Device, Pitch Meter, Wristwatch-Type Information Processing Device, Method for Controlling Thereof, Control Program, and Storage Medium"); and 7,219,033 (Kolen, May 15, 2007, "Single/Multiple Axes Six Degrees of Freedom (6 DOF) Inertial motion capture System with Initial Orientation Determination Capability").

Examples of prior art in this category also include U.S. Pat Nos.: 7,261,690 (Teller et al., Aug. 28, 2007, "Apparatus for Monitoring Health, Wellness and Fitness"); 7,264,554 (Bentley, Sep. 4, 2007, "Method and System for Athletic Motion Analysis and Instruction"); 7,285,090 (Stivoric et al., Oct. 23, 2007, "Apparatus for Detecting, Receiving, Deriving and Displaying Human Physiological and Contextual Information"); 7,292,151 (Ferguson et al., Nov. 6, 2007, "Human Movement Measurement System"); 7,292,223 (Suprun et al., Nov. 6, 2007, "Location Tracking Device"); 7,295,184 (Suprun et al., Nov. 13, 2007, "Computer Input Device"); 7,296,469 (Simonenko et al., Nov. 20, 2007, "Magnetofluidic Accelerometer with Active Suspension"); 7,313,440 (Miesel, Dec. 25, 2007, "Collecting Posture and Activity Information to Evaluate Therapy"); 7,330,760 (Heruth et al., Feb. 12, 2008, "Collecting Posture Information to Evaluate Therapy"); 7,383,728 (Noble et al., Jun. 10, 2008, "Orientation and Motion Sensing in Athletic Training Systems, Physical Rehabilitation and Evaluation Systems, and Hand-Held Devices"); 7,394,385 (Franco et al., Jul. 1, 2008, "Comprehensive Monitoring System"); 7,395,113 (Heruth et al., Jul. 1, 2008, "Collecting Activity Information to Evaluate Therapy"); 7,395,181 (Foxlin, Jul. 1, 2008, "Motion Tracking System"); 7,421,369 (Clarkson, Sep. 2, 2008, "Activity Recognition Apparatus, Method and Program"); 7,447,545 (Heruth et al., Nov. 4, 2008, "Collecting Posture Information to Evaluate Therapy"); 7,450,002 (Choi et al., Nov. 11, 2008, "Method and Apparatus for Monitoring Human Activity Pattern"); and 7,451,056 (Flentov et al., Nov. 11, 2008, "Activity Monitoring Systems and Methods").

Examples of prior art in this category also include U.S. Pat. Nos.: 7,471,290 (Wang et al., Dec. 30, 2008, "Posture Detection System"); 7,479,890 (Lehrman et al., Jan. 20, 2009, "System and Method for Analyzing Activity of a Body"); 7,487,043 (Adams, Feb. 3, 2009, "Relative Positioning System"); 7,492,268 (Ferguson et al., Feb. 17, 2009, "Human Movement Measurement System"); 7,512,515 (Vock et al., Mar. 31, 2009, "Activity Monitoring Systems and Methods"); 7,565,295 (Hernandez-Rebollar, Jul. 21, 2009, "Method and Apparatus for Translating Hand Gestures"); 7,602,301 (Stirling et al., Oct. 13, 2009, "Apparatus, Systems, and Methods for Gathering and Processing Biometric and Biomechanical Data"); 7,602,310 (Mann et al., Oct. 13, 2009, "Telemetered Characteristic Monitor System and Method of using the Same"); 7,627,451 (Vock et al., Dec. 1, 2009, "Movement and Event Systems and Associated Methods"); 7,634,379 (Noble, Dec. 15, 2009, "Newtonian Physical Activity Monitor"); 7,647,196 (Kahn et al., Jan. 12, 2010, "Human Activity Monitoring Device with Distance Calculation"); 7,653,214 (Schroeder et al., Jan. 26, 2010, "Accelerometer Utilizing Image-Based Movement Tracking"); 7,653,508 (Kahn et al., Jan. 26, 2010, "Human Activity Monitoring Device"); and 7,661,200 (Bonnet et al., Feb. 16, 2010, "Method and Device for Determining a Person's Motions").

Examples of prior art in this category also include U.S. Pat Nos.: 7,668,588 (Kovacs, Feb. 23, 2010, "Dual-Mode Physiologic Monitoring Systems and Methods"); 7,672,781 (Churchill et al., Mar. 2, 2010, "Miniaturized Wireless Inertial Sensing System"); 7,689,378 (Kolen, Mar. 30, 2010, "Motion Sensing Apparatus, Systems and Techniques"); 7,698,101 (Alten et al., Apr. 13, 2010, "Smart Garment"); 7,698,830 (Townsend et al., Apr. 20, 2010, "Posture and Body Movement Measuring System"); 7,725,279 (Luinge et al., May 25, 2010, "System and a Method for Motion Tracking using a Calibration Unit"); 7,742,894 (Chen et al., Jun. 22, 2010, "Multi-Person Pose Recognition System Using a Zigbee Wireless Sensor Network"); 7753861 (Kahn et al., Jul. 13, 2010, "Chest Strap Having Human Activity Monitoring Device"); 7,792,583 (Miesel et al., Sep. 7, 2010, "Collecting Posture Information to Evaluate Therapy"); 7,805,196 (Miesel et al., Sep. 28, 2010, "Collecting Activity Information to Evaluate Therapy"); 7,811,333 (Jonsson et al., Oct. 12, 2010, "Systems and Methods for Processing Limb Motion"); 7,821,407 (Shears et al., Oct. 26, 2010, "Apparatus, Systems, and Methods for Gathering and Processing Biometric and Biomechanical Data"); 7,825,815 (Shears et al., Nov. 2, 2010, "Apparatus, Systems, and Methods for Gathering and Processing Biometric and Biomechanical Data"); 7,827,000 (Stirling et al., Nov. 2, 2010, "Method and Apparatus for Estimating a Motion Parameter"); 7,845,228 (Bremer et al., Dec. 7, 2010, "Activity Monitoring"); 7,881,902 (Kahn et al., Feb. 1, 2011, "Human Activity Monitoring Device"); 7,952,483 (Ferguson et al., May 31, 2011, "Human Movement Measurement System"); and 7,978,081 (Shears et al., Jul. 12, 2011, "Apparatus, Systems, and Methods for Communicating Biometric and Biomechanical Information").

Examples of prior art in this category also include U.S. Pat. Nos.: 7,981,058 (Akay, Jul. 19, 2011, "Intelligent Wearable Monitor Systems and Methods"); 8,010,308 (Churchill, Aug. 30, 2011, "Inertial Measurement System with Self Correction"); 8,025,632 (Einarsson, Sep. 27, 2011, "Wearable Device Having Feedback Characteristics"); 8,036,850 (Kulach et al., Oct. 11, 2011, "Method and Apparatus for Estimating a Motion Parameter"); 8,036,851 (Vock et al., Oct. 11, 2011, "Activity Monitoring Systems and Methods"); 8,060,337 (Kulach et al., Nov. 15, 2011, "Method and Apparatus for Estimating a Motion Parameter"); 8,073,707 (Teller et al., Dec. 6, 2011, "System for Detecting Monitoring and Reporting an Individual's Physiological or Contextual Status"); 8,075,499 (Nathan et al., Dec. 13, 2011, "Abnormal Motion Detector and Monitor"); 8,099,258 (Alten et al., Jan. 17, 2012, "Smart Garment"); 8,125,448 (Ranta et al., Feb. 28, 2012, "Wearable Computer Pointing Device"); 8,135,473 (Miesel et al., Mar. 13, 2012, "Collecting Posture and Activity Information to Evaluate Therapy"); 8,140,339 (Hernandez-Rebollar, Mar. 20, 2012, "Method and Apparatus for Translating Hand Gestures"); and 8,150,531 (Skelton, Apr. 3, 2012, "Associating Therapy Adjustments with Patient Posture States").

Examples of prior art in this category also include U.S. Pat. Nos.: 8,152,694 (Srinivasan et al., Apr. 10, 2012, "Activity Monitoring Device and Method"); 8,157,730 (Leboeuf et al., Apr. 17, 2012, "Physiological and Environmental Monitoring Systems and Methods"); 8,157,731 (Teller et al., Apr. 17, 2012, "Method and Apparatus for Auto Journaling of Continuous or Discrete Body States Utilizing Physiological and/or Contextual Parameters"); 8,159,354

(Ferguson et al., Apr. 17, 2012, "Human Movement Measurement System"); 8,162,857 (Lanfermann et al., Apr. 24, 2012, "Limb Movement Monitoring System"); 8,165,840 (Hatlestad et al., Apr. 24, 2012, "Posture Sensor Automatic Calibration"); 8,165,844 (Luinge et al., Apr. 24, 2012, "Motion Tracking System"); 8,175,720 (Skelton et al., May 8, 2012, "Posture-Responsive Therapy Control Based on Patient Input"); 8,180,591 (Yuen et al., May 15, 2012, "Portable Monitoring Devices and Methods of Operating Same"); 8,180,592 (Yuen et al., May 15, 2012, "Portable Monitoring Devices and Methods of Operating Same"); 8,187,182 (Kahn et al., May 29, 2012, "Sensor Fusion for Activity Identification"); 8,200,340 (Skelton et al., Jun. 12, 2012, "Guided Programming for Posture-State Responsive Therapy"); and 8,203,487 (Hol et al., Jun. 19, 2012, "Tightly Coupled UWB/IMU Pose Estimation System and Method").

Examples of prior art in this category also include U.S. Pat. Nos.: 8,206,325 (Najafi et al., Jun. 26, 2012, "Ambulatory System for Measuring and Monitoring Physical Activity and Risk of Falling and for Automatic Fall Detection"); 8,209,028 (Skelton et al., Jun. 26, 2012, "Objectification of Posture State-Responsive Therapy Based on Patient Therapy Adjustments"); 8,209,147 (Solinsky, Jun. 26, 2012, "Geolocation System and Method for Determining Mammal Locomotion Movement"); 8,219,206 (Skelton et al., Jul. 10, 2012, "Dwell Time Adjustments for Posture State-Responsive Therapy"); 8,231,555 (Skelton et al., Jul. 31, 2012, "Therapy System Including Multiple Posture Sensor"); 8,249,718 (Skelton et al., Aug. 26, 2012, "Programming Posture State-Responsive Therapy with Nominal Therapy Parameters"); 8,275,635 (Stivoric et al., Sep. 25, 2012, "Integration of Lifeotypes with Devices and Systems"); 8,280,517 (Skelton et al., Oct. 2, 2012, "Automatic Validation Techniques for Validating Operation of Medical Devices"); 8,282,580 (Skelton et al., Oct. 9, 2012, "Data Rejection for Posture State Analysis"); 8,284,847 (Adermann, Oct. 9, 2012, "Detecting Motion for a Multifunction Sensor Device"); 8,301,575 (Bonnet et al., Oct. 30, 2012, "Method and Device for the Recognition of the Position or Movement of a Device or a Person"); 8,311,769 (Yuen et al., Nov. 15, 2012, "Portable Monitoring Devices and Methods of Operating Same"); and 8,311,770 (Yuen et al., Nov. 15, 2012, "Portable Monitoring Devices and Methods of Operating Same").

Examples of prior art in this category also include U.S. Pat. Nos.: 8,315,710 (Skelton et al., Nov. 20, 2012, "Associating Therapy Adjustments with Patient Posture States"); 8,323,218 (Davis et al., Dec. 4, 2012, "Generation of Proportional Posture Information Over Multiple Time Intervals"); 8,328,718 (Tran, Dec. 11, 2012, "Health Monitoring Appliance"); 8,332,041 (Skelton et al., Dec. 11, 2012, "Patient Interaction with Posture-Responsive Therapy"); 8,342,045 (Maxwell et al., Jan. 1, 2013, "Activity Monitor"); 8,352,211 (Vock et al., Jan. 8, 2013, "Activity Monitoring Systems and Methods"); 8,366,641 (Wang et al., Feb. 5, 2013, "Posture Detector Calibration and Use"); 8,382,590 (Stivoric et al., Feb. 26, 2013, "Entertainment, Gaming and Interactive Spaces Based on Lifeotypes"); 8,384,551 (Ross et al., Feb. 26, 2013, "Sensor Device and Method for Monitoring Physical Stresses Placed on a User"); 8,386,008 (Yuen et al., Feb. 26, 2013, "Activity Monitoring Systems and Methods of Operating Same"); 8,388,555 (Panken et al., Mar. 5, 2013, "Posture State Classification for a Medical Device"); 8,396,554 (Miesel et al., Mar. 12, 2013, "Collecting Posture Information to Evaluate Therapy"); 8,396,565 (Singhal et al., Mar. 12, 2013, "Automatic Therapy Adjustments"); 8,397,568 (Cardarelli, Mar. 19, 2013, "Bias Measurement for MEMS Gyroscopes and Accelerometers"); and 8,401,666 (Skelton et al., Mar. 19, 2013, "Modification Profiles for Posture-Responsive Therapy").

Examples of prior art in this category also include U.S. Pat. Nos.: 8,414,507 (Asada, Apr. 9, 2013, "Body Motion Balance Detection Device, Body Motion Balance Detection Program, Body Motion Balance Detection Method, and Body Motion Balance Diagnosis Method"); 8,416,102 (Yin, Apr. 9, 2013, "Activity Monitoring System Insensitive to Accelerations Induced by External Motion Factors"); 8,421,854 (Zerkin, Apr. 16, 2013, "System and Method for Motion Capture"); 8,427,325 (Ferguson et al., Apr. 25, 2013, "Human Movement Measurement System"); 8,435,177 (Lanfermann et al., May 7, 2013, "Process and System for Monitoring Exercise Motions of a Person"); 8,436,737 (Trout, May 7, 2013, "Postural State Attitude Monitoring, Caution, and Warning Systems and Methods"); 8,437,824 (Moon et al., May 7, 2013, "Body-Worn Pulse Oximeter"); 8,437,861 (Skelton et al., May 7, 2013, "Posture State Redefinition Based on Posture Data and Therapy Adjustments"); 8,437,980 (Yuen et al., May 7, 2013, "Portable Monitoring Devices and Methods of Operating Same"); 8,446,275 (Utter, May 26, 2013, "General Health and Wellness Management Method and Apparatus for a Wellness Application Using Data from a Data-Capable Band"); and 8,447,401 (Miesel et al., May 26, 2013, "Collecting Posture Information to Evaluate Therapy").

Examples of prior art in this category also include U.S. Pat. Nos.: 8,447,411 (Skelton et al., May 26, 2013, "Patient Interaction with Posture-Responsive Therapy"); 8,460,197 (Brady et al., Jun. 11, 2013, "Monitoring Device with a Pedometer"); 8,463,573 (Flentov et al., Jun. 11, 2013, "Movement Monitoring Systems and Associated Methods"); 8,463,576 (Yuen et al., Jun. 11, 2013, "Portable Monitoring Devices and Methods of Operating Same"); 8,463,577 (Yuen et al., Jun. 11, 2013, "Portable Monitoring Devices and Methods of Operating Same"); 8,504,150 (Skelton, Aug. 6, 2013, "Associating Therapy Adjustments with Posture States using a Stability Timer"); 8,515,549 (Panken et al., Aug. 20, 2013, "Associating Therapy Adjustments with Intended Patient Posture States"); 8,515,550 (Skelton et al., Aug. 20, 2013, "Assignment of Therapy Parameter to Multiple Posture States"); 8,527,217 (Moodie, Sep. 3, 2013, "Apparatus and Method for Physical Evaluation"); 8,543,185 (Yuen et al., Sep. 24, 2013, "Activity Monitoring Systems and Methods of Operating Same"); 8,543,351 (Yuen et al., Sep. 24, 2013, "Portable Monitoring Devices and Methods of Operating Same"); 8,548,740 (Hesch et al., Oct. 6, 2013, "System and Method for Wavelet-Based Gait Classification"); 8,548,770 (Yuen et al., Oct. 6, 2013, "Portable Monitoring Devices and Methods of Operating Same"); 8,554,297 (Moon et al., Oct. 8, 2013, "Body-Worn Pulse Oximeter"); 8,579,834 (Davis et al., Nov. 12, 2013, "Display of Detected Patient Posture State"); 8,583,252 (Skelton et al., Nov. 12, 2013, "Patient Interaction with Posture-Responsive Therapy"); 8,583,402 (Yuen et al., Nov. 12, 2013, "Portable Monitoring Devices and Methods of Operating Same"); and 8,616,989 (Bentley, Dec. 31, 2013, "Method and System for Athletic Motion Analysis and Instruction").

Examples of prior art in this category also include U.S. Pat. Nos.: 8,643,494 (Trout, Feb. 4, 2014, "Postural State Attitude Monitoring, Caution, and Warning Systems and Methods"); 8,651,964 (Brick, Feb. 18, 2014, "Advanced Video Controller System"); 8,655,618 (Flaction et al., Feb. 18, 2014, "Accelerometer and Method for Controlling an Accelerometer"); 8,657,772 (Einarsson, Feb. 25, 2014, "Wearable Device Having Feedback Characteristics"); 8670953 (Yuen et al., Mar. 11, 2014, "Portable Monitoring Devices and Methods of Operating Same"); 8,708,904 (Stivoric et al., Apr. 29, 2014, "Device Utilizing Data of a User's Context or Activity to Determine the User's Caloric Consumption or Expenditure"); 8,712,723 (Kahn et al., Apr. 29, 2014, "Human Activity Monitoring Device"); 8,760,392 (Lloyd et al., Jun. 24, 2014, "Wireless Motion Processing Sensor Systems Suitable for Mobile and Battery Operation"); 8,764,651 (Tran, Jul. 6, 2014, "Fitness Monitoring"); 8,784,342 (Hyde et al., Jul. 22, 2014, "Shape Sensing Clothes to Inform the Wearer of a Condition"); 8,788,055 (Gerber et al., Jul. 22, 2014, "Multi-Location Posture Sensing"); 8,795,137 (Ellis et al., Aug. 5, 2014, "Position Tracking and Guidance Methods"); 8,818,748 (Hatlestad et al., Aug. 26, 2014, "Posture Sensor Automatic Calibration"); 8,821,417 (McGregor et al., Sep. 2, 2014, "Method of Monitoring Human Body Movement"); and 8,823,490 (Libbus et al., Sep. 2, 2014, "Patient Monitoring Systems and Methods").

Examples of prior art in this category also include U.S. Pat. Nos.: 8,849,610 (Molettiere et al., Sep. 30, 2014, "Tracking User Physical Activity With Multiple Devices"); 8876738 (Kahn et al., Nov. 4, 2014, "Human Activity Monitoring Device"); 8,905,948 (Davis et al., Dec. 9, 2014, "Generation of Proportional Posture Information over Multiple Time Intervals"); 8,909,543 (Tropper et al., Dec. 9, 2014, "Methods for Detecting and Recording Physical Activity of Person"); 8,928,484 (Chang et al., Jan. 6, 2015, "System and Method of Biomechanical Posture Detection and Feedback"); 8,929,966 (LeBoeuf et al., Jan. 6, 2015, "Physiological Monitoring Methods"); 8,944,939 (Clark et al., Feb. 3, 2015, "Inertial Measurement of Sports Motion"); 8,947,441 (Hodgins et al., Feb. 3, 2015, "System and Method for Database Driven Action Capture"); 8,949,070 (Kahn et al., Feb. 3, 2015, "Human Activity Monitoring Device with Activity Identification"); and 8,958,885 (Panken et al., Feb. 17, 2015, "Posture State Classification for a Medical Device").

Examples of prior art which appear to be within this category include the following U.S. patent applications: 20010049470 (Mault et al., Dec. 6, 2001, "Diet and Activity Monitoring Device"); 20030023192 (Foxlin, Jan. 30, 2003, "Inertial Orientation Tracker Having Automatic Drift Compensation using an at Rest Sensor for Tracking Parts of a Human Body"); 20030045816 (Foxlin, Mar. 6, 2003, "Motion Tracking System"); 20030047002 (Arms et al., Mar. 13, 2003, "MEMS Based Angular Accelerometer"); 20030120448 (Moriya et al., Jun. 26, 2003, "System for Three Dimensional Positioning and Tracking"); 20050126026 (Townsend et al., Jun. 16, 2005, "Posture and Body Movement Measuring System"); 20050140651 (Suprun et al., Jun. 30, 2005, "Computer Input Device"); 20060022833 (Ferguson et al., Feb. 2, 2006, "Human Movement Measurement System"); 20060059976 (Simonenko et al., Mar. 25, 2006, "Accelerometer with Real-Time Calibration"); 20060059988 (Pristup, Mar. 25, 2006, "Magnetofluidic Accelerometer with Non-Magnetic Film on Drive Magnets"); and 20060059990 (Simonenko et al., Mar. 25, 2006, "Magnetofluidic Accelerometer with Active Suspension").

Examples of prior art in this category also include U.S. patent applications: 20060059991 (Pristup et al., Mar. 25, 2006, "Magnetofluidic Accelerometer with Partial Filling of Cavity with Magnetic Fluid"); 20060070443 (Pristup, Apr. Jun. 2006, "Magnetofluidic Accelerometer with Capacitive Sensing of Inertial Body Position"); 20060135883 (Jonsson et al., Jun. 22, 2006, "Systems and Methods for Processing Limb Motion"); 20060166737 (Bentley, Jul. 27, 2006, "Method and System for Athletic Motion Analysis and Instruction"); 20060184336 (Kolen, Aug. 17, 2006, "Single/Multiple Axes Six Degrees of Freedom (6 DOF) Inertial motion capture System with Initial Orientation Determination Capability"); 20060212097 (Varadan et al., Sep. 26, 2006, "Method and Device for Treatment of Medical Conditions and Monitoring Physical Movements"); 20060241521 (Cohen, Oct. 26, 2006, "System for Automatic Structured Analysis of Body Activities"); 20060284979 (Clarkson, Dec. 26, 2006, "Activity Recognition Apparatus, Method and Program"); 20070000324 (Pristup et al., Jan. 4, 2007, "Magnetofluidic Accelerometer with Partial Filling of Cavity with Magnetic Fluid"); 20070038038 (Stivoric et al., Feb. 15, 2007, "Wearable Human Physiological and Environmental Data Sensors and Reporting System Therefor"); and 20070073482 (Churchill et al., Mar. 29, 2007, "Miniaturized Wireless Inertial Sensing System").

Examples of prior art in this category also include U.S. patent applications: 20070100666 (Stivoric et al., May 3, 2007, "Devices and Systems for Contextual and Physiological-Based Detection, Monitoring, Reporting, Entertainment, and Control of Other Devices"); 20070169364 (Townsend et al., Jul. 26, 2007, "Posture and Body Movement Measuring System"); 20070173705 (Teller et al., Jul. 26, 2007, "Apparatus for Monitoring Health, Wellness and Fitness"); 20070214889 (Pristup, Sep. 20, 2007, "Magnetofluidic Unidirectional Accelerometer"); 20070219744 (Kolen, Sep. 20, 2007, "Motion Sensing Apparatus, Systems and Techniques"); 20070270214 (Bentley, Nov. 22, 2007, "Method and System for Athletic Motion Analysis and Instruction"); 20080036737 (Hernandez-Rebollar, Feb. 14, 2008, "Arm Skeleton for Capturing Arm Position and Movement"); 20080061949 (Ferguson et al., Mar. 13, 2008, "Human Movement Measurement System"); 20080084385 (Ranta et al., Apr. 10, 2008, "Wearable Computer Pointing Device"); and 20080167535 (Andre et al., Jul. 10, 2008, "Devices and Systems for Contextual and Physiological-Based Reporting, Entertainment, Control of Other Devices, Health Assessment and Therapy").

Examples of prior art in this category also include U.S. patent applications: 20080285805 (Luinge et al., Nov. 20, 2008, "Motion Tracking System"); 20090030345 (Bonnet et al., Jan. 29, 2009, "Method and Device for the Recognition of the Position or Movement of a Device or a Person"); 20090149257 (Ferguson et al., Jun. 11, 2009, "Human Movement Measurement System"); 20090171180 (Pering et al., Jul. 2, 2009, "Method and Apparatus for Configuring Wearable Sensor"); 20090204031 (McNames et al., Aug. 13, 2009, "Joint Angle Tracking with Inertial Sensor"); 20090278791 (Slycke et al., Nov. 12, 2009, "Motion Tracking System"); 20100026809 (Curry, Feb. 4, 2010, "Camera-Based Tracking and Position Determination for Sporting Events"); 20100036288 (Lanfermann et al., Feb. 11, 2010, "Limb Movement Monitoring System"); 20100076348 (McNames et al., Mar. 25, 2010, "Complete Integrated System for Continuous Monitoring and Analysis of Movement Disorders"); 20100176952 (Bajcsy et al., Jul. 15, 2010, "System for Detection of Body Motion"); 20100211349 (Flaction et al., Aug. 19, 2010, "Accelerometer and Method for Controlling an Accelerometer"); and 20100225473 (Leuthardt et al., Sep. 9, 2010, "Postural Information System and Method").

Examples of prior art in this category also include U.S. patent applications: 20100225474 (Leuthardt et al., Sep. 9, 2010, "Postural Information System and Method");

20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); and 20100228488 (Leuthardt et al., Sep. 9, 2010, "Postural Information System and Method"); 20100228489 (Leuthardt et al., Sep. 9, 2010, "Postural Information System and Method").

Examples of prior art in this category also include U.S. patent applications: 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); 20100309209 (Hodgins et al., Dec. 9, 2010, "System and Method for Database Driven Action Capture"); 20100324384 (Moon et al., Dec. 25, 2010, "Body-Worn Pulse Oximeter"); 20100324385 (Moon et al., Dec. 25, 2010, "Body-Worn Pulse Oximeter"); and 20100324386 (Moon et al., Dec. 25, 2010, "Body-Worn Pulse Oximeter").

Examples of prior art in this category also include U.S. patent applications: 20100324387 (Moon et al., Dec. 25, 2010, "Body-Worn Pulse Oximeter"); 20100324388 (Moon et al., Dec. 25, 2010, "Body-Worn Pulse Oximeter"); 20100324389 (Moon et al., Dec. 25, 2010, "Body-Worn Pulse Oximeter"); 20100324456 (Jonsson et al., Dec. 25, 2010, "Systems and Methods for Processing Limb Motion"); 20110025562 (Hol et al., Feb. 3, 2011, "Tightly Coupled UWB/IMU Pose Estimation System and Method"); 20110028865 (Luinge et al., Feb. 3, 2011, "Inertial Sensor Kinematic Coupling"); 20110046915 (Hol et al., Feb. 24, 2011, "Use of Positioning Aiding System for Inertial Motion Capture"); 20110181422 (Tran, Jul. 28, 2011, "Personal Emergency Response (PER) System"); 20110201428 (Ferguson et al., Aug. 18, 2011, "Human Movement Measurement System"); 20110313705 (Esser et al., Dec. 22, 2011, "Gait Monitor"); 20120046901 (Green et al., Feb. 25, 2012, "Motion Capture Apparatus"); 20120092156 (Tran, Apr. 19, 2012, "Personal Emergency Response (PER) System"); 20120108917 (Libbus et al., May 3, 2012, "Patient Monitoring Systems and Methods"); and 20120116257 (Leuthardt et al., May 10, 2012, "Postural Information System and Method Including Determining Response to Subject Advisory Information").

Examples of prior art in this category also include U.S. patent applications: 20120172126 (Padovani et al., Jul. 5, 2012, "Method and Apparatus for Tracking Orientation of a User"); 20120178534 (Ferguson et al., Jul. 12, 2012, "Human Movement Measurement System"); 20120223880 (Birnbaum et al., Sep. 6, 2012, "Method and Apparatus for Producing a Dynamic Haptic Effect"); 20120274554 (Kinoshita et al., Nov. 6, 2012, "Body Movement Detection Device and Display Control Method of body movement Detection Device"); 20120316455 (Rahman et al., Dec. 13, 2012, "Wearable Device and Platform for Sensory Input"); 20120319940 (Bress et al., Dec. 20, 2012, "Wearable Digital Input Device for Multipoint Free Space Data Collection and Analysis"); 20130015976 (Chang et al., Jan. 17, 2013, "System and Method of Biomechanical posture Detection and Feedback"); 20130068017 (Perkins et al., Mar. 26, 2013, "Apparatus and Method for Analyzing the Motion of a Body"); 20130072765 (Kahn et al., Mar. 26, 2013, "Body-Worn Monitor"); 20130073248 (Perkins et al., Mar. 26, 2013, "Apparatus and Method for Employing Miniature Inertial Measurement Units for Deducing Forces and Moments on Bodies"); 20130110011 (McGregor et al., May 2, 2013, "Method of Monitoring Human Body Movement"); and 20130123665 (Mariani et al., May 16, 2013, "System and Method for 3D Gait Assessment").

Examples of prior art in this category also include U.S. patent applications: 20130158686 (Zhang et al., Jun. 20, 2013, "Intelligent Activity Monitor"); 20130173171 (Drysdale et al., Jul. 4, 2013, "Data-Capable Strapband"); 20130204411 (Clark et al., Aug. 8, 2013, "Inertial Measurement of Sports Motion"); 20130207889 (Chang et al., Aug. 15, 2013, "System and Method of Biomechanical Posture Detection and Feedback Including Sensor Normalization"); 20130211291 (Tran, Aug. 15, 2013, "Personal Emergency Response (PER) System"); 20130215230 (Miesnieks et al., Aug. 22, 2013, "Augmented Reality System using a Portable Device"); 20130222565 (Guerin et al., Aug. 29, 2013, "System and Method for Sensor Fusion of Single Range Camera Data and Inertial Measurement for motion capture"); 20130253875 (Flentov et al., Sep. 26, 2013, "Movement Monitoring Systems and Associated Methods"); 20130289932 (Baechler, Oct. 31, 2013, "Method for Configuring a Motion Sensor as Well as a Configurable Motion Sensor and a System for Configuring Such a Motion Sensor"); 20130303286 (Ferguson et al., Nov. 14, 2013, "Human Movement Measurement System"); and 20140070957 (Longinotti-Buitoni et al., Mar. 13, 2014, "Wearable Communication Platform").

Examples of prior art in this category also include U.S. patent applications: 20140142733 (Tropper et al., May 22, 2014, "Methods for Detecting and Recording Activity and Devices for Performing the Same"); 20140143031 (Tropper et al., May 22, 2014, "Methods for Detecting and Recording Physical Activity of Person"); 20140143038 (Tropper et al., May 22, 2014, "Personal Activity Tracking System"); 20140159894 (Tropper et al., Jun. 12, 2014, "Personal Activity Tracking Device"); 20140171834 (Degoede et al., Jun. 19, 2014, "Electronic-Movement Analysis Tool for Motor Control Rehabilitation and Method of Using the Same"); 20140172134 (Meschter, Jun. 19, 2014, "Apparel Having Sensor System"); 20140188499 (Bell et al., Jul. 3, 2014, "Human Action Monitor"); 20140194781 (Einarsson, Jul. 10, 2014, "Wearable Device Having Feedback Characteristics"); 20140197946 (Park, Jul. 17, 2014, "Portable Monitoring Devices and Methods of Operating the Same"); 20140197963 (Park et al., Jul. 17, 2014, "Portable Monitoring Devices and Methods of Operating the Same"); and 20140197965 (Park et al., Jul. 17, 2014, "Portable Monitoring Devices and Methods of Operating the Same").

Examples of prior art in this category also include U.S. patent applications: 20140206327 (Ziemianska et al., Jul. 24, 2014, "Method and Apparatus for Automatically Adjusting the Operation of Notifications Based on Changes in Physical Activity Level"); 20140213856 (Teller et al., Jul. 31, 2014, "System for Automatic Journaling of a User's Context"); 20140213857 (Teller et al., Jul. 31, 2014, "System for Automatic Journaling of a User's Context"); 20140221769 (Teller et al., Aug. 7, 2014, "Systems and Methods for Measuring Energy Expenditure of an Individual"); 20140223407 (Teller et al., Aug. 7, 2014, "Systems and Methods for Measuring Energy Expenditure"); 20140240103 (Lake et al., Aug. 28, 2014, "Methods and Devices for Combining Muscle Activity Sensor Signals and Inertial Sensor Signals for Gesture-Based Control"); 20140240122 (Roberts et al., Aug. 28, 2014, "Notifications on a User Device Based on Activity Detected by an Activity Monitoring Device"); 20140249381 (LeBoeuf et al., Sep. 4, 2014, "Light-Guiding Devices and Monitoring Devices Incorporating Same"); and 20140275812 (Stivoric et al., Sep. 18, 2014, "Flexible Wearable Body Monitor Device with Sensor").

Examples of prior art in this category also include U.S. patent applications: 20140275813 (Stivoric et al., Sep. 18, 2014, "Wearable Body Monitor Device with a Flexible Section and Sensor Therein"); 20140288875 (Donaldson, Sep. 25, 2014, "Methods and Architecture for Determining Activity and Activity Types From Sensed Motion Signals"); 20140288877 (Donaldson, Sep. 25, 2014, "Intermediate Motion Signal Extraction to Determine Activity"); 20140288878 (Donaldson, Sep. 25, 2014, "Identification of Motion Characteristics to Determine Activity"); 20150015417 (Libbus et al., Jan. 15, 2015, "Patient Monitoring Systems and Methods"); 20150019135 (Kacyvenski et al., Jan. 15, 2015, "Motion Sensor and Analysis"); and 20150045699 (Mokaya et al., Feb. 12, 2015, "Musculoskeletal Activity Recognition System and Method").

8. Wearable Pressure Sensors

Prior art in this category uses one or more wearable pressure sensors to estimate and/or model body motion, posture, and/or configuration. This category is relatively small and is most commonly focused on some type of pressure sensor in a person's shoes, but there are examples of pressure sensors worn on other body locations. Although this present invention does not focus on pressure sensors, the parent application of this present invention uses pressure-sensing tubes to estimate and/or model body motion, posture, and/or configuration so this category of art is relevant and specific examples are now listed.

Examples of prior art which appear to be within this category include the following U.S. Pat. Nos.: 3,974,491 (Sipe, Aug. 10, 1976, "Load Signaling Device for a Patient's Foot"); 5,592,401 (Kramer, Jan. 7, 1997, "Accurate, Rapid, Reliable Position Sensing using Multiple Sensing Technologies"); 5,989,700 (Krivopal, Nov. 25, 1999, "Pressure Sensitive Ink Means, and Methods of Use"); 6,148,280 (Kramer, Nov. 14, 2000, "Accurate, Rapid, Reliable Position Sensing using Multiple Sensing Technologies"); 6,210,301 (Abraham-Fuchs et al., Apr. 3, 2001, "Patient Monitoring System"); 6,611,789 (Darley, Aug. 26, 2003, "Monitoring Activity of a User in Locomotion on Foot"); 6,836,744 (Asphahani et al., Dec. 28, 2004, "Portable System for Analyzing Human Gait"); 6,964,205 (Papakostas et al., Nov. 15, 2005, "Sensor with Plurality of Sensor Elements Arranged with Respect to a Substrate"); and 7,245,292 (Custy, Jul. 17, 2007, "Apparatus and Method for Incorporating Tactile Control and Tactile Feedback Into a Human-Machine Interface").

Examples of prior art in this category also include U.S. Pat. Nos.: 7,258,026 (Papakostas et al., Aug. 26, 2007, "Sensor with a Plurality of Sensor Elements Arranged with Respect to a Substrate"); 7,980,141 (Connor et al., Jul. 19, 2011, "Wearable Position or Motion Sensing Systems or Methods"); 7,998,092 (Avni et al., Aug. 16, 2011, "Force Sensor System for Use in Monitoring Weight Bearing"); 8,011,229 (Lieberman et al., Sep. 6, 2011, "Determining Postural Stability"); 8,033,916 (Caldwell et al., Oct. 11, 2011, "Grip Pressure Sensor"); 8,109,149 (Kotovsky, Feb. 7, 2012, "Contact Stress Sensor"); 8,111,165 (Ortega et al., Feb. 7, 2012, "Active On-Patient Sensor, Method and System"); 8,151,648 (Yu et al., Apr. 10, 2012, "Ultra-Miniature Fiber-Optic Pressure Sensor System and Method of Fabrication"); 8,161,826 (Taylor, Apr. 24, 2012, "Elastically Stretchable Fabric Force Sensor Arrays and Methods of Making"); 8,162,857 (Lanfermann et al., Apr. 24, 2012, "Limb Movement Monitoring System"); 8,280,681 (Vock et al., Oct. 2, 2012, "Pressure-Based Weight Monitoring System for Determining Improper Walking or Running"); and 8,316,719 (Majidi et al., Nov. 27, 2012, "Stretchable Two-Dimensional Pressure Sensor").

Examples of prior art in this category also include U.S. Pat. Nos.: 8,384,551 (Ross et al., Feb. 26, 2013, "Sensor Device and Method for Monitoring Physical Stresses Placed on a User"); 8,416,088 (Ortega et al., Apr. 9, 2013, "Active On-Patient Sensor, Method and System"); 8,459,128 (Bhat et al., Jun. 11, 2013, "Sub-Threshold Elastic Deflection FET Sensor for Sensing Pressure/Force, a Method and System Thereof"); 8,463,573 (Flentov et al., Jun. 11, 2013, "Movement Monitoring Systems and Associated Methods"); 8,626,472 (Solinsky, Jan. 7, 2014, "System and Method for Measuring Balance and Track Motion in Mammals"); 8,661,915 (Taylor, Mar. 4, 2014, "Elastically Stretchable Fabric Force Sensor Arrays and Methods of Making"); 8,784,342 (Hyde et al., Jul. 22, 2014, "Shape Sensing Clothes to Inform the Wearer of a Condition"); and 8,904,876 (Taylor et al., Dec. 9, 2014, "Flexible Piezocapacitive and Piezoresistive Force and Pressure Sensor").

Examples of prior art which appear to be within this category include the following U.S. patent applications: 20030054923 (Brassil et al., Mar. 20, 2003, "Hand Rehabilitation Glove"); 20060212097 (Varadan et al., Sep. 26, 2006, "Method and Device for Treatment of Medical Conditions and Monitoring Physical Movements"); 20060282017 (Avni et al., Dec. 14, 2006, "Force Sensor System for Use in Monitoring Weight Bearing"); 20090025483 (Connor et al., Jan. 29, 2009, "Wearable Position or Motion Sensing Systems or Methods"); 20090076419 (Namineni et al., Mar. 19, 2009, "Loss-of-Balance and Fall Detection System"); 20100036288 (Lanfermann et al., Feb. 11, 2010, "Limb Movement Monitoring System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); and 20100225491 (Leuthardt et al., Sep. 9, 2010, "Postural Information System and Method").

Examples of prior art in this category also include U.S. patent applications: 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); and 20100228490 (Leuthardt et al., Sep. 9, 2010, "Postural Information System and Method").

Examples of prior art in this category also include U.S. patent applications: 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); and 20100271200 (Leuthardt et al., Oct. 28, 2010, "Postural Information System and Method Including Determining Response to Subject Advisory Information").

Examples of prior art in this category also include U.S. patent applications: 20110208444 (Solinsky, Aug. 25, 2011, "System and Method for Measuring Balance and Track Motion in Mammals"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120118066 (Majidi et al., May 17, 2012, "Stretchable Two-Dimensional Pressure Sensor"); 20120323501 (Sarrafzadeh et al., Dec. 20, 2012, "Fabric-Based Pressure Sensor Arrays and Methods for Data Analysis"); 20120323501 (Sarrafzadeh et al., Dec. 20, 2012, "Fabric-Based Pressure Sensor Arrays and Methods for Data Analysis"); 20130253875 (Flentov et al., Sep. 26, 2013, "Movement Monitoring Systems and Associated Methods"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); and 20140172134 (Meschter, Jun. 19, 2014, "Apparel Having Sensor System").

9. Wearable Electromagnetic Energy Bend Sensors and/or Electrogoniometers

Prior art in this category uses one or more electromagnetic energy bend sensors and/or electrogoniometers which are worn on the body in order to estimate and/or model body motion, posture, and/or configuration. This category is relatively large, especially with respect to devices to estimate the angle of a single body joint. Incorporation of multiple electromagnetic energy bend sensors into clothing is less common, but growing. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. Pat. Nos.: 5,012,819 (Marras et al., May 7, 1991, "Apparatus for Monitoring the Motion Components of the Spine"); 5,086,785 (Gentile et al., Feb. 11, 1992, "Angular Displacement Sensor"); 5,184,319 (Kramer, Feb. 2, 1993, "Force Feedback and Textures Simulating Interface Device"); 5,280,265 (Kramer et al., Jan. 18, 1994, "Strain-Sensing Goniometers, Systems and Recognition Algorithms"); 5,316,017 (Edwards et al., May 31, 1994, "Man-Machine Interface for a Joint Measurement System"); 5,442,729 (Kramer et al., Aug. 15, 1995, "Strain-Sensing Goniometers, Systems and Recognition Algorithms"); 5,474,088 (Zaharkin et al., Dec. 12, 1995, "Device for Measuring Motion Characteristics of a Human Joint"); 5,533,531 (Edwards et al., Jul. 9, 1996, "Electronically Aligned Man-Machine Interface"); 5,592,401 (Kramer, Jan. 7, 1997, "Accurate, Rapid, Reliable Position Sensing using Multiple Sensing Technologies"); 5,640,971 (Martin, Jr., Jun. 24, 1997, "Back Movement Monitor and Warning Device"); 5,676,157 (Kramer, Oct. 14, 1997, "Determination of Kinematically Constrained Multi-Articulated Structures"); 5,813,406 (Kramer et al., Sep. 29, 1998, "Strain-Sensing Goniometers, Systems and Recognition Algorithms"); and 5,930,741 (Kramer, Jul. 27, 1999, "Accurate, Rapid, Reliable Position Sensing using Multiple Sensing Technologies").

Examples of prior art in this category also include U.S. Pat. Nos.: 5,980,472 (Seyl, Nov. 9, 1999, "Joint Movement Monitoring System"); 6,005,548 (Latypov et al., Dec. 26, 1999, "Method for Tracking and Displaying User's Spatial Position and Orientation, a Method for Representing Virtual Reality for a User, and Systems of Embodiment of Such Methods"); 6,035,274 (Kramer et al., Mar. 7, 2000, "Strain-Sensing Goniometers, Systems and Recognition Algorithms"); 6,042,555 (Kramer et al., Mar. 28, 2000, "Force-Feedback Interface Device for the Hand"); 6,050,962 (Kramer et al., Apr. 18, 2000, "Goniometer-Based Body-Tracking Device and Method"); 6,104,379 (Petrich et al., Aug. 15, 2000, "Forearm-Supported Exoskeleton Hand-Tracking Device"); 6,110,130 (Kramer, Aug. 29, 2000, "Exoskeleton Device for Directly Measuring Fingertip Position and Inferring Finger Joint Angle"); 6,119,516 (Hock, Sep. 19, 2000, "Biofeedback System for Monitoring the Motion of Body Joint"); 6,127,672 (Danisch, Oct. 3, 2000, "Topological and Motion Measuring Tool"); 6,148,280 (Kramer, Nov. 14, 2000, "Accurate, Rapid, Reliable Position Sensing using Multiple Sensing Technologies"); 6,162,190 (Kramer, Dec. 19, 2000, "Determination of Kinematically Constrained Multi-Articulated Structures"); 6,246,390 (Rosenberg, Jun. 12, 2001, "Multiple Degree-of-Freedom Mechanical Interface to a Computer System"); 6,304,840 (Vance et al., Oct. 16, 2001, "Fingerless Glove for Interacting with Data Processing System"); 6,334,852 (Seyl, Jan. 1, 2002, "Joint Movement Monitoring System"); 6,341,504 (Istook, Jan. 29, 2002, "Composite Elastic and Wire Fabric for Physiological Monitoring Apparel"); and 6,360,615 (Smela, Mar. 26, 2002, "Wearable Effect-Emitting Strain Gauge Device").

Examples of prior art in this category also include U.S. Pat. Nos.: 6,413,229 (Kramer et al., Jul. 2, 2002, "Force-Feedback Interface Device for the Hand"); 6,428,490 (Kramer et al., Aug. 6, 2002, "Goniometer-Based Body-Tracking Device and Method"); 6,487,906 (Hock, Dec. 3, 2002, "Flexible Film Sensor System for Monitoring Body Motion"); 6,497,672 (Kramer, Dec. 24, 2002, "Device and Method for Measuring the Position of Animate Links"); 6,563,107 (Danisch et al., May 13, 2003, "Topological and Motion Measuring Tool"); 6,579,248 (Cascone et al., Jun. 17, 2003, "Biofeedback Device"); 6,640,202 (Dietz et al., Oct. 28, 2003, "Elastic Sensor Mesh System for 3-Dimensional Measurement, Mapping and Kinematics Applications"); 6,673,027 (Fischer, Jan. 6, 2004, "Posture Measurement and Feedback Instrument for Seated Occupations"); 6,701,296 (Kramer et al., Mar. 2, 2004, "Strain-Sensing Goniometers, Systems, and Recognition Algorithms"); 6,834,436 (Townsend et al., Dec. 28, 2004, "Posture and Body Movement Measuring System"); 6,866,643 (Kramer, Mar. 15, 2005, "Determination of Finger Position"); 6,871,413 (Arms et al., Mar. 29, 2005, "Miniaturized Inclinometer for Angle Measurement with Accurate Measurement Indicator"); 6,957,164 (Dietz et al., Oct. 18, 2005, "Elastic Sensor Mesh System for 3-Dimensional Measurement, Mapping and Kinematics Applications"); 6,964,205 (Papakostas et al., Nov. 15, 2005, "Sensor with Plurality of Sensor Elements Arranged with Respect to a Substrate"); 6,979,164 (Kramer, Dec. 27, 2005, "Force Feedback and Texture Simulating Interface Device"); 7,070,571 (Kramer et al., Jul. 4, 2006, "Goniometer-Based Body-Tracking Device"); and 7,082,570 (von Wiegand et al., Jul. 25, 2006, "Distributed Haptic Interface System and Method").

Examples of prior art in this category also include U.S. Pat. Nos.: 7,135,227 (Karayianni et al., Nov. 14, 2006, "Electrically Conductive Elastic Composite Yarn, Methods for Making the Same, and Articles Incorporating the Same"); 7,191,803 (Orr et al., Mar. 20, 2007, "Elastic Fabric with Sinusoidally Disposed Wires"); 7,209,028 (Boronkay et al., Apr. 24, 2007, "Position Sensor with Resistive Element"); 7,210,240 (Townsend et al., May 6, 2007, "Posture and Body Movement Measuring System"); 7,258,026 (Papakostas et al., Aug. 26, 2007, "Sensor with a Plurality of Sensor Elements Arranged with Respect to a Substrate"); 7,390,157 (Kramer, Jun. 24, 2008, "Force Feedback and Texture Simulating Interface Device"); 7,413,802 (Karayianni et al., Aug. 19, 2008, "Energy Active Composite Yarn, Methods for Making the Same, and Articles Incorporating the Same"); 7,500,853 (Bevirt et al., Mar. 10, 2009, "Mechanical Interface for a Computer System"); and 7,509,870 (Aebersold et al., Mar. 31, 2009, "MEMS Capacitive Bending and Axial Strain Sensor").

Examples of prior art in this category also include U.S. Pat. Nos.: 7,665,288 (Karayianni et al., Feb. 25, 2010, "Energy Active Composite Yarn, Methods for Making the Same and Articles Incorporating the Same"); 7,698,830 (Townsend et al., Apr. 20, 2010, "Posture and Body Movement Measuring System"); 7,703,333 (Hayakawa et al., Apr. 27, 2010, "Deformation Sensor"); 7,771,318 (Narayanaswami, Aug. 10, 2010, "Device for Monitoring a User's Posture"); 7850574 (Narayanaswami, Dec. 14, 2010, "Device for Monitoring a User's Posture"); 7,854,174 (Aebersold et al., Dec. 26, 2010, "MEMS Capacitive Bending and Axial Strain Sensor"); 7,901,756 (Bun et al., Mar. 8, 2011, "Functional Elastic Textile Structures"); 7,902,095 (Hassonjee et al., Mar. 8, 2011, "Functional Textile Structures"); 7,926,254 (Karayianni et al., Apr. 19, 2011, "Electrically Conductive Elastic Composite Yarn, Methods for Making the Same, and Articles Incorporating the Same"); 7,981,057 (Stewart, Jul. 19, 2011, "Joint Motion Sensing to Make a Determination of a Positional Change of an Individual"); 8,083,693 (McKeon et al., Dec. 27, 2011, "Monitoring Posture"); 8,157,752 (Fischer, Apr. 17, 2012, "Posture Assessment and Feedback Instrument"); 8,161,826 (Taylor, Apr. 24, 2012, "Elastically Stretchable Fabric Force Sensor Arrays and Methods of Making"); and 8,203,455 (Lee et al., Jun. 19, 2012, "Posture Sensing Alert Apparatus").

Examples of prior art in this category also include U.S. Pat. Nos.: 8,362,882 (Heubel et al., Jan. 29, 2013, "Method and Apparatus for Providing Haptic Feedback from Haptic Textile"); 8,421,448 (Tran et al., Apr. 16, 2013, "Hall-Effect Sensor System for Gesture Recognition, Information Coding, and Processing"); 8,459,128 (Bhat et al., Jun. 11, 2013, "Sub-Threshold Elastic Deflection FET Sensor for Sensing Pressure/Force, a Method and System Thereof"); 8,626,472 (Solinsky, Jan. 7, 2014, "System and Method for Measuring Balance and Track Motion in Mammals"); 8,661,915 (Taylor, Mar. 4, 2014, "Elastically Stretchable Fabric Force Sensor Arrays and Methods of Making"); 8,665,241 (Heubel et al., Mar. 4, 2014, "System and Method for Providing Haptic Feedback from Haptic Textile"); 8,678,979 (Stark et al., Mar. 25, 2014, "Remote Monitoring of a Patient"); 8,784,342 (Hyde et al., Jul. 22, 2014, "Shape Sensing Clothes to Inform the Wearer of a Condition"); 8,904,876 (Taylor et al., Dec. 9, 2014, "Flexible Piezocapacitive and Piezoresistive Force and Pressure Sensor"); and 8,932,236 (McKeon et al., Jan. 13, 2015, "Monitoring Posture").

Examples of prior art which appear to be within this category include the following U.S. patent applications: 20010020140 (Kramer, Sep. 6, 2001, "Device and Method for Measuring the Position of Animate Links"); 20020088931 (Danisch et al., Jul. 11, 2002, "Topological and Motion Measuring Tool"); 20020151824 (Fischer, Oct. 17, 2002, "Posture Measurement and Feedback Instrument for Seated Occupations"); 20020198472 (Kramer, Dec. 26, 2002, "Determination of Finger Position"); 20030083596 (Kramer et al., May 6, 2003, "Goniometer-Based Body-Tracking Device and Method"); 20050126026 (Townsend et al., Jun. 16, 2005, "Posture and Body Movement Measuring System"); 20060130347 (Bergamasco et al., Jun. 22, 2006, "Device for Gioniometric Measurements"); 20060217233 (Lee, Sep. 28, 2006, "Apparatus and Method for Lower-Limb Rehabilitation Training Using Weight Load and Joint Angle as Variables"); 20070169364 (Townsend et al., Jul. 26, 2007, "Posture and Body Movement Measuring System"); 20070256502 (Aebersold et al., Nov. 8, 2007, "MEMS Capacitive Bending and Axial Strain Sensor"); and 20090188325 (Aebersold et al., Jul. 30, 2009, "MEMS Capacitive Bending and Axial Strain Sensor").

Examples of prior art in this category also include U.S. patent applications: 20090278791 (Slycke et al., Nov. 12, 2009, "Motion Tracking System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); and 20100228487 (Leuthardt et al., Sep. 9, 2010, "Postural Information System and Method").

Examples of prior art in this category also include U.S. patent applications: 20100228488 (Leuthardt et al., Sep. 9, 2010, "Postural Information System and Method"); 20100228489 (Leuthardt et al., Sep. 9, 2010, "Postural Information System and Method"); 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); and 20110046518 (Fischer, Feb. 24, 2011, "Posture Assessment and Feedback Instrument").

Examples of prior art in this category also include U.S. patent applications: 20110046915 (Hol et al., Feb. 24, 2011, "Use of Positioning Aiding System for Inertial Motion Capture"); 20110052005 (Selner, Mar. 3, 2011, "Designation of a Characteristic of a Physical Capability by Motion Analysis, Systems and Methods"); 20110208444 (Solinsky, Aug. 25, 2011, "System and Method for Measuring Balance and Track Motion in Mammals"); 20110248773 (Poupyrev et al., Oct. 13, 2011, "System and Method for Sensing Human Activity by Monitoring Impedance"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120323501 (Sarrafzadeh et al., Dec. 20, 2012, "Fabric-Based Pressure Sensor Arrays and Methods for Data Analysis"); and 20120323501 (Sarrafzadeh et al., Dec. 20, 2012, "Fabric-Based Pressure Sensor Arrays and Methods for Data Analysis").

Examples of prior art in this category also include U.S. patent applications: 20130113506 (Poupyrev et al., May 9, 2013, "System and Method for Sensing Human Activity by Monitoring Impedance"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); 20140172134 (Meschter, Jun. 19, 2014, "Apparel Having Sensor System"); 20140342844 (Mooney, Nov. 20, 2014, "Apparatus and Method for Analysing a Golf Swing"); and 20150005608 (Evans et al., Jan. 1, 2015, "Electrode Units for Sensing Physiological Electrical Activity").

10. Wearable Light Energy Bend Sensors

Prior art in this category uses one or more light energy bend sensors which are worn on the body in order to estimate and/or model body motion, posture, and/or configuration. Many of the examples in this category are fiber optic channels which detect bending by changes in light transmitted through these channels. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. Pat. Nos.: 4,542,291 (Zimmerman, Sep. 17, 1985, "Optical Flex Sensor"); 5,184,009 (Wright et al., Feb. 2, 1993, "Optical Attenuator Movement Detection System"); 5,280,265 (Kramer et al., Jan. 18, 1994, "Strain-Sensing Goniometers, Systems and Recognition Algorithms"); 5,442,729 (Kramer et al., Aug. 15, 1995, "Strain-Sensing Goniometers, Systems and Recognition Algorithms"); 5,592,401 (Kramer, Jan. 7, 1997, "Accurate, Rapid, Reliable Position Sensing using Multiple Sensing Technologies"); 5,676,157 (Kramer, Oct. 14, 1997, "Determination of Kinematically Constrained Multi-Articulated Structures"); 5,694,497 (Sansone, Dec. 2, 1997, "Intrinsically Self Deforming Fiber Optic Microbend Pressure and Strain Sensor"); 5,813,406 (Kramer et al., Sep. 29, 1998, "Strain-Sensing Goniometers, Systems and Recognition Algorithms"); 5,930,741 (Kramer, Jul. 27, 1999, "Accurate, Rapid, Reliable Position Sensing using Multiple Sensing Technologies"); 6,003,340 (Borak et al., Dec. 26, 1999, "Method of Putting a Bend Into a Fiber to Make a Strain Sensor"); and 6,035,274 (Kramer et al., Mar. 7, 2000, "Strain-Sensing Goniometers, Systems and Recognition Algorithms").

Examples of prior art in this category also include U.S. Pat. Nos.: 6,042,555 (Kramer et al., Mar. 28, 2000, "Force-Feedback Interface Device for the Hand"); 6,050,962 (Kramer et al., Apr. 18, 2000, "Goniometer-Based Body-Tracking Device and Method"); 6,104,379 (Petrich et al., Aug. 15, 2000, "Forearm-Supported Exoskeleton Hand-Tracking Device"); 6,110,130 (Kramer, Aug. 29, 2000, "Exoskeleton Device for Directly Measuring Fingertip Position and Inferring Finger Joint Angle"); 6,127,672 (Danisch, Oct. 3, 2000, "Topological and Motion Measuring Tool"); 6,148,280 (Kramer, Nov. 14, 2000, "Accurate, Rapid, Reliable Position Sensing using Multiple Sensing Technologies"); 6,162,190 (Kramer, Dec. 19, 2000, "Determination of Kinematically Constrained Multi-Articulated Structures"); 6,304,840 (Vance et al., Oct. 16, 2001, "Fingerless Glove for Interacting with Data Processing System"); 6,389,187 (Greenaway et al., May 14, 2002, "Optical Fiber Bend Sensor"); 6,413,229 (Kramer et al., Jul. 2, 2002, "Force-Feedback Interface Device for the Hand"); 6,428,490 (Kramer et al., Aug. 6, 2002, "Goniometer-Based Body-Tracking Device and Method"); 6,429,421 (Meller et al., Aug. 6, 2002, "Flexible Fiber Optic Microbend Device, with Interlocking Flexible Fibers, Sensors, and Method Use"); 6,497,672 (Kramer, Dec. 24, 2002, "Device and Method for Measuring the Position of Animate Links"); 6,563,107 (Danisch et al., May 13, 2003, "Topological and Motion Measuring Tool"); and 6,621,948 (Devenyi, Sep. 16, 2003, "Apparatus and Method for Differential Output Optical Fiber Displacement Sensing").

Examples of prior art in this category also include U.S. Pat. Nos.: 6,701,296 (Kramer et al., Mar. 2, 2004, "Strain-Sensing Goniometers, Systems, and Recognition Algorithms"); 6,728,431 (Ames et al., Apr. 27, 2004, "Fiber Optic Curvature Sensor for Towed Hydrophone Arrays"); 6,866,643 (Kramer, Mar. 15, 2005, "Determination of Finger Position"); 6,940,062 (Kwon et al., Sep. 6, 2005, "Optical Fiber Curvature Sensor for Measuring Body Motion and Its Adhesive Method"); 7,070,571 (Kramer et al., Jul. 4, 2006, "Goniometer-Based Body-Tracking Device"); 7,324,714 (Cranch et al., Jan. 29, 2008, "Multicore Fiber Curvature Sensor"); 7,413,802 (Karayianni et al., Aug. 19, 2008, "Energy Active Composite Yarn, Methods for Making the Same, and Articles Incorporating the Same"); 7,630,591 (Allen et al., Dec. 8, 2009, "Optical Fiber Substrate Useful as a Sensor or Illumination Device Component"); 7,665,288 (Karayianni et al., Feb. 25, 2010, "Energy Active Composite Yarn, Methods for Making the Same and Articles Incorporating the Same"); and 7,771,318 (Narayanaswami, Aug. 10, 2010, "Device for Monitoring a User's Posture").

Examples of prior art in this category also include U.S. Pat. Nos.: 7,772,541 (Froggatt et al., Aug. 10, 2010, "Fiber Optic Position and/or Shape Sensing Based on Rayleigh Scatter"); 7,781,724 (Childers et al., Aug. 24, 2010, "Fiber Optic Position and Shape Sensing Device and Method Relating Thereto"); 7,815,376 (Rogers et al., Oct. 19, 2010, "Fixture for Shape-Sensing Optical Fiber in a Kinematic Chain"); 7,850,574 (Narayanaswami, Dec. 14, 2010, "Device for Monitoring a User's Posture"); 7,901,756 (Burr et al., Mar. 8, 2011, "Functional Elastic Textile Structures"); 7,902,095 (Hassonjee et al., Mar. 8, 2011, "Functional Textile Structures"); 7,911,620 (Digonnet et al., Mar. 22, 2011, "Optical Utilizing Hollow-Core Photonic Bandgap Fiber with Low Phase Thermal Constant"); 7,930,065 (Larkin et al., Apr. 19, 2011, "Robotic Surgery System Including Position Sensors using Fiber Bragg Gratings"); 7,999,946 (Andersen et al., Aug. 16, 2011, "Fiber Optic Particle Motion Sensor System"); 8,068,231 (Digonnet, Nov. 29, 2011, "Fiber Optic Sensor using a Bragg Fiber"); 8,116,601 (Prisco, Feb. 14, 2012, "Fiber Optic Shape Sensing"); 8,151,648 (Yu et al., Apr. 10, 2012, "Ultra-Miniature Fiber-Optic Pressure Sensor System and Method of Fabrication"); 8,162,857 (Lanfermann et al., Apr. 24, 2012, "Limb Movement Monitoring System"); and 8,182,158 (Rogers et al., May 22, 2012, "Fixture for Shape-Sensing Optical Fiber in a Kinematic Chain").

Examples of prior art in this category also include U.S. Pat. Nos.: 8,206,325 (Najafi et al., Jun. 26, 2012, "Ambulatory System for Measuring and Monitoring Physical Activity and Risk of Falling and for Automatic Fall Detection"); 8,233,151 (Digonnet, Jul. 31, 2012, "Fiber Optic Sensor using a Hollow Core Fiber"); 8,240,207 (Andersen et al., Aug. 14, 2012, "Fiber Optic Particle Motion Sensor and Measuring Method using the Sensor"); 8,358,883 (Prisco, Jan. 22, 2013, "Fiber Optic Shape Sensor"); 8,395,109 (Muraysky, Mar. 12, 2013, "Motion Sensor for Detecting Bending or Pivoting"); 8,427,651 (Digonnet, Apr. 25, 2013, "Optical using a Hollow Core Waveguide"); 8,520,472 (Murray et al., Aug. 27, 2013, "Compact Laser Sensors and Monitoring Systems Including Such Sensor"); 8,616,782 (Rogers et al., Dec. 31, 2013, "Fixture for Shape-Sensing Optical Fiber in a Kinematic Chain"); 8,655,117 (Donlagic et al., Feb. 18, 2014, "Optical Fiber Sensors Having Long Active Lengths, Systems, and Methods"); 8,780,339 (Udd, Jul. 15, 2014, "Fiber Shape Sensing Systems and Methods"); and 8,784,303 (Laby et al., Jul. 22, 2014, "System for Controlling an Instrument Using Shape Sensor").

Examples of prior art which appear to be within this category include the following U.S. patent applications: 20010020140 (Kramer, Sep. 6, 2001, "Device and Method for Measuring the Position of Animate Links"); 20020024656 (Kwon et al., Feb. 28, 2002, "Optical Fiber Curvature Sensor for Measuring Body Motion and Its Adhesive Method"); 20020088931 (Danisch et al., Jul. 11, 2002, "Topological and Motion Measuring Tool"); 20020198472 (Kramer, Dec. 26, 2002, "Determination of Finger Position"); 20030083596 (Kramer et al., May 1, 2003, "Goniometer-Based Body-Tracking Device and Method"); 20100036288 (Lanfermann et al., Feb. 11, 2010, "Limb Movement Monitoring System"); 20100183297 (Barboutis et al., Jul. 22, 2010, "Optical Fiber Sensor Having Electrical Connectors"); 20100198113 (Coulston, Aug. 5, 2010, "Extended Optical Range Reflective System for Monitoring Motion of a Member"); and 20100225473 (Leuthardt et al., Sep. 9, 2010, "Postural Information System and Method").

Examples of prior art in this category also include U.S. patent applications: 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); and 20100228158 (Leuthardt et al., Sep. 9, 2010, "Postural Information System and Method Including Device Level Determining of Subject Advisory Information Based on Subject Status Information and Postural Influencer Status Information").

Examples of prior art in this category also include U.S. patent applications: 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); and 20100228494 (Leuthardt et al., Sep. 9, 2010, "Postural Information System and Method Including Determining Subject Advisory Information Based on Prior Determined Subject Advisory Information").

Examples of prior art in this category also include U.S. patent applications: 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); 20120116257 (Leuthardt et al., May 10, 2012, "Postural Information System and Method Including Determining Response to Subject Advisory Information"); and 20140031698 (Moon et al., Jan. 30, 2014, "Apparatus and Method for Sensing Bone Position and Motion").

SUMMARY OF THE INVENTION

This invention is smart clothing for measuring changes in a person's body configuration. It can be embodied in smart clothing with stretch and/or bend sensors for measuring changes in body configuration comprising: a wearable layer which is configured to be worn by a person, wherein the wearable layer comprises a first electromagnetically-nonconductive material; and an electromagnetically-conductive pathway which is created by printing electromagnetically-conductive ink onto the wearable layer, wherein the ink comprises a mixture of a second electromagnetically-nonconductive material and an electromagnetically-conductive material, wherein stretching and/or bending the electromagnetically-conductive pathway causes changes in the transmission of electromagnetic energy through the electromagnetically-conductive pathway, and wherein the changes in the transmission of electromagnetic energy through the electromagnetically-conductive pathway are analyzed to measure changes in the configuration of the person's body.

In an example, changes in the transmission of electromagnetic energy through an electromagnetically-conductive pathway can be measured by measuring one or more parameters selected from the group consisting of: amperage, capacitance, conductivity, current, electromagnetic wave pattern, impedance, phase, resistance, and voltage. In an example, an electromagnetically-conductive pathway can be helical. In an example, the first electromagnetically-nonconductive material, the second electromagnetically-nonconductive material, or both can be polyurethane. In an example, the electromagnetically-conductive material can be selected from the group consisting of: aluminum, carbon, copper, gold, silver, and steel.

INTRODUCTION TO THE FIGURES

FIG. 11 shows a fourth example of smart clothing with diverging (partial loop) helical electromagnetic energy pathways on a person's arm.

FIG. 12 shows a fifth example of smart clothing with diverging (partial loop) helical electromagnetic energy pathways on a person's arm.

FIG. 17 shows an example of full-body smart clothing with multiple diverging (partial loop) helical electromagnetic energy pathways spanning multiple body joints.

DETAILED DESCRIPTION OF THE FIGURES

Figure 1:
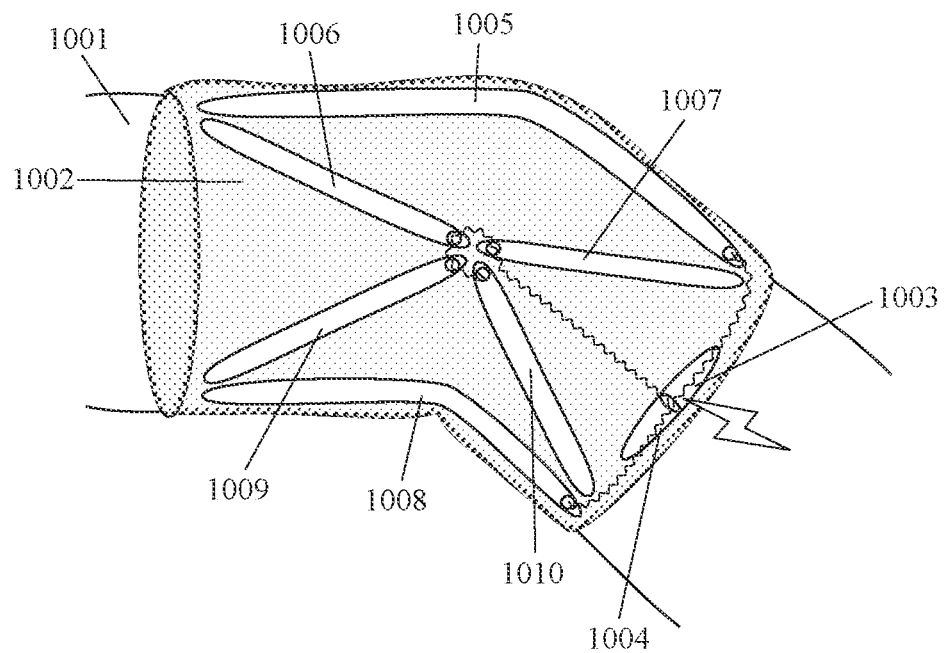
FIG. 1 shows an example of smart clothing with electromagnetic energy pathways spanning a body joint at different angles.

This invention can be embodied in smart clothing with stretch and/or bend sensors for measuring changes in body configuration comprising: a wearable layer which is configured to be worn by a person, wherein the wearable layer comprises a first electromagnetically-nonconductive material; and an electromagnetically-conductive pathway which is created by printing electromagnetically-conductive ink onto the wearable layer, wherein the ink comprises a mixture of a second electromagnetically-nonconductive material and an electromagnetically-conductive material, wherein stretching and/or bending the electromagnetically-conductive pathway causes changes in the transmission of electromagnetic energy through the electromagnetically-conductive pathway, and wherein the changes in the transmission of electromagnetic energy through the electromagnetically-conductive pathway are analyzed to measure changes in the configuration of the person's body.

In an example, changes in the transmission of electromagnetic energy through an electromagnetically-conductive pathway can be measured by measuring one or more parameters selected from the group consisting of: amperage, capacitance, conductivity, current, electromagnetic wave pattern, impedance, phase, resistance, and voltage. In an example, an electromagnetically-conductive pathway can be helical.

In an example, the first electromagnetically-nonconductive material, the second electromagnetically-nonconductive material, or both can comprise a polymer. In an example, the first electromagnetically-nonconductive material, the second electromagnetically-nonconductive material, or both can comprise polyurethane. In an example, the first electromagnetically-nonconductive material, the second electromagnetically-nonconductive material, or both can comprise elastane. In an example, the electromagnetically-conductive material can comprise aluminum, carbon, copper, gold, silver, or steel.

In an example, the first electromagnetically-nonconductive polymer can comprise polyurethane, the second electromagnetically-nonconductive polymer can comprise polyurethane, and the electromagnetically-conductive material can comprise aluminum. In an example, the first electromagnetically-nonconductive polymer can comprise polyurethane, the second electromagnetically-nonconductive polymer can comprise polyurethane, and the electromagnetically-conductive material can comprise carbon. In an example, the first electromagnetically-nonconductive polymer can comprise polyurethane, the second electromagnetically-nonconductive polymer can comprise polyurethane, and the electromagnetically-conductive material can comprise copper. In an example, the first electromagnetically-nonconductive polymer can comprise polyurethane, the second electromagnetically-nonconductive polymer can comprise polyurethane, and the electromagnetically-conductive material can comprise gold. In an example, the first electromagnetically-nonconductive polymer can comprise polyurethane, the second electromagnetically-nonconductive polymer can comprise polyurethane, and the electromagnetically-conductive material can comprise silver. In an example, the first electromagnetically-nonconductive polymer can comprise polyurethane, the second electromagnetically-nonconductive polymer can comprise polyurethane, and the electromagnetically-conductive material can comprise steel.

In an example, computer-guided 3D printing can be used to print electromagnetically-conductive ink on the wearable layer. In an example, smart clothing can further comprise a data processor or other modular electronic members to create an electronically-functional article of clothing. In an example, computer-guided 3D printing can be used to print modular members on the wearable layer to create an electronically-functional article of clothing. In an example, computer-guided 3D printing can be used to place modular members on the wearable layer to create an electronically-functional article of clothing. In an example, computer-guided 3D printing can be used to adhere modular members on the wearable layer to create an electronically-functional article of clothing.

In an example, smart clothing can further comprise an arm associated portion which is configured to span the person's elbow, the person's shoulder, and a portion of the person's torso adjacent to the shoulder; wherein the arm associated portion can be virtually divided into a distal-to-proximal longitudinal sequence of five segments which can be labeled A, B, C, D, and E, wherein segment B is configured to span the elbow, wherein segment D is configured to span the shoulder, wherein segment A is distal relative to segment B, wherein segment C is between segments B and D, wherein segment E is proximal relative to segment D, wherein distal means farther from a person's heart when arms and legs are extended outwards (in a Vitruvian Man manner), and wherein proximal means closer to the person's heart when arms and legs are extended outwards (in a Vitruvian Man manner); wherein each of the five segments can be virtually sub-divided into four radial-quadrant arcuate areas which can be labeled 1st, 2nd, 3rd, and 4th, thereby virtually dividing the arm associated portion into a total of twenty arcuate areas which can be labeled A1, A2, A3, A4, B1, B2, B3, B4, C1, C2, C3, C4, D1, D2, D3, D4, E1, E2, E3, and E4; wherein a virtual cross-sectional plane is perpendicular to a central longitudinal axis of the arm associated portion, wherein a virtual circumference is a circle which most closely fits the intersection of the arm associated portion with a virtual cross-sectional plane, wherein a 0-degree point on a virtual circumference is the most forward point of the circumference when the person stands with arms and legs extended outwards (in a Vitruvian Man manner); wherein a 90-degree point on a virtual circumference is one-quarter of the circumference clockwise (upward for an arm) from the 0-degree point, a 180-degree point on a virtual circumference is one-quarter of the circumference clockwise from the 90-degree point, and a 270-degree point on a virtual circumference is one-quarter of the circumference clockwise from the 180-degree point; wherein virtual 0-degree, 90-degree, 180-degree, and 270-degree longitudinal lines for the arm associated portion can be defined by connecting 0-degree, 90-degree, 180-degree, and 270-degree points, respectively, across a longitudinal sequence of virtual circumferences; wherein a 1st radial-quadrant arcuate area is clockwise between the 0-degree and 90-degree longitudinal lines, wherein a 2nd radial-quadrant arcuate area is clockwise between the 90-degree and 180-degree longitudinal lines, wherein a 3rd radial-quadrant arcuate area is clockwise between the 180-degree and 270-degree longitudinal lines, and wherein a 4th radial-quadrant arcuate area is clockwise between the 270-degree and 0-degree longitudinal lines; wherein the arm associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

In an example, smart clothing can further comprise a leg associated portion which is configured to span the person's knee, the person's hip, and a portion of the person's torso adjacent to the hip; wherein the leg associated portion can be virtually divided into a distal-to-proximal longitudinal sequence of five segments which can be labeled A, B, C, D, and E, wherein segment B is configured to span the knee, wherein segment D is configured to span the hip, wherein segment A is distal relative to segment B, wherein segment C is between segments B and D, wherein segment E is proximal relative to segment D, wherein distal means farther from a person's heart when arms and legs are extended outwards (in a Vitruvian Man manner), and wherein proximal means closer to the person's heart when arms and legs are extended outwards (in a Vitruvian Man manner); wherein each of the five segments can be virtually sub-divided into four radial-quadrant arcuate areas which can be labeled 1st, 2nd, 3rd, and 4th, thereby virtually dividing the leg associated portion into a total of twenty arcuate areas which can be labeled A1, A2, A3, A4, B1, B2, B3, B4, C1, C2, C3, C4, D1, D2, D3, D4, E1, E2, E3, and E4; wherein a virtual cross-sectional plane is perpendicular to a central longitudinal axis of the leg associated portion, wherein a virtual circumference is a circle which most closely fits the intersection of the leg associated portion with a virtual cross-sectional plane, wherein a 0-degree point on a virtual circumference is the most forward point of the circumference when the person stands with arms and legs extended outwards (in a Vitruvian Man manner); wherein a 90-degree point on a virtual circumference is one-quarter of the circumference clockwise (outward for a leg) from the 0-degree point, a 180-degree point on a virtual circumference is one-quarter of the circumference clockwise from the 90-degree point, and a 270-degree point on a virtual circumference is one-quarter of the circumference clockwise from the 180-degree point; wherein virtual 0-degree, 90-degree, 180-degree, and 270-degree longitudinal lines for the leg associated portion can be defined by connecting 0-degree, 90-degree, 180-degree, and 270-degree points, respectively, across a longitudinal sequence of virtual circumferences; wherein a 1st radial-quadrant arcuate area is clockwise between the 0-degree and 90-degree longitudinal lines, wherein a 2nd radial-quadrant arcuate area is clockwise between the 90-degree and 180-degree longitudinal lines, wherein a 3rd radial-quadrant arcuate area is clockwise between the 180-degree and 270-degree longitudinal lines, and wherein a 4th radial-quadrant arcuate area is clockwise between the 270-degree and 0-degree longitudinal lines; wherein the leg associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the leg associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

In an example, smart clothing can comprise a customized article of clothing for measuring changes in a person's body configuration which is created by computer-guided 3D printing electromagnetically-conductive ink onto an electromagnetically-nonconductive material. In an example, an electromagnetic energy pathway can have a helical shape when worn on a person's body. In an example, printing with electromagnetically-conductive ink can create a stretchable and/or bendable electromagnetic energy pathway, wherein changes in a person's body configuration stretch and/or bend the pathway and thus change the transmission of electromagnetic energy through the pathway. In an example, changes in the flow of electromagnetic energy through a pathway can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing.

In an example, this invention can be embodied in an article of smart clothing for measuring body motion and/or configuration comprising: * an article of clothing worn by a person; * wherein the article of clothing further comprises an arm (or leg) associated portion which is configured to span the person's elbow (or knee), the person's shoulder (or hip), and a portion of the person's torso adjacent to the shoulder (or hip); * wherein the arm (or leg) associated portion can be virtually divided into a distal-to-proximal longitudinal sequence of five segments which can be labeled A, B, C, D, and E, wherein segment B is configured to span the elbow (or knee), wherein segment D is configured to span the shoulder (or hip), wherein segment A is distal relative to segment B, wherein segment C is between segments B and D, wherein segment E is proximal relative to segment D, wherein distal means farther from a person's heart when arms and legs are extended outwards (in a Vitruvian Man manner), and wherein proximal means closer to the person's heart when arms and legs are extended outwards (in a Vitruvian Man manner); * wherein each of the five segments can be virtually sub-divided into four radial-quadrant arcuate areas which can be labeled 1st, 2nd, 3rd, and 4th, thereby virtually dividing the arm (or leg) associated portion into a total of twenty arcuate areas which can be labeled A1, A2, A3, A4, B1, B2, B3, B4, C1, C2, C3, C4, D1, D2, D3, D4, E1, E2, E3, and E4; wherein a virtual cross-sectional plane is perpendicular to a central longitudinal axis of the arm (or leg) associated portion, wherein a virtual circumference is a circle which most closely fits the intersection of the arm (or leg) associated portion with a virtual cross-sectional plane, wherein a 0-degree point on a virtual circumference is the most forward point of the circumference when the person stands with arms and legs extended outwards (in a Vitruvian Man manner); wherein a 90-degree point on a virtual circumference is one-quarter of the circumference clockwise (upward for an arm, outward for a leg) from the 0-degree point, a 180-degree point on a virtual circumference is one-quarter of the circumference clockwise from the 90-degree point, and a 270-degree point on a virtual circumference is one-quarter of the circumference clockwise from the 180-degree point; wherein virtual 0-degree, 90-degree, 180-degree, and 270-degree longitudinal lines for the arm (or leg) associated portion can be defined by connecting 0-degree, 90-degree, 180-degree, and 270-degree points, respectively, across a longitudinal sequence of virtual circumferences; wherein a 1st radial-quadrant arcuate area is clockwise between the 0-degree and 90-degree longitudinal lines, wherein a 2nd radial-quadrant arcuate area is clockwise between the 90-degree and 180-degree longitudinal lines, wherein a 3rd radial-quadrant arcuate area is clockwise between the 180-degree and 270-degree longitudinal lines, and wherein a 4th radial-quadrant arcuate area is clockwise between the 270-degree and 0-degree longitudinal lines; * wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; * wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and * wherein changes in the flow of energy through the first flexible energy pathway and changes in the flow of energy through the second flexible energy pathway are analyzed jointly to measure changes in body motion and/or configuration.

In an example, this invention can be embodied in an article of smart clothing for measuring and/or recognizing upper-body motion and/or configuration comprising: * an upper-body article of clothing (e.g. a shirt) worn by a person; * wherein the article of clothing further comprises an arm-associated portion which is configured to span the person's elbow, the person's shoulder, and a portion of the person's torso adjacent to the shoulder; * wherein the arm-associated portion can be virtually divided into a distal-to-proximal longitudinal sequence of five segments which can be labeled A, B, C, D, and E, wherein segment B is configured to span the elbow, wherein segment D is configured to span the shoulder, wherein segment A is distal relative to segment B, wherein segment C is between segments B and D, wherein segment E is proximal relative to segment D, wherein distal means farther from a person's heart when arms and legs are extended outwards (in a Vitruvian Man manner), and wherein proximal means closer to the person's heart when arms and legs are extended outwards (in a Vitruvian Man manner); * wherein each of the five segments can be virtually sub-divided into four radial-quadrant arcuate areas which can be labeled 1st, 2nd, 3rd, and 4th, thereby virtually dividing the arm-associated portion into a total of twenty arcuate areas which can be labeled A1, A2, A3, A4, B1, B2, B3, B4, C1, C2, C3, C4, D1, D2, D3, D4, E1, E2, E3, and E4; wherein a virtual cross-sectional plane is perpendicular to a central longitudinal axis of the arm associated portion, wherein a virtual circumference is a circle which most closely fits the intersection of the arm-associated portion with a virtual cross-sectional plane, wherein a 0-degree point on a virtual circumference is the most forward point of the circumference when the person stands with arms and legs extended outwards (in a Vitruvian Man manner); wherein a 90-degree point on a virtual circumference is one-quarter of the circumference clockwise (upward) from the 0-degree point, a 180-degree point on a virtual circumference is one-quarter of the circumference clockwise from the 90-degree point, and a 270-degree point on a virtual circumference is one-quarter of the circumference clockwise from the 180-degree point; wherein virtual 0-degree, 90-degree, 180-degree, and 270-degree longitudinal lines for the arm-associated portion can be defined by connecting 0-degree, 90-degree, 180-degree, and 270-degree points, respectively, across a longitudinal sequence of virtual circumferences; wherein a 1st radial-quadrant arcuate area is clockwise between the 0-degree and 90-degree longitudinal lines, wherein a 2nd radial-quadrant arcuate area is clockwise between the 90-degree and 180-degree longitudinal lines, wherein a 3rd radial-quadrant arcuate area is clockwise between the 180-degree and 270-degree longitudinal lines, and wherein a 4th radial-quadrant arcuate area is clockwise between the 270-degree and 0-degree longitudinal lines; * wherein the arm-associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; * wherein the arm-associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and * wherein changes in the flow of energy through the first flexible energy pathway and changes in the flow of energy through the second flexible energy pathway are analyzed jointly to measure changes in body motion and/or configuration.

In an example, this invention can be embodied in an article of smart clothing for measuring and/or recognizing lower-body motion and/or configuration comprising: * a lower-body article of clothing (e.g. a pair of pants) worn by a person; * wherein the article of clothing further comprises a leg-associated portion which is configured to span the person's knee, the person's hip, and a portion of the person's torso adjacent to the hip; * wherein the leg-associated portion can be virtually divided into a distal-to-proximal longitudinal sequence of five segments which can be labeled A, B, C, D, and E, wherein segment B is configured to span the knee, wherein segment D is configured to span the hip, wherein segment A is distal relative to segment B, wherein segment C is between segments B and D, wherein segment E is proximal relative to segment D, wherein distal means farther from a person's heart when arms and legs are extended outwards (in a Vitruvian Man manner), and wherein proximal means closer to the person's heart when arms and legs are extended outwards (in a Vitruvian Man manner); * wherein each of the five segments can be virtually sub-divided into four radial-quadrant arcuate areas which can be labeled 1st, 2nd, 3rd, and 4th, thereby virtually dividing the leg-associated portion into a total of twenty arcuate areas which can be labeled A1, A2, A3, A4, B1, B2, B3, B4, C1, C2, C3, C4, D1, D2, D3, D4, E1, E2, E3, and E4; wherein a virtual cross-sectional plane is perpendicular to a central longitudinal axis of the leg-associated portion, wherein a virtual circumference is a circle which most closely fits the intersection of the leg-associated portion with a virtual cross-sectional plane, wherein a 0-degree point on a virtual circumference is the most forward point of the circumference when the person stands with arms and legs extended outwards (in a Vitruvian Man manner); wherein a 90-degree point on a virtual circumference is one-quarter of the circumference clockwise (outward) from the 0-degree point, a 180-degree point on a virtual circumference is one-quarter of the circumference clockwise from the 90-degree point, and a 270-degree point on a virtual circumference is one-quarter of the circumference clockwise from the 180-degree point; wherein virtual 0-degree, 90-degree, 180-degree, and 270-degree longitudinal lines for the leg-associated portion can be defined by connecting 0-degree, 90-degree, 180-degree, and 270-degree points, respectively, across a longitudinal sequence of virtual circumferences; wherein a 1st radial-quadrant arcuate area is clockwise between the 0-degree and 90-degree longitudinal lines, wherein a 2nd radial-quadrant arcuate area is clockwise between the 90-degree and 180-degree longitudinal lines, wherein a 3rd radial-quadrant arcuate area is clockwise between the 180-degree and 270-degree longitudinal lines, and wherein a 4th radial-quadrant arcuate area is clockwise between the 270-degree and 0-degree longitudinal lines; * wherein the leg-associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area;
* wherein the leg-associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and * wherein changes in the flow of energy through the first flexible energy pathway and changes in the flow of energy through the second flexible energy pathway are analyzed jointly to measure changes in body motion and/or configuration.

In an example, an article of clothing can be an upper-body article of clothing such as a long-sleeve shirt or jacket. In an example, an article of clothing can be a lower-body article of clothing such as a full-length pair of pants. In an example, an article of clothing can be a full-body article of clothing such as a full-body suit, leotard, and/or uniform. In an example, a flexible arcuate energy pathway can be printed on clothing (using electroconductive ink), adhered to clothing (using an adhesive), or attached to clothing (using heat). In an example, a flexible arcuate energy pathway can be created by etching and/or melting with a laser. In an example, a flexible arcuate energy pathway can be woven into fabric, sewn into fabric, and/or embroidered onto fabric. In an example, a flexible arcuate energy pathway can be inserted into channels or pockets in clothing. In an example, a flexible arcuate energy pathway can be attached to clothing using snaps, buttons, pins, plugs, hooks, or hook-and-eye material.

In an example, a flexible arcuate energy pathway can be an electroconductive pathway which transmits electromagnetic energy. In an example, bending, stretching, elongation, and/or compression of a flexible arcuate energy pathway changes the flow of electromagnetic energy through the pathway. In an example, bending, stretching, elongation, and/or compression of a flexible arcuate energy pathway changes the resistance of the pathway which changes the flow of electromagnetic energy through the pathway. In an example, a flexible arcuate energy pathway can be an electroconductive fiber, yarn, thread, strip, wire, or layer. In an example, a flexible arcuate energy pathway can have a wavy, undulating, sinusoidal, oscillating, and/or zigzag configuration. In an example, a flexible arcuate energy pathway can be elastic. In an example, the flow of electromagnetic energy through a flexible arcuate energy pathway can be measured using an electromagnetic energy sensor.

In an example, a flexible arcuate energy pathway can have a convex proximal portion and a concave distal portion, or vice versa. In an example, a flexible arcuate energy pathway can have an "S" shape. In an example, a plurality of flexible arcuate energy pathways can diverge and fan out like a feather or the veins of a leaf. In an example, a plurality of flexible arcuate energy pathways has a nested configuration. In an example, proximal portions of a plurality of flexible arcuate energy pathways can be approximately parallel and distal portions of the plurality of flexible arcuate energy pathways can diverge and fan out. In an example, distal portions of a plurality of flexible arcuate energy pathways can be approximately parallel and proximal portions of the plurality of flexible arcuate energy pathways can diverge and fan out. In an example, proximal portions of a plurality of flexible arcuate energy pathways can have a shared point of origin or intersection and distal portions of the plurality of flexible arcuate energy pathways can diverge and fan out. In an example, distal portions of a plurality of flexible arcuate energy pathways can have a shared point of origin and proximal portions of the plurality of flexible arcuate energy pathways can diverge and fan out.

In an example, a flexible arcuate energy pathway can comprise an electroconductive fiber, yarn, thread, strand, substrate, layer, or textile. In an example, a flexible arcuate energy pathway can comprise a plurality of electroconductive fibers, yarns, threads, strands, substrates, layers, or textiles. In an example, a flexible arcuate energy pathway can be comprised of two or more layers of conductive fibers, yarns, threads, strands, substrates, layers, or textiles. In an example, a flexible arcuate energy pathway can be comprised of alternating layers of conductive and non-conductive fibers, yarns, threads, strands, substrates, layers, or textiles. In an example, stretching, elongation, bending, twisting, or compression of a multi-layer flexible arcuate energy pathway changes the proximity of the layers which, in turn, changes the flow of electromagnetic energy through the pathway. In an example, stretching, elongation, bending, twisting, or compression of a multi-layer flexible arcuate energy pathway changes the proximity of the conductive layers to each other which, in turn, changes the flow of electromagnetic energy through the pathway.

In an example, changes in the flow of electromagnetic energy through a flexible arcuate energy pathway can be measured by one or more parameters selected from the group consisting of: amperage, capacitance, conductivity, current, electromagnetic wave pattern, impedance, phase, resistance, and voltage. In an example, material used for forming, coating, and/or impregnating a flexible arcuate energy pathway can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, a flexible arcuate energy pathway can be an optical pathway which transmits light energy. In an example, bending, stretching, elongation, and/or compression of a flexible arcuate energy pathway changes the amount, frequency, spectrum, polarization, phase, and/or coherence of light energy transmitted through an optical energy pathway. In an example, a flexible arcuate energy pathway can be a fiber optic channel In an example, coherent light energy can be transmitted through a flexible optical energy pathway. In an example, the transmission of light energy through a flexible arcuate energy pathway can be measured using a photometer or spectroscopic sensor.

In an example, a flexible arcuate energy pathway can be an acoustic pathway which transmits sound energy. In an example, bending, stretching, elongation, and/or compression of a flexible arcuate energy pathway changes the amount, frequency, or pattern of sound energy transmitted through an acoustic energy pathway. In an example, ultrasonic energy can be transmitted through a flexible acoustic pathway. In an example, the transmission of sound energy through a flexible arcuate energy pathway can be measured using a microphone.

In an example, a flexible arcuate energy pathway can be a helix or a portion of a helical and/or spiral loop. In an example, the central longitudinal axis of a flexible arcuate energy pathway can be a helix or a portion of a helical and/or spiral loop. In an example, a flexible arcuate energy pathway can have sinusoidal or other undulations around its central longitudinal axis. In an example, a flexible arcuate energy pathway can be entirely on one side (e.g. within two adjacent radial-quadrants) of an arm or leg. In an example, a flexible arcuate energy pathway can be a portion of a helical and/or spiral loop which is less than a half loop. In an example, a flexible arcuate energy pathway can span both sides (e.g. three or all four radial quadrants) of an arm or leg. In an example, a flexible arcuate energy pathway can be a portion of a helical and/or spiral loop which includes more than a half loop. In an example, a flexible arcuate energy pathway can be a portion of a helix and/or spiral which includes a complete loop.

In an example, two flexible arcuate energy pathways can converge proximally and diverge distally. In an example, two energy pathways spanning an arm (or leg) can both start in proximal locations in the same radial quadrant, diverge distally, and end in two different distal locations on the arm (or leg) in one or more different radial quadrants. Spanning multiple radial quadrants can help to measure the rotation, torsion, and/or twisting of an arm (or leg) as well as bending of the arm (or leg). In an example, first and second flexible arcuate energy pathways can start within area E1, the first pathway can extend to area A4, and the second pathway can extend to area B4. In an example, first and second flexible arcuate energy pathways can start within area E4, the first pathway can extend to area A1, and the second pathway can extend to area B1. In an example, similar (e.g. symmetric or mirror-image) pathways can span the rear of an arm (or leg) in addition to (or instead of) front pathways, with the 2nd and 3rd radial quadrants substituting for the 1st and 4th radial quadrants.

In an example, two flexible arcuate energy pathways can converge distally and diverge proximally. In an example, two energy pathways spanning an arm (or leg) can start in distal locations in the same radial quadrant, diverge proximally, and end in two different proximal locations in one or more different radial quadrants. Again, spanning multiple radial quadrants can help to measure rotation, torsion, and/or twisting of an arm (or leg) as well as bending of the arm (or leg). In an example, first and second flexible arcuate energy pathways can start within area A1, the first pathway can extend to area D4, and the second pathway can extend to area E4. In an example, first and second flexible arcuate energy pathways can start within area A4, the first pathway can extend to area D1, and the second pathway can extend to area E1. In an example, similar (e.g. symmetric or mirror-image) pathways can span the rear of an arm (or leg) in addition to (or instead of) front pathways, with the 2nd and 3rd radial quadrants substituting for the 1st and 4th radial quadrants.

In an example, two flexible arcuate energy pathways can converge in a central area of a person's arm (or leg). In an example, two energy pathways on the arm (or leg) can start in central locations in the same radial quadrant, diverge distally and proximally, and end in two different distal and proximal locations in one or more different radial quadrants. Again, spanning multiple radial quadrants can help to measure rotation, torsion, and/or twisting of an arm (or leg) as well as bending of the arm (or leg). In an example, first and second flexible arcuate energy pathways can start within area C1, the first pathway can extend to area A4, and the second pathway can extend to area E4. In an example, first and second flexible arcuate energy pathways can start within area C4, the first pathway can extend to area A1, and the second pathway can extend to area E1. In an example, similar (e.g. symmetric or mirror-image) pathways can span the rear of an arm (or leg) in addition to (or instead of) front pathways, with the 2nd and 3rd radial quadrants substituting for the 1st and 4th radial quadrants.

In an example, two flexible arcuate energy pathways can span more than two radial-quadrants of an arm (or leg). In an example, these pathways can comprise full or partial helical loops. In an example, two energy pathways can start in proximal locations in the same radial quadrant on the front of the arm (or leg), diverge proximally, and end in two different proximal locations in one or more different radial quadrants on the rear of the arm (or leg). Spanning three or all four radial quadrants (and sides) can help to measure rotation, torsion, and/or twisting of an arm (or leg) as well as bending of the arm (or leg). In an example, first and second flexible arcuate energy pathways can start within front area E4, the first pathway can extend clockwise around the arm to rear area B3, and the second pathway can extend clockwise around the arm to rear area A3. In an example, first and second flexible arcuate energy pathways can start within front area E1, the first pathway can extend clockwise around the arm to rear area B2, and the second pathway can extend clockwise around the arm to rear area A2. In an example, similar (e.g. symmetric or mirror-image) pathways can be created with the roles of 2nd and 3rd radial quadrants being switched with those of 1st and 4th radial quadrants.

In an example, the geometric relationship between the longitudinal axis of a first flexible arcuate energy pathway and the longitudinal axis of a second flexible arcuate energy pathway can be selected from the group consisting of: substantially-parallel as they span a distal portion of a joint and diverging as they span a proximal portion of a joint, or vice versa; substantially-parallel as they span a proximal portion of a joint and diverging as they span a distal portion of a joint, or vice versa; forming a rainbow arc configuration; radial vectors with a common point of convergence; and arcuate elements with a common convergence point.

In an example, first and second flexible arcuate energy pathways can be substantially parallel as they span a distal skeletal member of a shoulder joint and diverge in a radial manner as they span a proximal skeletal member of the shoulder joint, or vice versa. In an example, first and second flexible arcuate energy pathways can be substantially parallel as they span the humerus and diverge as they span the acromion, clavicle, coracoid process, and/or scapula, or vice versa. In an example, the first and second flexible arcuate energy pathways can be concentric and/or nested as they span the portion of a person's body which contains a shoulder joint.

In an example, first and second flexible arcuate energy pathways can be substantially parallel as they span a distal skeletal member of an elbow joint and diverge in a radial manner as they span a proximal skeletal member of the elbow joint, or vice versa. In an example, the first and second flexible arcuate energy pathways are substantially parallel as they span the radius and ulna and diverge as they span the humerus, or vice versa. In an example, the first and second flexible arcuate energy pathways can be concentric and/or nested as they span the portion of a person's body which contains an elbow joint.

In an example, first and second flexible arcuate energy pathways can be substantially parallel as they span a distal skeletal member of a hip joint and diverge in a radial manner as they span a proximal skeletal member of the hip joint, or vice versa. In an example, the first and second flexible arcuate energy pathways are substantially parallel as they span the femur and diverge as they span the Ilium, or vice versa. In an example, the first and second flexible arcuate energy pathways can be concentric and/or nested as they span the portion of a person's body which contains a hip joint.

In an example, first and second flexible arcuate energy pathways can be substantially parallel as they span a distal skeletal member of a knee joint and diverge in a radial manner as they span a proximal skeletal member of the knee joint, or vice versa. In an example, the first and second flexible arcuate energy pathways are substantially parallel as they span the tibia and diverge as they span the femur, or vice versa. In an example, the first and second flexible arcuate energy pathways can be concentric and/or nested as they span the portion of a person's body which contains a knee joint.

In an example, first and second flexible arcuate energy pathways can follow converging arcuate vectors. In an example, first and second flexible arcuate energy pathways can be part of a joint-spanning plurality of concentric or progressively-nested arcuate members which are configured to collectively span the surface of a portion of the human body which contains a human body joint.

In an example, different energy pathways, tubes, and/or channels can span the same body joint at different angles. In an example, two energy pathways spanning the same body joint can differ in the angles at which they span the longitudinal axis of the body member which contains the body joint. In an example, having different energy pathways span a body joint at different angles can be especially useful for measuring the motion and/or configuration of ball-and-socket joints or other complex-motion joints. In an example, having different sets of energy pathways, tubes, and/or channels that span a joint at different angles can be especially useful for measuring the multi-angle movements of a ball-and-socket joint (e.g. such as a shoulder or hip). Using different sets of energy pathways, tubes, and/or channels that span a complex body segment or joint (such as a person's wrist, foot, torso, and/or back) at different angles can also be useful for measuring bending or twisting of such a complex body segment or joint.

In an example, having one or more energy pathways, tubes, and/or channels that span a body joint in a spiral and/or helical manner can be advantageous for modeling the movements of a ball-and-socket joint. In an example, having energy pathways, tubes, and/or channels span a body joint in a spiral and/or helical manner can better control for slipping or sliding of the article or accessory with respect to the person's skin as the joint bends. Using different sets of energy pathways, tubes, and/or channels that span a complex body segment or joint (such as a person's wrist, foot, torso, and/or back) at different angles can be useful for measuring bending or twisting of such a complex body segment or joint.

In an example, a first flexible arcuate energy pathway can have a longitudinal axis and a second flexible arcuate energy pathway can have a longitudinal axis, wherein the relationship between these two longitudinal axes can be selected from the group consisting of: arcuate radial vectors with a common point of origin; concentric and/or nested; rainbow arc configuration; substantially-parallel as they span a distal portion of a joint and diverging as they span a proximal portion of a joint, or vice versa; and substantially-parallel as they span a proximal portion of a joint and diverging as they span a distal portion of a joint, or vice versa; intersecting at an acute angle; and arcuate with a common convergence point.

In an example, changes in the flow of energy through a first flexible energy pathway and changes in the flow of energy through a second flexible energy pathway can be analyzed jointly to measure and/or recognize changes in arm (or leg) motion and/or configuration. In this example, there can be two flexible arcuate energy pathways spanning a person's arm (or leg). In an example, there can be three flexible arcuate energy pathways spanning a person's arm (or leg). In an example, there can be four or more flexible arcuate energy pathways spanning a person's arm (or leg). In an example, a flexible arcuate energy pathway can be undulating and/or sinusoidal.

In an example, two or more arcuate energy pathways can converge proximally as one follows them in a distal-to-proximal manner from different arcuate areas along the length of a person's arm (or leg) to a shared arcuate area on person's torso. In an example, two or more arcuate energy pathways can converge distally as one follows them in a proximal-to-distal manner from different arcuate areas on a person's torso to a shared arcuate area on a person's arm (or leg). In an example, two or more arcuate energy pathways can diverge proximally as one follows them in a distal-to-proximal manner from a shared arcuate area on a person's arm (or leg) to different arcuate areas on the person's torso. In an example, two or more arcuate energy pathways can diverge distally as one follows them in a proximal-to-distal manner from a shared arcuate area on person's torso to different arcuate areas along the length of the person's arm (or leg).

In an example, two or more flexible arcuate energy pathways can span from a shared proximal arcuate area (selected from the group consisting of A1, A2, A3, A4, B1, B2, B3, B4, C1, C2, C3, C4, D1, D2, D3, D4, E1, E2, E3, and E4) to different distal arcuate areas (selected from the group consisting of A1, A2, A3, A4, B1, B2, B3, B4, C1, C2, C3, C4, D1, D2, D3, D4, E1, E2, E3, and E4) in one or more radial quadrants (e.g. 1st, 2nd, 3rd, and 4th—identified by the number suffix of an arcuate area) which are different than the radial quadrant (e.g. 1st, 2nd, 3rd, or 4th—identified by the number suffix of an arcuate area) of their shared proximal arcuate area. In an example, two or more flexible arcuate energy pathways can span from a shared distal arcuate area (selected from the group consisting of A1, A2, A3, A4, B1, B2, B3, B4, C1, C2, C3, C4, D1, D2, D3, D4, E1, E2, E3, and E4) to different proximal arcuate areas (selected from the group consisting of A1, A2, A3, A4, B1, B2, B3, B4, C1, C2, C3, C4, D1, D2, D3, D4, E1, E2, E3, and E4) in one or more radial quadrants (e.g. 1st, 2nd, 3rd, and 4th—identified by the number suffix of an arcuate area) which are different than the radial quadrant (e.g. 1st, 2nd, 3rd, or 4th—identified by the number suffix of an arcuate area) of their shared distal arcuate area.

In an example, two or more arcuate energy pathways need not converge to a common point of intersection or origin in order to be classified as converging. In an example, when the distance between two or more arcuate energy pathways shrinks as one follows them in a distal-to-proximal or proximal-to-distal direction, then they are converging. In an example, the convergence of two or more arcuate energy pathways can decrease (proximally or distally) and they become asymptotically parallel to each other. In an example, the distal ends of two or more arcuate energy pathways can converge and become asymptotically parallel to each other. In an example, the proximal ends of two or more arcuate energy pathways can converge and become asymptotically parallel to each other. In an example, two or more arcuate energy pathways can not only converge into a shared arcuate area, but can also converge into a shared point of intersection, point of origin, or point of termination.

In an example, an article of clothing can further comprise energy emitters and sensors. In an example, an article of clothing can further comprise a dedicated energy emitter for each energy pathway to emit energy into that pathway. In an example, an article of clothing can further comprise a dedicated energy sensor for each energy pathway to measure the flow of energy through that pathway. In an example, an article of clothing can further comprise an energy emitter and energy sensor for each energy pathway to measure transmission of emitted energy through the energy pathway. In an example, two or more energy pathways can share the same energy emitter. In an example, two or more energy pathways can share the same energy sensor. In an example, two or more energy pathways can share the same energy sensor, but have separate energy emitters. In an example, two or more energy pathways can share the same energy emitter, but have separate energy sensors.

In an example, an article of smart clothing can further comprise at least one accelerometer and at least one gyroscope in addition to the plurality of flexible arcuate energy pathways. In an example, an accelerometer can be located within an arcuate area selected from the group consisting of: A1, A2, A3, A4, B1, B2, B3, B4, C1, C2, C3, C4, D1, D2, D3, D4, E1, E2, E3, and E4. In an example, an accelerometer can be located within an "A2" or "A3" arcuate area. In an example, a first accelerometer can be located within an "A" segment and a second accelerometer can be located within a "C" segment. In an example, a gyroscope can be located within an arcuate area selected from the group consisting of: A1, A2, A3, A4, B B2, B3, B4, C1, C2, C3, C4, D1, D2, D3, D4, E1, E2, E3, and E4. In an example, a gyroscope can be located within an "A2" or "A3" arcuate area. In an example, a first gyroscope can be located within an "A" segment and a second gyroscope can be located within a "C" segment. In an example, data from at least one accelerometer and data from at least one gyroscope can be analyzed jointly with data from the plurality of flexible arcuate energy pathways in order to more precisely measure body motion and/or configuration.

In an example, an article of clothing can further comprise one or more additional components selected from the group consisting of: inclinometer; compass; power source (such as a battery); energy transducer and/or harvester (which generates electrical energy from kinetic energy or thermal energy); data processor; data transmitter and/or receiver; (touch-activated) display screen; keypad; microphone; and speaker. In an example, data concerning the flows of energy through two or more flexible arcuate energy pathways can be transmitted to a remote data processor where it is analyzed to measure body motion and/or configuration. In an example, a remote data processor can be in a device which is worn by the person wearing the article of clothing. In an example, a remote data processor can be in a hand-held device such as a cell phone.

In an example, a flexible arcuate energy pathway can conduct and/or transmit electromagnetic energy. In an example, a flexible arcuate energy pathway can be piezoelectric. In an example, a flexible arcuate energy pathway can generate electricity when it is bent or stretched. In an example, changes in electricity generated by a piezoelectric flexible arcuate energy pathway can be used to measure body motion and/or changes in body configuration.

In an example, a flexible arcuate energy pathway can be integrated into an article of clothing or attached to an article of clothing by one or more methods selected from the group consisting of: weaving (into clothing fabric), sewing (onto clothing), embroidering (onto clothing), printing (on clothing), adhesion (to clothing), hook-and-eye connection (to clothing), melting (onto clothing), snapping (onto clothing), and inserting into channels (between layers of clothing fabric). In an example, a flexible arcuate energy pathway can be reversibly and/or adjustably attached to an article of clothing so that its location can be changed in order to customize motion recognition clothing for a particular person and/or type of activity. In an example, a flexible arcuate energy pathway can be reversibly removed before an article of clothing is washed.

In an example, smart clothing can comprise (partially) helical arcuate energy pathways which spiral (partially) around a person's arm or leg (from the front to the rear). In an example, smart clothing can further comprise a second set of centrally-converging arcuate energy pathways which are reflected (symmetric) relative to a first set of centrally-converging arcuate energy pathways. In an example, smart clothing can further comprise a second set of centrally-converging arcuate energy pathways which are nested relative to a first set of centrally-converging arcuate energy pathways. In an example, first and second flexible arcuate energy pathways can converge or diverge in a radial manner as they longitudinally span a portion of the person's body.

In an example, electrical energy can be conducted through flexible energy pathways and the amounts of electrical energy conducted can change when the configurations of the pathways change as a portion of the person's body moves. In an example, electrical voltage, current, resistance, and/or impedance can be measured. In an example, electrical energy can be generated by energy pathways when the configurations of pathways change as the portion of the person's body moves. In an example, the energy pathways can be piezoelectric. In an example, first and second energy flows can be light energy. In an example, energy pathways can be fiber optic. In an example, the amount, wavelength, and/or spectrum of light energy transmitted through energy pathways can change when the configurations of the pathways change as the portion of a person's body moves. In an example, first and second energy flows can be sound energy. In an example, energy flows can be ultrasonic. In an example, the amount, frequency, or pattern of sound energy transmitted through energy pathways can change when the shapes of the pathways change.

In an example, joint statistical analysis of first and second energy flows through first and second flexible arcuate energy pathways can provide more accurate estimation, measurement, and/or modeling of abduction, eversion, extension, flexion, inversion, pronation, radial deviation rotation, supination, and/or ulnar deviation of a portion of a person's body than does separate statistical analysis of a first energy flow or a second energy flow. In an example, energy flows from first and second flexible arcuate energy pathways can be averaged together to reduce the variability of measurement and/or reduce the impact of measurement error in one pathway. In an example, a statistical method can be used which gives greater statistical weight to a first energy flow over a first range of abduction, eversion, extension, flexion, inversion, pronation, radial deviation rotation, supination, and/or ulnar deviation and gives greater statistical weight to a second energy flow over a second range of abduction, eversion, extension, flexion, inversion, pronation, radial deviation rotation, supination, and/or ulnar deviation. In an example, a statistical method can analyze differences between first and second energy flows to determine if the locations of the flexible energy pathways relative to the surface of a person's body have shifted and to adjust estimation if such shifting occurs.

In an example, the relationship between energy flows and the motion and/or configuration of a portion of a person's body can be nonlinear and/or stochastic. In an example, joint analysis of first and second energy flows from first and second flexible arcuate energy pathways spanning a portion of a person's body can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; Carlavian curves; chi-squared; eigenvalue decomposition; logit model; machine learning; power spectral density; power spectrum analysis; and/or probit model.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

FIGS. 1 through 17 show some examples of how this invention can be embodied, but do not restrict the full generalizability of the claims. Example and component variations which have been discussed thus far in this disclosure (and also in other disclosures linked by priority claim) can be applied where relevant to the examples in FIGS. 1 through 17 but are not repeated in the narratives accompanying each of these figures in order to reduce duplicative content.

FIG. 1 shows an example of a wearable device for recognizing human motion comprising an article of clothing 1002 that is configured to span a body joint 1001 in which different sets of energy pathways, tubes, and/or channels span the same body joint at different angles with respect to the longitudinal axis of the joint. In this example, a first set of energy pathways, tubes, and/or channels (including energy pathways, tubes, and/or channels 1005 and 1008) span the longitudinal axis of a joint in a manner which is substantially parallel to the longitudinal axis of the joint (especially when the joint is fully extended). In this example, a second set of energy pathways, tubes, and/or channels (including energy pathways, tubes, and/or channels 1006 and 1010) spans the longitudinal axis of the joint at an acute angle with respect to the longitudinal axis of the joint. In this example, a third set of energy pathways, tubes, and/or channels (including energy pathways, tubes, and/or channels 1007 and 1009) spans the longitudinal axis of the joint at a different angle with respect to the longitudinal axis of the joint. This example also includes a power source 1004 and a data transmitter 1003 which are attached to the article of clothing or wearable accessory.

In an example, each of the three different sets of energy pathways, tubes, and/or channels can have greater measurement accuracy over a different range of body joint motion. In an example, incorporating pressure information from all three sets can enable more accurate estimation of body joint angle in this hinge joint than using information from only one set. In an example, different sets of energy pathways, tubes, and/or channels that span a joint at different angles can be used to estimate a single angle of a hinge joint (e.g. a knee in this example).

In another example, different sets of energy pathways, tubes, and/or channels that span a joint at different angles can be especially useful for measuring the multi-angle movements of a ball-and-socket joint (e.g. such as a shoulder or hip). In an example, sets of energy pathways, tubes, and/or channels which span a joint at acute angles can be particularly useful for measuring rotation or twisting of a ball-and-socket joint. Using different sets of energy pathways, tubes, and/or channels that span a complex body segment or joint (such as a person's wrist, foot, torso, and/or back) at different angles can also be useful for measuring bending or twisting of such a complex body segment or joint.

In an example, first and second flexible energy pathways can have longitudinal axes which span a portion of a person's body. In an example, first and second flexible arcuate energy pathways can diverge in a radial manner as they longitudinally span a portion of the person's body. In an example, first and second flexible arcuate energy pathways can be concentric and/or nested as they span a portion of a person's body. In an example, first and second flexible arcuate energy pathways can be pathways within an energy-transmitting mesh which spans a portion of a person's body.

In an example, a wearable device for measuring the configuration or motion of a human body can comprise: (a) a joint-spanning plurality of radial members which are configured to collectively span the surface of a portion of the human body which contains a human body joint, wherein the longitudinal axes of the radial members are configured to converge; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 2:
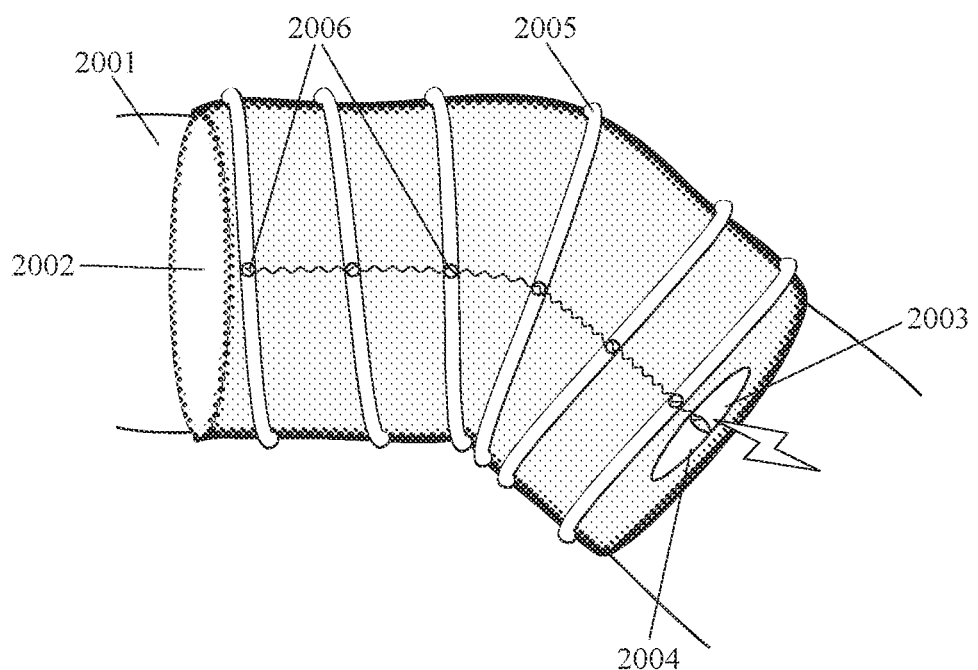
FIG. 2 shows an example of smart clothing with a helical electromagnetic energy pathway spanning a body joint.

FIG. 2 shows an example of a wearable device for recognizing human motion comprising an article of clothing or wearable accessory 2002 that is configured to span a body joint 2001, wherein one or more spiral and/or helical energy pathways, tubes, and/or channels (including spiral and/or helical energy pathway, tube, and/or channel 2005) wrap around the circumference of a body joint. In this example, there are multiple sensors (2006) at different locations on spiral and/or helical energy pathway, tube, and/or channel (2005) which wraps around the circumference of a body joint. Sensor measurements at different locations on spiral and/or helical energy pathway, tube, and/or channel 2005 can provide more accurate measurement of joint movement than a single measure of at one location within the energy pathway, tube, and/or channel In this example, different sensors are aligned along a common (lateral) side of the body joint. In another example, different sensors can be located on different sides of a body joint. This example also includes a power source 2004 and a data transmitter 2003 which are attached to the article of clothing or wearable accessory.

In an example, having one or more energy pathways, tubes, and/or channels span a body joint in a spiral and/or helical manner can increase the surface area of an article of clothing or wearable accessory over which changes can be measured. In an example, having energy pathways, tubes, and/or channels span a body joint in a spiral and/or helical manner can lower the potential for constriction of the person's movement by the energy pathways, tubes, and/or channels.

In an example, having energy pathways, tubes, and/or channels span a body joint in a spiral and/or helical manner can better control for slipping or sliding of the article or accessory with respect to the person's skin as the joint bends. In an example, values in a spiral and/or helical energy pathway, tube, and/or channel can be less affected by circumferential slipping or sliding of an article or accessory than values in a straight energy pathway, tube, and/or channel that spans a joint longitudinally. In an example, having one or more energy pathways, tubes, and/or channels that span a body joint in a spiral and/or helical manner can be advantageous for estimating body joint angle with a looser-fitting article of clothing or wearable accessory. In an example, having one or more energy pathways, tubes, and/or channels that span a body joint in a spiral and/or helical manner can be advantageous for modeling the movements of a ball-and-socket joint.

In an example, a wearable device for measuring the configuration or motion of a human body joint can comprise: (a) a joint-spanning spiral member which is configured to spiral around the surface of a portion of the human body which contains a human body joint; and (b) a plurality of electromagnetic energy sensors which measure electromagnetic energy from different locations on the joint-spanning spiral member, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 3:
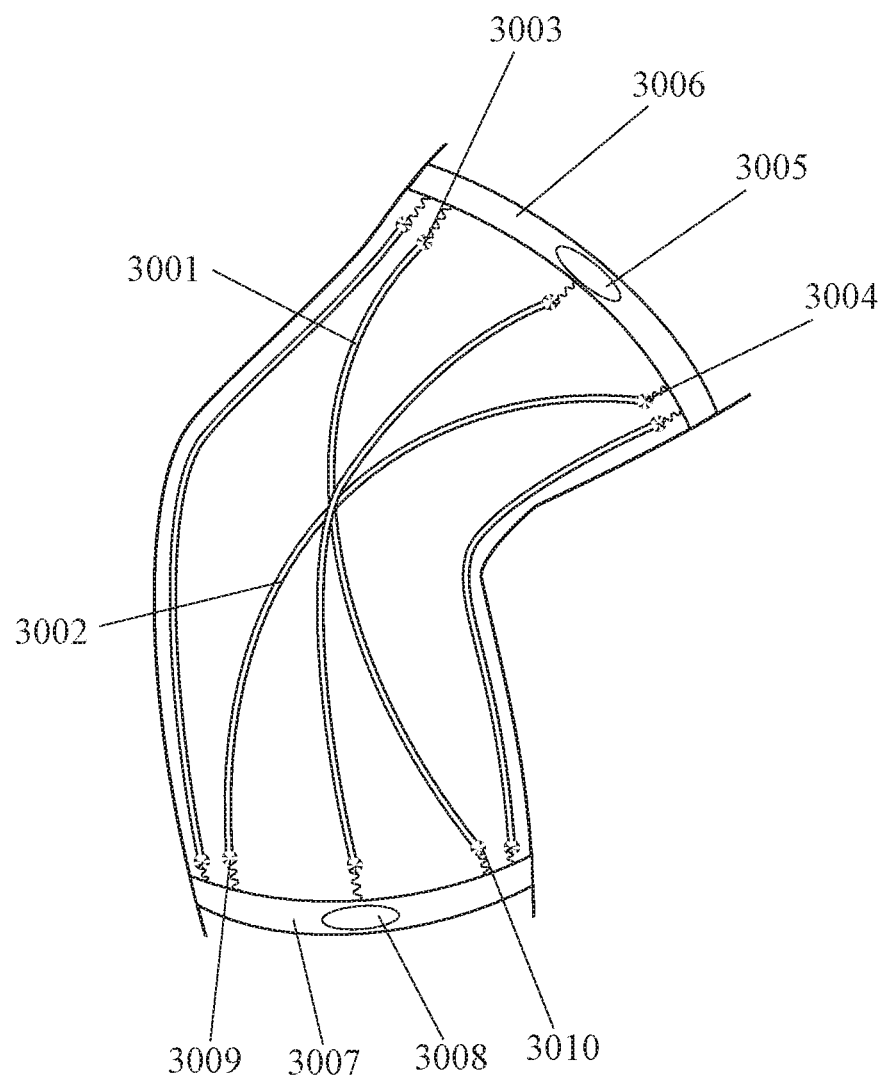
FIG. 3 shows another example of smart clothing with electromagnetic energy pathways spanning a body joint at different angles.

FIG. 3 shows an example of how this invention can be embodied in a wearable device for measuring body joint motion and/or configuration comprising: (a) a first flexible arcuate energy pathway 3001, wherein this first flexible arcuate energy pathway is configured to span the surface of a portion of a person's body which contains at least one body joint at a first angle, wherein this first flexible arcuate energy pathway is moved from a first configuration to a second configuration by movement of the at least one body joint, and wherein this first flexible arcuate energy pathway has a first energy flow when the pathway is in the first configuration and has a second energy flow when the pathway is in the second configuration; (b) a first energy sensor 3003 which measures energy flow through or from the first flexible arcuate energy pathway; (c) a second flexible arcuate energy pathway 3002, wherein this second flexible arcuate energy pathway is configured to span the surface of the portion of a person's body which contains the at least one body joint at a second angle, wherein this second flexible arcuate energy pathway is moved from a third configuration to a fourth configuration by movement of the at least one body joint, and wherein this second flexible arcuate energy pathway has a third energy flow when the pathway is in the third configuration and has a fourth energy flow when the pathway is in the fourth configuration; (d) a second energy sensor 3004 which measures energy flow through or from the second flexible arcuate energy pathway, wherein data from the first energy sensor and data from the second energy sensor are analyzed together in order to measure the motion and/or configuration of the at least one body joint.

As shown in FIG. 3, two energy pathways spanning the same body joint can differ in the angles at which they span the longitudinal axis of the body member which contains the body joint. In an example, having different energy pathways span a body joint at different angles can be especially useful for measuring the motion and/or configuration of ball-and-socket or other complex motion joints.

In the example shown in FIG. 3, this device further comprises: energy input component 3010 which sends energy into the first flexible arcuate energy pathway; energy input component 3009 which sends energy into the second flexible arcuate energy pathway; energy source 3008 (including energy conduits between this source and the energy input components); sensor data control unit 3005 (including energy conduits between this unit and the energy sensors); distal attachment band 3007; and proximal attachment band 3006.

FIG. 3 shows an example embodiment of this invention comprising a wearable device for measuring the configuration or motion of a human body joint can comprise: (a) a first longitudinal member which is configured to longitudinally span the surface of a portion of the human body which contains a human body joint; (b) a first longitudinal electromagnetic energy sensor which measures electromagnetic energy from the first longitudinal member, wherein changes in the configuration or motion of the first longitudinal member change the electromagnetic energy measured by the first longitudinal electromagnetic energy sensor; (c) a second longitudinal member which is configured to longitudinally span the surface of a portion of the human body which contains a human body joint; (d) a second longitudinal electromagnetic energy sensor which measures electromagnetic energy from the second longitudinal member, wherein changes in the configuration or motion of the second longitudinal member change the electromagnetic energy measured by the first longitudinal electromagnetic energy sensor; (e) a first diagonal member which is configured to span the surface of a portion of the human body which contains a human body joint in a manner which is substantially diagonal to the first and/or second longitudinal members; (f) a first diagonal electromagnetic energy sensor which measures electromagnetic energy from the first diagonal member, wherein changes in the configuration or motion of the first diagonal member change the electromagnetic energy measured by the first diagonal electromagnetic energy sensor; (g) a second diagonal member which is configured to span the surface of a portion of the human body which contains a human body joint in a manner which is substantially diagonal to the first and/or second longitudinal members; (h) a second diagonal electromagnetic energy sensor which measures electromagnetic energy from the second diagonal member, wherein changes in the configuration or motion of the second diagonal member change the electromagnetic energy measured by the first diagonal electromagnetic energy sensor, and wherein data from the first longitudinal electromagnetic energy sensor, the second longitudinal electromagnetic energy sensor, the first diagonal electromagnetic energy sensor, and the second diagonal electromagnetic energy sensor are jointly analyzed to estimate the configuration or motion of the human body joint; and (i) an attachment member which holds the first longitudinal member, the second longitudinal member, the first diagonal member, and the second diagonal member within 1" of the surface of the portion of the human body which contains the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 4:
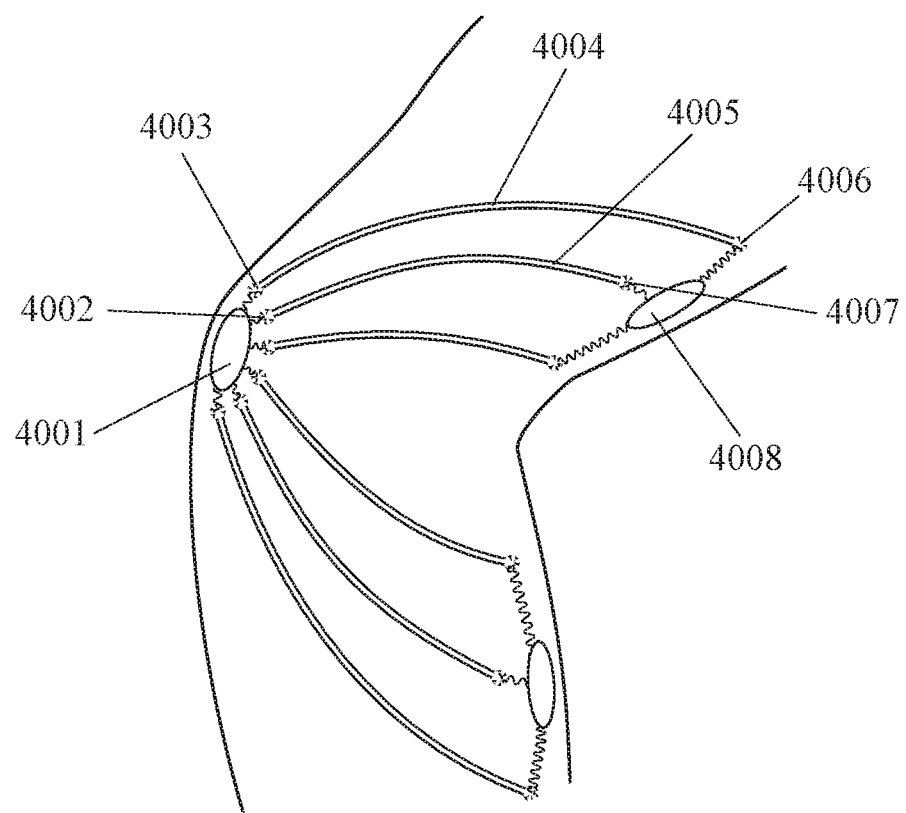
FIG. 4 shows an example of smart clothing with radial electromagnetic energy pathways spanning a body joint.

FIG. 4 shows an example of how this invention can be embodied in a wearable device for measuring body joint motion and/or configuration comprising: (a) a first flexible arcuate energy pathway 4004, wherein this first flexible arcuate energy pathway is configured to span the surface of a portion of a person's body which contains at least one body joint, wherein this first flexible arcuate energy pathway is moved from a first configuration to a second configuration by movement of the at least one body joint, and wherein this first flexible arcuate energy pathway has a first energy flow when the pathway is in the first configuration and has a second energy flow when the pathway is in the second configuration; (b) a first energy sensor 4006 which measures energy flow through or from the first flexible arcuate energy pathway; (c) a second flexible arcuate energy pathway 4005, wherein this second flexible arcuate energy pathway is configured to span the surface of the portion of a person's body which contains the at least one body joint at a second angle, wherein this second flexible arcuate energy pathway is moved from a third configuration to a fourth configuration by movement of the at least one body joint, wherein this second flexible arcuate energy pathway has a third energy flow when the pathway is in the third configuration and has a fourth energy flow when the pathway is in the fourth configuration, and wherein the first and second flexible arcuate energy pathways follow converging arcuate vectors; (d) a second energy sensor 4007 which measures energy flow through or from the second flexible arcuate energy pathway, wherein data from the first energy sensor and data from the second energy sensor are analyzed together in order to measure the motion and/or configuration of the at least one body joint.

In the example shown in FIG. 4, this device further comprises: energy input component 4003 which sends energy into the first flexible arcuate energy pathway; energy input component 4002 which sends energy into the second flexible arcuate energy pathway; energy source 4001 (including energy conduits between this source and the energy input components); and sensor data control unit 4008 (including energy conduits between this unit and the energy sensors).

FIG. 4 shows an example embodiment of this invention comprising a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge at a point on the ventral surface of the portion of the human body which contains the human body joint; and (b) a plurality of electromagnetic energy sensors which measure electromagnetic energy from different locations on the joint-spanning plurality of radial members, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 5:
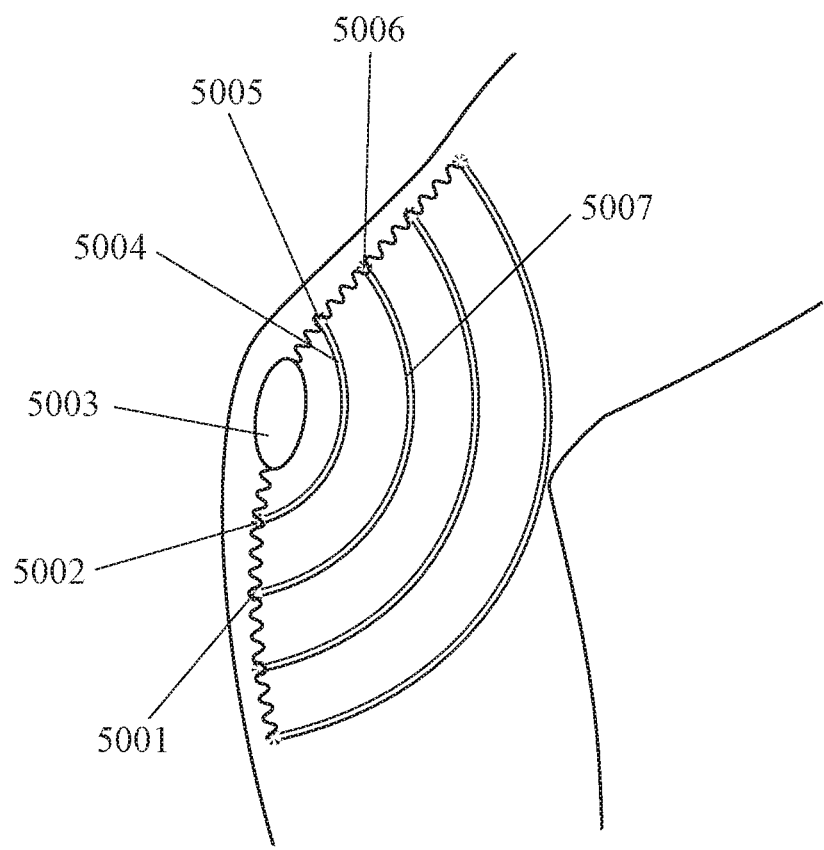
FIG. 5 shows an example of smart clothing with concentric and/or nested electromagnetic energy pathways spanning a body joint.

FIG. 5 shows an example of how this invention can be embodied in a wearable device for measuring body joint motion and/or configuration comprising: (a) a first flexible arcuate energy pathway 5004, wherein this first flexible arcuate energy pathway is configured to span the surface of a portion of a person's body which contains at least one body joint, wherein this first flexible arcuate energy pathway is moved from a first configuration to a second configuration by movement of the at least one body joint, and wherein this first flexible arcuate energy pathway has a first energy flow when the pathway is in the first configuration and has a second energy flow when the pathway is in the second configuration; (b) a first energy sensor 5005 which measures energy flow through or from the first flexible arcuate energy pathway; (c) a second flexible arcuate energy pathway 5007, wherein this second flexible arcuate energy pathway is configured to span the surface of the portion of a person's body which contains the at least one body joint, wherein the first flexible arcuate energy pathway and the second flexible arcuate energy pathway comprise a nested or rainbow-shaped combined configuration; wherein this second flexible arcuate energy pathway is moved from a third configuration to a fourth configuration by movement of the at least one body joint, and wherein this second flexible arcuate energy pathway has a third energy flow when the pathway is in the third configuration and has a fourth energy flow when the pathway is in the fourth configuration; (d) a second energy sensor 5006 which measures energy flow through or from the second flexible arcuate energy pathway, wherein data from the first energy sensor and data from the second energy sensor are analyzed together in order to measure the motion and/or configuration of the at least one body joint.

In the example shown in FIG. 5, this device further comprises: energy input component 5002 which sends energy into the first flexible arcuate energy pathway; energy input component 5001 which sends energy into the second flexible arcuate energy pathway; and combined energy source and sensor data control unit 5003.

FIG. 5 shows an example embodiment of this invention comprising a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on the ventral surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on the dorsal surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 6:
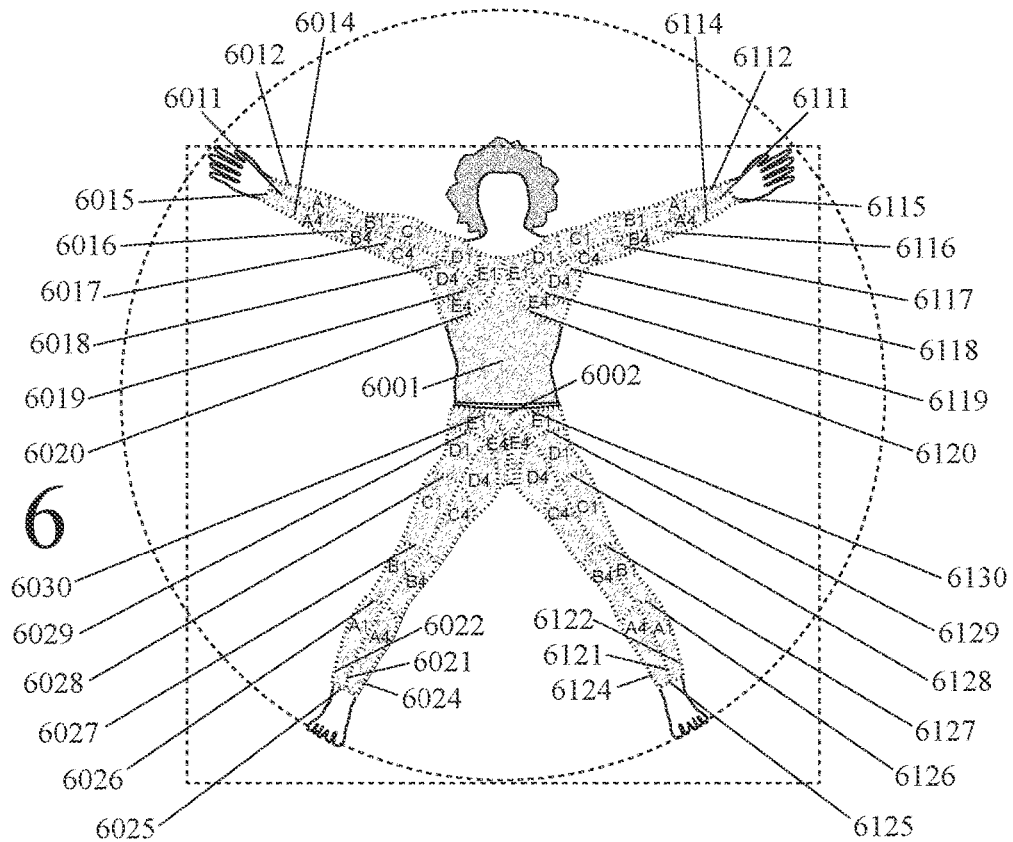
FIGS. 6 and 7 show a virtual locational framework defining twenty arcuate surface areas on a person's arms and legs when extended in the configuration made famous by Leonardo da Vinci's "Vitruvian Man."
Figure 7:
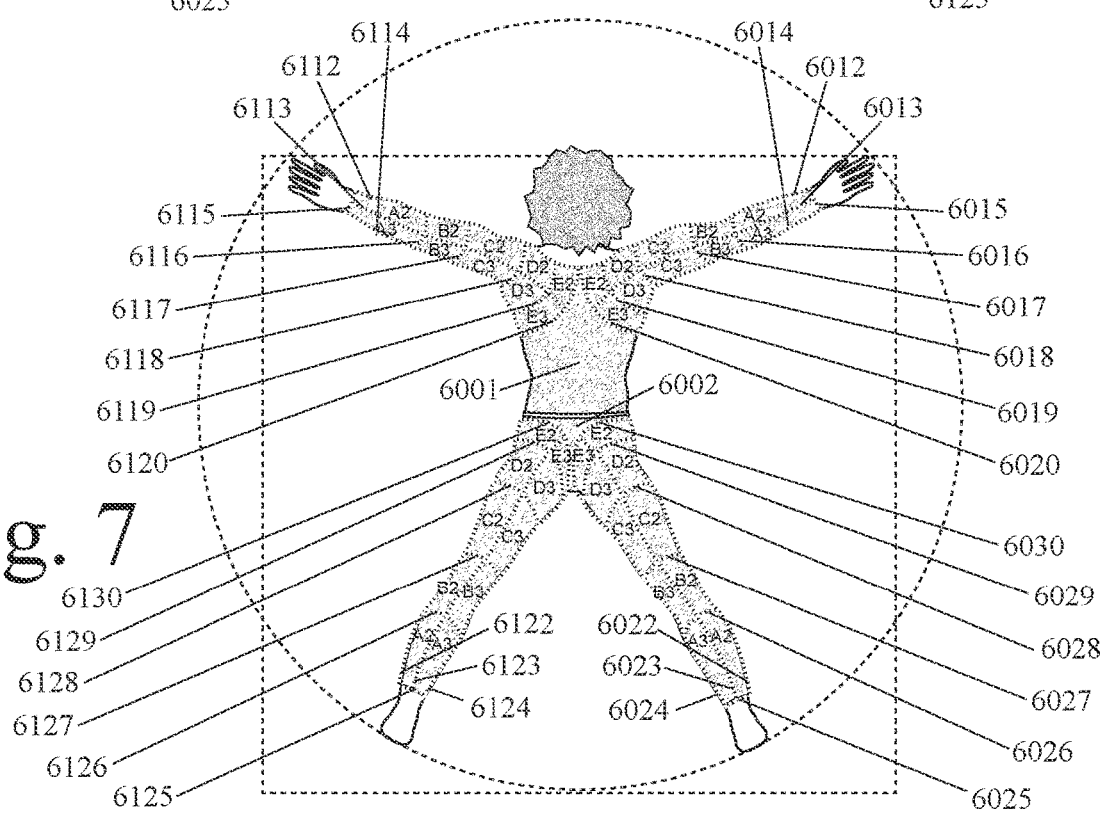

FIGS. 6 and 7 show a virtual locational framework which defines twenty arcuate surface areas on each arm and leg which are used to more-precisely specify embodiments of this invention. FIG. 6 shows a front view of a man with his arms and legs extended outwards in the manner made famous by Leonardo da Vinci's "Vitruvian Man," including the circle and square (shown here with dotted lines) which he used. FIG. 7 shows a rear view of this man. In these figures, the man is wearing an upper-body article of clothing 6001 (e.g. a long-sleeve shirt) and a lower-body article of clothing 6002 (e.g. a pair of pants). Proximal is defined herein as being closer to the man's heart (or torso centroid) and distal is defined as being farther from the man's heart (or torso centroid) when the man's arms and legs are extended outwards in a Vitruvian Man manner.

The locational framework shown in FIGS. 6 and 7 longitudinally divides up the surface of a person's arm (including an adjacent portion of their torso) or leg (including an adjacent portion of their torso) into five distal-to-proximal segments (A, B, C, D, and E) and then radially sub-divides each segment into four radial-quadrant arcuate surface areas (1st, 2nd, 3rd, and 4th), thereby creating a total of twenty arcuate surface areas associated with each arm or leg. Each surface area has a letter-plus-number label (e.g. "A1") with the letter prefix designating the segment (e.g. "A") and the number suffix designating the radial quadrant (e.g. "1").

For an arm, segment B contains (and/or spans) the person's elbow and segment D contains (and/or spans) the person's shoulder. Segment A is distal relative to segment B, segment C is between segment B and segment D, and segment E is proximal relative to segment D (including an adjacent portion of the person's torso). In an example, segment E can have a length between one inch and one foot. In an example, the proximal boundary of segment E can extend into a person's torso by a distance between one inch and one foot. In an example the proximal boundary of segment E can extend from the centroid of a shoulder joint by a radial distance between one inch and one foot. In example, the proximal boundary of segment E can span from the proximal end of a shoulder joint to the central (bisecting) longitudinal axis of the person's torso.

In an example, a series of virtual cross-sectional planes can be defined for an arm, wherein each virtual cross-sectional plane is perpendicular to the central distal-to-proximal longitudinal axis of the arm. In an example, a virtual cross-sectional circumference can be defined as the circle in the virtual cross-sectional plane which most closely fits the article of clothing in the virtual cross-sectional plane. In an example, closeness-of-fit can be done using least squares estimation. In an example, the distal cross-sectional plane of segment B can be tangential to the distal point of the person's elbow joint and the proximal cross-sectional plane of segment B can be tangential to the proximal point of the person's elbow joint. In an example, the distal cross-sectional plane of segment D can be tangential to the distal point of the person's shoulder joint and the proximal cross-sectional plane of segment D can be tangential to the proximal point of the person's shoulder joint.

For a leg, segment B contains (and/or spans) the person's knee and segment D contains (and/or spans) the person's hip. Segment A is distal relative to segment B, segment C is between segment B and segment D, and segment E is proximal relative to segment D (including an adjacent portion of the person's torso). In an example, segment E can have a length between one inch and one foot. In an example, the proximal boundary of segment E can extend into a person's torso by a distance between one inch and one foot. In an example the proximal boundary of segment E can extend from the centroid of a hip joint by a radial distance between one inch and one foot. In example, the proximal boundary of segment E can span from the proximal end of a hip joint to the lower boundary of a person's rib cage.

In an example, a series of virtual cross-sectional planes can be defined for a leg, wherein each virtual cross-sectional plane is perpendicular to the central distal-to-proximal longitudinal axis of the leg. In an example, a virtual cross-sectional circumference can be defined as the circle in the virtual cross-sectional plane which most closely fits the article of clothing in the virtual cross-sectional plane. In an example, closeness-of-fit can be done using least squares estimation. In an example, the distal cross-sectional plane of segment B can be tangential to the distal point of the person's knee joint and the proximal cross-sectional plane of segment B can be tangential to the proximal point of the person's knee joint. In an example, the distal cross-sectional plane of segment D can be tangential to the distal point of the person's hip joint and the proximal cross-sectional plane of segment D can be tangential to the proximal point of the person's hip joint.

In an example, the five segments (A, B, C, D, and E) can have equal lengths. In an example, segments A, B, C, D can have equal lengths. In an example, segments A and C can have equal lengths. In an example, the length of the longest of the five segments can be no more than twice the length of the shortest of the five segments. In an example, each of the five segments (A, B, C, D, and E) can be at least two inches in length. In an example, each of the five segments (A, B, C, D, and E) can be at least four inches in length. In an example, segment E can be between one inch and one foot in length. In an example, segment E can have an arcuate proximal boundary which is a distance between one inch and one foot from the centroid of a shoulder or hip joint.

In an example, compass coordinates (points) can be defined for a virtual cross-sectional circumference (circle) of an arm or leg. In an example, a 0-degree point can be defined as the point on a virtual cross-sectional circumference (circle) which is most forward when a person has their arms and legs extended outwards in a Vitruvian Man manner such as that shown in FIGS. 6 and 7. The 90-degree point can be defined by moving one-quarter of the way clockwise around the virtual cross-sectional circumference (circle) toward the uppermost point for an arm or the outermost point for a leg. The 180-degree and 270-degree points can also be defined by moving further in the same direction around the virtual cross-sectional circumference (circle), one-quarter of the circumference at a time. In this manner, 0, 90, 180, and 270 degree points can divide a virtual cross-sectional circumference (circle) into quadrants. Further, 0, 90, 180, and 270 degree points can be defined for each of the virtual cross-sectional circumferences (circles) along the longitudinal distal-to-proximal axis of an arm or leg.

A 0-degree longitudinal line for an arm or leg can be defined as the line which connects the 0-degree points of the virtual cross-sectional circumferences of the arm or leg (extended onto an adjacent portion of the torso). A 90-degree longitudinal line for an arm or leg can be defined as the line which connects the 90-degree points of the virtual cross-sectional circumferences of the arm or leg (extended onto an adjacent portion of the torso). A 180-degree longitudinal line for an arm or leg can be defined as the line which connects the 180-degree points of the virtual cross-sectional circumferences of the arm or leg (extended onto an adjacent portion of the torso). A 270-degree longitudinal line for an arm or leg can be defined as the line which connects the 270-degree points of the virtual cross-sectional circumferences of the arm or leg (extended onto an adjacent portion of the torso).

The four radial-quadrant arcuate surface areas (1st, 2nd, 3rd, and 4th) of a longitudinal segment can be defined using the 0-degree, 90-degree, 180-degree, and 270-degree lines defined above. The first (1st) arcuate surface area can span the first quadrant of a longitudinal segment (A, B, C, D, or E) clockwise between the 0-degree line and the 90-degree line. The second (2nd) arcuate surface area can span the second quadrant of a longitudinal segment (A, B, C, D, or E) clockwise between the 90-degree line and the 180-degree line. The third (3rd) arcuate surface area can span the third quadrant of a longitudinal segment (A, B, C, D, or E) clockwise between the 180-degree line and the 270-degree line. The fourth (4th) arcuate surface area can span the fourth quadrant of a longitudinal segment (A, B, C, D, or E) clockwise between the 270-degree line and the 0-degree line.

Sub-dividing the five segments of an arm or leg into radial-quadrant arcuate surface areas in the above manner creates twenty areas (A1, A2, A3, A4, B1, B2, B3, B4, C1, C2, C3, C4, D1, D2, D3, D4, E1, E2, E3, and E4). These twenty areas for each arm or leg are labeled in FIGS. 6 and 7. The sequence of letter coordinates (A through E) moves up the arm or leg in a distal-to-proximal direction. The sequence of number coordinates (1 through 4) moves clockwise around the arm or leg in a circumferential manner. This framework of radial-quadrant arcuate surface areas is especially useful for specifying configurations of stretching and/or bending sensors which measure twisting and/or rotation of an arm or leg in addition to simple bending of the arm or leg. This is particularly important for measuring the complex motion of a ball-and-socket joint such as a shoulder or hip.

FIGS. 6 and 7 show an example of how five segments (A, B, C, D, and E) can be created and how each segment can be sub-divided into four (1st, 2nd, 3rd, and 4th) radial-quadrant arcuate surface areas, thereby creating twenty arcuate surface areas (A1, A2, A3, A4, B1, B2, B3, B4, C1, C2, C3, C4, D1, D2, D3, D4, E1, E2, E3, and E4) associated with each arm or leg. Segment A for an arm or leg spans from the distal end (6015, 6025, 6115, or 6125) of an article of clothing on the arm or leg, respectively, to a virtual cross-sectional plane (6016, 6026, 6116, or 6126) at the distal end of an elbow or knee, respectively. Segment B for the arm or leg spans from the virtual cross-sectional plane (6016, 6026, 6116, or 6126) at the distal end of the elbow or knee to a virtual cross-sectional plane (6017, 6027, 6117, or 6127) at the proximal end of the elbow or knee, respectively.

Segment C for the arm or leg spans from the virtual cross-sectional plane (6017, 6027, 6117, or 6127) at the proximal end of the elbow or knee to a virtual cross-sectional plane (6018, 6028, 6118, or 6128) at the distal end of the shoulder or hip, respectively. Segment D for the arm or leg spans from the virtual cross-sectional plane (6018, 6028, 6118, or 6128) at the distal end of the shoulder or hip to a virtual cross-sectional plane (6019, 6029, 6119, or 6129) at the proximal end of the shoulder or hip, respectively. Segment E for the arm or leg spans from the virtual cross-sectional plane (6019, 6029, 6119, or 6129) at the proximal end of the shoulder or hip to a virtual plane (6020, 6030, 6120, or 6130) in a portion of the torso adjacent to the arm or leg, respectively.

FIGS. 6 and 7 also show: 0-degree lines 6011, 6021, 6111, and 6121 for the right arm, right leg, left arm, and left leg, respectively; 90-degree lines 6012, 6022, 6112, and 6122 for the right arm, right leg, left arm, and left leg, respectively; 180-degree lines 6013, 6023, 6113, and 6123 for the right arm, right leg, left arm, and left leg, respectively; and 270-degree lines 6014, 6024, 6114, and 6124 for the right arm, right leg, left arm, and left leg, respectively. As shown in FIGS. 6 and 7, these four lines are used to define four radial-quadrants (1st, 2nd, 3rd, and 4th) for each arm or leg and these four radial-quadrants, in turn, are used to subdivide the five longitudinal segments (A, B, C, D, and E) into four arcuate surfaces per segment. This creates twenty arcuate surface areas (A1, A2, A3, A4, B1, B2, B3, B4, C1, C2, C3, C4, D1, D2, D3, D4, E1, E2, E3, and E4) associated with each arm or leg.

Figure 8:
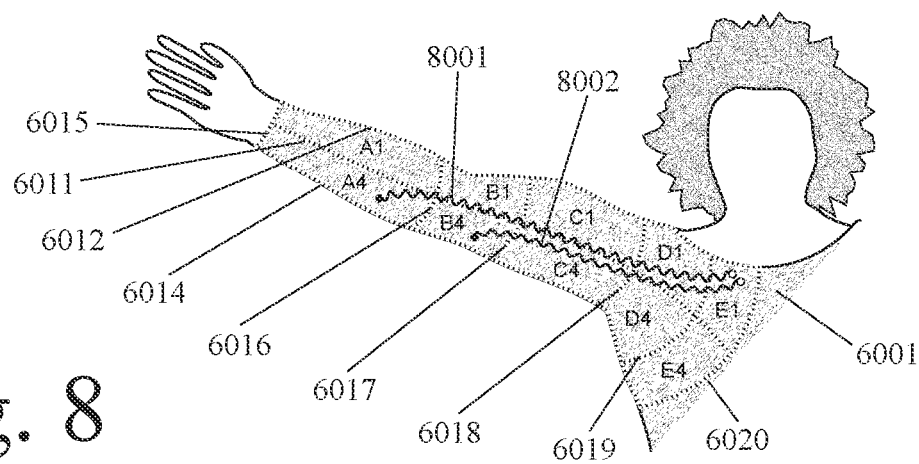
FIG. 8 shows a first example of smart clothing with diverging (partial loop) helical electromagnetic energy pathways on a person's arm.

FIG. 8 shows an example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

FIG. 8 repeats the following components which were introduced in FIGS. 6 and 7: article of clothing 6001; virtual longitudinal lines (0-degree line 6011, 90-degree line 6012, and 270-degree line 6014, wherein 180-degree line 6013 is not visible in this front view); distal end (6015) of the article of clothing; and five virtual cross-sectional planes (6016 at the distal end of the elbow, 6017 at the proximal end of the elbow, 6018 at the distal end of the shoulder, 6019 at the proximal end of the shoulder, and 6020 in a portion of the torso adjacent to the arm). Virtual longitudinal lines and virtual cross-sectional planes were used to define the twenty arcuate surface areas A1, A2, A3, A4, B1, B2, B3, B4, C1, C2, C3, C4, D1, D2, D3, D4, E1, E2, E3, and E4 in FIGS. 6 and 7. Longitudinal lines were used to define four radial-quadrants (1st, 2nd, 3rd, and 4th) for the arm and these four radial-quadrants, in turn, were used to sub-divide five longitudinal segments (A, B, C, D, and E) into four arcuate surfaces per segment. This created twenty arcuate surface areas (Al, A2, A3, A4, B1, B2, B3, B4, C1, C2, C3, C4, D1, D2, D3, D4, E1, E2, E3, and E4) associated with the arm. The specifics of this definition are not repeated for here to avoid redundant content in this disclosure, but can be included in a claim based on this figure.

FIG. 8 also shows: first flexible arcuate energy pathway 8001 which spans from first arcuate area E1 to second arcuate area A4, wherein second arcuate area A4 is in a different longitudinal segment and in a different radial quadrant than first arcuate area E1; and second flexible arcuate energy pathway 8002 which spans from first arcuate area E1 to third arcuate area B4, wherein third arcuate area B4 is in a different longitudinal segment and in a different radial quadrant than first arcuate area E1, and wherein third arcuate area B4 is different than second arcuate area A4.

Changes in the flow of energy through first flexible energy pathway 8001 and changes in the flow of energy through second flexible energy pathway 8002 are analyzed jointly to measure and/or recognize changes in arm motion and/or configuration. In this example, there are two flexible arcuate energy pathways spanning a person's arm. In an example, the can be three flexible arcuate energy pathways spanning a person's arm (or leg). In an example, there can be four or more flexible arcuate energy pathways spanning a person's arm (or leg). In an example, a flexible arcuate energy pathway can be undulating and/or sinusoidal.

In an example, two or more arcuate energy pathways can converge proximally as one follows them in a distal-to-proximal manner from different arcuate areas along the length of a person's arm to a shared arcuate area on person's torso. In an example, two or more arcuate energy pathways can converge distally as one follows them in a proximal-to-distal manner from different arcuate areas on a person's torso to a shared arcuate area on a person's arm. In an example, two or more arcuate energy pathways can diverge proximally as one follows them in a distal-to-proximal manner from a shared arcuate area on a person's arm to different arcuate areas on the person's torso. In an example, two or more arcuate energy pathways can diverge distally as one follows them in a proximal-to-distal manner from a shared arcuate area on person's torso to different arcuate areas along the length of the person's arm.

In an example, two or more flexible arcuate energy pathways can span from a shared proximal arcuate area (selected from the group consisting of A1, A2, A3, A4, B1, B2, B3, B4, C1, C2, C3, C4, D1, D2, D3, D4, E1, E2, E3, and E4) to different distal arcuate areas (selected from the group consisting of A1, A2, A3, A4, B1, B2, B3, B4, C1, C2, C3, C4, D1, D2, D3, D4, E1, E2, E3, and E4) in one or more radial quadrants (e.g. 1st, 2nd, 3rd, and 4th—identified by the number suffix of an arcuate area) which are different than the radial quadrant (e.g. 1st, 2nd, 3rd, or 4th—identified by the number suffix of an arcuate area) of their shared proximal arcuate area. In an example, two or more flexible arcuate energy pathways can span from a shared distal arcuate area (selected from the group consisting of A1, A2, A3, A4, B1, B2, B3, B4, C1, C2, C3, C4, D1, D2, D3, D4, E1, E2, E3, and E4) to different proximal arcuate areas (selected from the group consisting of A1, A2, A3, A4, B1, B2, B3, B4, C1, C2, C3, C4, D1, D2, D3, D4, E1, E2, E3, and E4) in one or more radial quadrants (e.g. 1st, 2nd, 3rd, and 4th—identified by the number suffix of an arcuate area) which are different than the radial quadrant (e.g. 1st, 2nd, 3rd, or 4th—identified by the number suffix of an arcuate area) of their shared distal arcuate area.

In an example, two or more arcuate energy pathways need not converge to a shared point of intersection, point of origin, or point of termination in order to be seen as converging. In an example, when the distance between two or more arcuate energy pathways shrinks as one follows them in a distal-to-proximal or proximal-to-distal direction, then they are converging. In an example, the convergence of two or more arcuate energy pathways can decrease (proximally or distally) and they can become asymptotically parallel to each other. In an example, two or more arcuate energy pathways can not only converge into a shared arcuate area, but can converge into a shared point of intersection, point of origin, or point of termination.

In an example, an article of clothing can further comprise a dedicated energy emitter for each energy pathway to emit energy into that pathway. In an example, an article of clothing can further comprise a dedicated energy sensor for each energy pathway to measure the flow of energy through that pathway. In an example, an article of clothing can further comprise an energy emitter and energy sensor for each energy pathway to measure transmission of emitted energy through the energy pathway. In an example, two or more energy pathways can share the same energy emitter. In an example, two or more energy pathways can share the same energy sensor. In an example, two or more energy pathways can share the same energy sensor, but have separate energy emitters. In an example, two or more energy pathways can share the same energy emitter, but have separate energy sensors.

In an example, an article of clothing can further comprise one or more additional components selected from the group consisting of: accelerometer; gyroscope; inclinometer; compass; EMG sensor; power source (such as a battery); energy transducer and/or harvester (which generates electrical energy from kinetic energy or thermal energy); data processor; data transmitter and/or receiver; (touch-activated) display screen; keypad; lights; microphone; and speaker. In an example, data concerning the flows of energy through two or more flexible arcuate energy pathways can be transmitted to a remote data processor where it is analyzed to measure body motion and/or configuration. In an example, a remote data processor can be in a device which is worn by the person wearing the article of clothing. In an example, a remote data processor can be in a hand-held device such as a cell phone.

In an example, a flexible arcuate energy pathway can conduct and/or transmit electromagnetic energy. In an example, a flexible arcuate energy pathway can be piezoelectric. In an example, a flexible arcuate energy pathway can generate electricity when it is bent or stretched. In an example, changes in electricity generated by a piezoelectric flexible arcuate energy pathway can be used to measure body motion and/or changes in body configuration.

In an example, a flexible arcuate energy pathway can be integrated into an article of clothing or attached to an article of clothing by one or more methods selected from the group consisting of: weaving (into clothing fabric), sewing (onto clothing), embroidering (onto clothing), printing (on clothing), adhesion (to clothing), hook-and-eye connection (to clothing), melting (onto clothing), snapping (onto clothing), and inserting into channels (between layers of clothing fabric). In an example, a flexible arcuate energy pathway can be reversibly and/or adjustably attached to an article of clothing so that its location can be changed in order to customize motion recognition clothing for a particular person and/or type of activity. In an example, a flexible arcuate energy pathway can be reversibly removed before an article of clothing is washed.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 9:
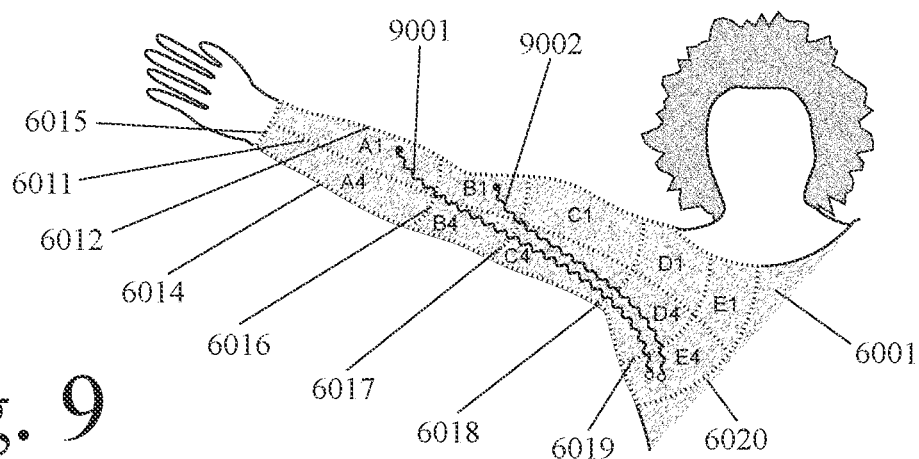
FIG. 9 shows a second example of smart clothing with diverging (partial loop) helical electromagnetic energy pathways on a person's arm.

FIG. 9 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 9 is like the one in FIG. 8 except that the arcuate energy pathways converge proximally at lower locations on the person's torso and diverge distally at higher locations on the person's arm. Specifically, FIG. 9 shows: first flexible arcuate energy pathway 9001 which spans from first arcuate area E4 to second arcuate area A1 and second flexible arcuate energy pathway 9002 which spans from first arcuate area E4 to third arcuate area B1. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 10:
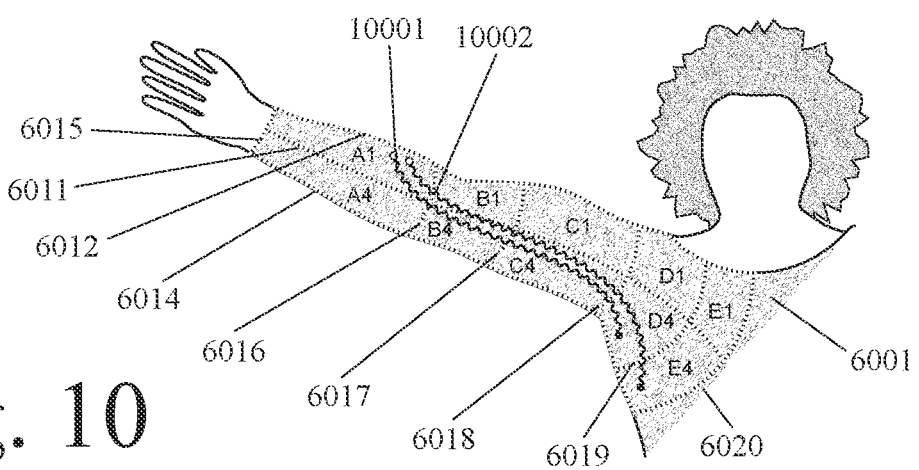
FIG. 10 shows a third example of smart clothing with diverging (partial loop) helical electromagnetic energy pathways on a person's arm.

FIG. 10 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 10 is like the one in FIG. 9 except that the arcuate energy pathways converge distally and diverge proximally. Specifically, FIG. 10 shows: first flexible arcuate energy pathway 10001 which spans from first arcuate area A1 to second arcuate area D4 and second flexible arcuate energy pathway 10002 which spans from first arcuate area A1 to third arcuate area E4. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

FIG. 11 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 11 is like the ones in FIG. 8 through 10 except that arcuate energy pathways converge centrally and diverge distally and proximally. Specifically, FIG. 11 shows: first flexible arcuate energy pathway 11001 which spans from first arcuate area C1 to second arcuate area A4 and second flexible arcuate energy pathway 11002 which spans from first arcuate area C1 to third arcuate area E4. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

FIG. 12 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 12 is like the one in FIG. 9 except that (partially) helical arcuate energy pathways spiral (partially) around the person's arm (from the front to the rear). The upper portion of FIG. 12 shows the front of the arm and the lower portion of FIG. 12 shows the rear of the arm. FIG. 12 shows: first flexible arcuate energy pathway 12001 which spans from front arcuate area E4 to rear arcuate area B3 and second flexible arcuate energy pathway 12002 which spans from front arcuate area E4 to rear arcuate area A3. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 13:
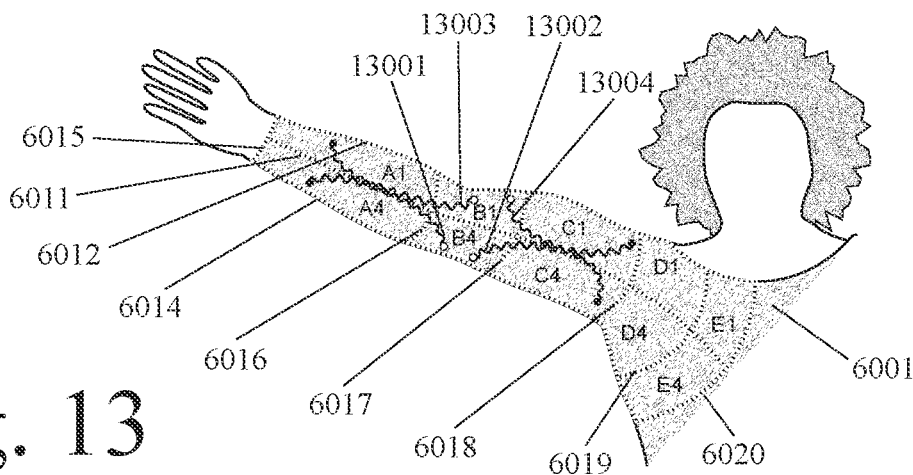
FIG. 13 shows a sixth example of smart clothing with diverging (partial loop) helical electromagnetic energy pathways on a person's arm.

FIG. 13 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 13 is like the one in FIG. 11 except that it is centered on the elbow and includes a second set of centrally-converging arcuate energy pathways which are reflected (symmetric) relative to the first set of centrally-converging arcuate energy pathways. FIG. 13 shows: first flexible arcuate energy pathway 13001 which spans from arcuate area B4 to arcuate area A1; second flexible arcuate energy pathway 13002 which spans from arcuate area B4 to arcuate area C1; third flexible arcuate energy pathway 13003 which spans from arcuate area B1 to arcuate area A4; and fourth flexible arcuate energy pathway 13004 which spans from arcuate area B1 to arcuate area C4. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 14:
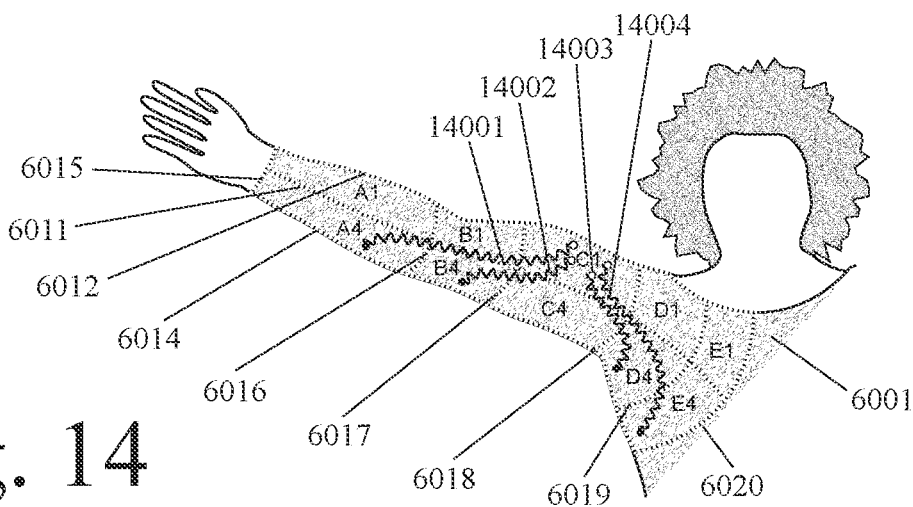
FIG. 14 shows a seventh example of smart clothing with diverging (partial loop) helical electromagnetic energy pathways on a person's arm.

FIG. 14 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 14 is like the one in FIG. 11 except that it includes a second set of centrally-converging arcuate energy pathways which are nested relative to the first set of centrally-converging arcuate energy pathways. FIG. 14 shows: first flexible arcuate energy pathway 14001 which spans from arcuate area C1 to arcuate area A4; second flexible arcuate energy pathway 14002 which spans from arcuate area C1 to arcuate area B4; third flexible arcuate energy pathway 14003 which spans from arcuate area C1 to arcuate area D4; and fourth flexible arcuate energy pathway 14004 which spans from arcuate area C1 to arcuate area E4. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 15:
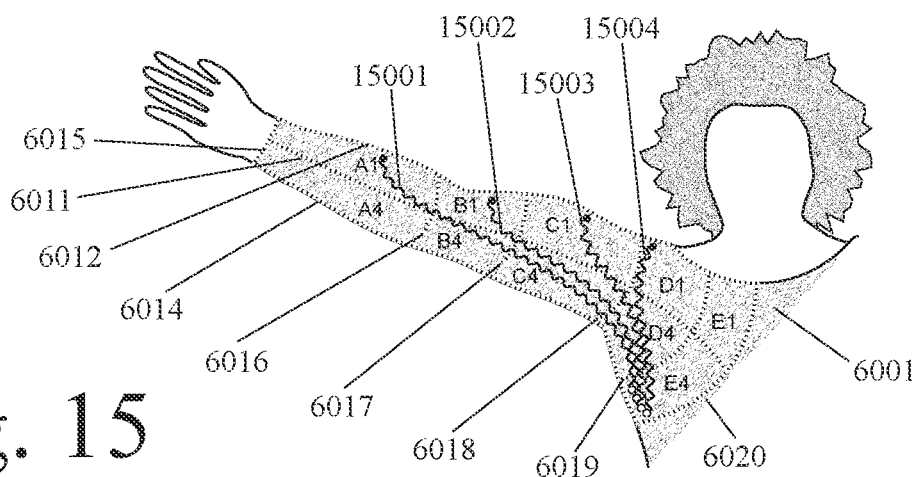
FIG. 15 shows an eighth example of smart clothing with diverging (partial loop) helical electromagnetic energy pathways on a person's arm.

FIG. 15 shows another example of how this invention can be embodied in an article of smart clothing for measuring body motion and/or configuration comprising: an article of clothing worn by a person; wherein the article of clothing further comprises an arm (or leg) associated portion which is configured to span the person's elbow (or knee), the person's shoulder (or hip), and a portion of the person's torso adjacent to the shoulder (or hip); wherein the arm (or leg) associated portion can be divided into twenty arcuate areas A1, A2, A3, A4, B1, B2, B3, B4, C1, C2, C3, C4, D1, D2, D3, D4, E1, E2, E3, and E4 (as defined elsewhere in this disclosure); wherein the arm (or leg) associated portion further comprises a first flexible arcuate energy pathway which spans from a first arcuate area selected from the group consisting of A1, A2, A3, A4, B1, B2, B3, B4, C1, C2, C3, C4, D1, D2, D3, D4, E1, E2, E3, and E4 to a second arcuate area selected from the group consisting of A1, A2, A3, A4, B1, B2, B3, B4, C1, C2, C3, C4, D1, D2, D3, D4, E1, E2, E3, and E4, wherein the second arcuate area is in a different longitudinal segment and in a different radial quadrant than the first arcuate area; wherein the arm (or leg) associated portion further comprises a second flexible arcuate energy pathway which spans from the first arcuate area to a third arcuate area selected from the group consisting of A1, A2, A3, A4, B1, B2, B3, B4, C1, C2, C3, C4, D1, D2, D3, D4, E1, E2, E3, and E4, wherein the third arcuate area is in a different longitudinal segment and in a different radial quadrant than the first arcuate area, and wherein the third arcuate area is different than the second arcuate area; and wherein changes in the flow of energy through the first flexible energy pathway and changes in the flow of energy through the second flexible energy pathway are analyzed jointly to measure changes in body motion and/or configuration.

The example in FIG. 15 is like the one in FIG. 9 except that it includes a second set of proximally-converging (distally-diverging) arcuate energy pathways. FIG. 15 shows: first flexible arcuate energy pathway 15001 which spans from arcuate area E4 to arcuate area A1; second flexible arcuate energy pathway 15002 which spans from arcuate area E4 to arcuate area B1; third flexible arcuate energy pathway 15003 which spans from arcuate area E4 to arcuate area C1; and fourth flexible arcuate energy pathway 15004 which spans from arcuate area E4 to arcuate area D1. A similar example can be created for a leg—with flexible arcuate energy pathways having the same configurations relative to the twenty arcuate areas (A1, A2, A3, A4, B1, B2, B3, B4, C1, C2, C3, C4, D1, D2, D3, D4, E1, E2, E3, and E4) defined for the leg.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

Figure 16:
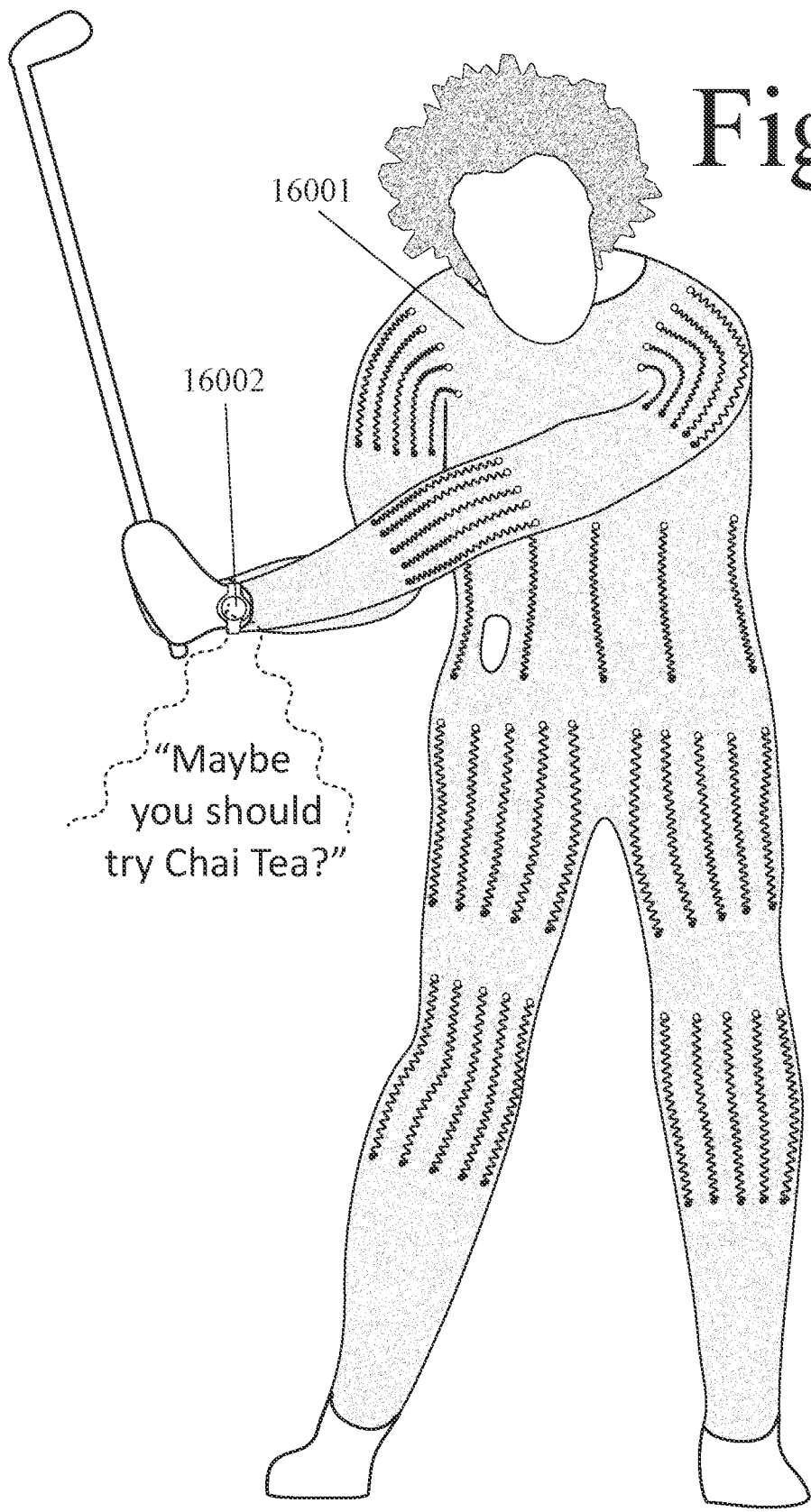
FIG. 16 shows an example of full-body smart clothing with multiple electromagnetic energy pathways spanning multiple body joints.

FIG. 16 shows an example of how this invention can perform real-time analysis of full-body motion and/or configuration and provide a person with information. In this example, wrist-worn component 16002 has a speech-based computer-to-human interface. In this example, motion recognition clothing 16001 which further comprises a plurality of flexible arcuate energy pathways have resulted in analysis of the person's full-body motion and/or configuration while the person played golf and speech-based feedback is now provided. In an example, first and second flexible energy pathways can have longitudinal axes which span a portion of a person's body. In an example, first and second flexible arcuate energy pathways can converge or diverge in a radial manner as they longitudinally span a portion of the person's body.

In an example, this invention can comprise smart clothing for measuring, modeling, and/or capturing a person's body motion and/or configuration comprising: (a) a first flexible arcuate energy pathway that is configured to span a portion of a person's body; (b) a second flexible arcuate energy pathway that is configured to span the portion of a person's body; and (c) jointly analyzing energy flows through the first flexible arcuate energy pathway and the second flexible arcuate energy pathway in order to estimate, measure, and/or model the abduction, eversion, extension, flexion, inversion, pronation, radial deviation rotation, supination, and/or ulnar deviation of the portion of the person's body. In an example, first and second flexible arcuate energy pathways can converge or diverge as they longitudinally span the portion of the person's body.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

FIG. 17 shows another example of how this invention can perform real-time analysis of full-body motion and/or configuration and provide a person with information. In this example, wrist-worn component 17002 has a speech-based computer-to-human interface. In this example, motion recognition clothing 17001 which further comprises a plurality of flexible arcuate energy pathways have resulted in analysis of the person's full-body motion and/or configuration while the person played golf and speech-based feedback is now provided. In an example, first and second flexible energy pathways can have longitudinal axes which span a portion of a person's body. In an example, first and second flexible arcuate energy pathways can converge or diverge in a radial manner as they longitudinally span a portion of the person's body.

In an example, this invention can comprise smart clothing for measuring, modeling, and/or capturing a person's body motion and/or configuration comprising: (a) a first flexible arcuate energy pathway that is configured to span a portion of a person's body; (b) a second flexible arcuate energy pathway that is configured to span the portion of a person's body; and (c) jointly analyzing energy flows through the first flexible arcuate energy pathway and the second flexible arcuate energy pathway in order to estimate, measure, and/or model the abduction, eversion, extension, flexion, inversion, pronation, radial deviation rotation, supination, and/or ulnar deviation of the portion of the person's body. In an example, first and second flexible arcuate energy pathways can converge or diverge as they longitudinally span the portion of the person's body.

In an example, a customized article of clothing for measuring changes in a person's body configuration can be created by computer-guided 3D printing electromagnetically-conductive ink onto an electromagnetically-nonconductive material. In an example, printing with electromagnetically-conductive ink can create stretchable and/or bendable electromagnetic energy pathways, wherein changes in a person's body configuration stretch and/or bend the pathways and thus change the transmission of electromagnetic energy through the pathways. In an example, changes in the flow of electromagnetic energy through the pathways can be measured by measuring one or more parameters selected from the group consisting of: amperage, capacitance, conductivity, current, electromagnetic wave pattern, impedance, phase, resistance, and voltage.

In an example, an electromagnetically-conductive ink can be made by mixing or impregnating a nonconductive (or less conductive) material with a conductive (or more conductive) material. In an example, electromagnetically-conductive ink can be created by mixing or impregnating polyurethane with aluminum, carbon, copper, gold, silver, and/or steel particles. In an example, an electronically-functional textile can be created by: printing electromagnetically-conductive ink; and placing modular electromagnetically-conductive members (such as electronic data processing components) onto clothing. Example variations and descriptions discussed elsewhere in this disclosure or in priority-linked disclosures can be applied to this example, but are not repeated here in order to reduce redundancy.

In an example, this invention can also comprise a method for measuring, modeling, and/or capturing a person's body motion and/or configuration comprising: (a) measuring a first energy flow from a first flexible energy pathway that is configured to span a portion of a person's body; (b) measuring a second energy flow from a second flexible energy pathway that is configured to span the portion of a person's body; and (c) jointly analyzing the first and second energy flows in order to estimate, measure, and/or model the abduction, eversion, extension, flexion, inversion, pronation, radial deviation rotation, supination, and/or ulnar deviation of the portion of the person's body. In an example, the first and second flexible arcuate energy pathways can converge or diverge as they longitudinally span the portion of the person's body.

In an example, first and second energy flows can be electrical energy. In an example, electrical energy can be conducted through flexible energy pathways and the amounts of electrical energy conducted can change when the configurations of the pathways change as a portion of the person's body moves. In an example, electrical voltage, current, resistance, and/or impedance can be measured. In an example, electrical energy can be generated by energy pathways when the configurations of the pathways change as the portion of the person's body moves. In an example, the energy pathways can be piezoelectric. In an example, first and second energy flows can be light energy. In an example, energy pathways can be fiber optic. In an example, the amount, wavelength, and/or spectrum of light energy transmitted through energy pathways can change when the configurations of the pathways change as the portion of a person's body moves. In an example, first and second energy flows can be sound energy. In an example, energy flows can be ultrasonic. In an example, the amount, frequency, or pattern of sound energy transmitted through energy pathways can change when the shapes of the pathways change.

In an example, joint statistical analysis of first and second energy flows through first and second flexible arcuate energy pathways can provide more accurate estimation, measurement, and/or modeling of abduction, eversion, extension, flexion, inversion, pronation, radial deviation rotation, supination, and/or ulnar deviation of a portion of a person's body than does separate statistical analysis of a first energy flow or a second energy flow. In an example, energy flows from first and second flexible arcuate energy pathways can be averaged together to reduce the variability of measurement and/or reduce the impact of measurement error in one pathway. In an example, a statistical method can be used which gives greater statistical weight to a first energy flow over a first range of abduction, eversion, extension, flexion, inversion, pronation, radial deviation rotation, supination, and/or ulnar deviation and gives greater statistical weight to a second energy flow over a second range of abduction, eversion, extension, flexion, inversion, pronation, radial deviation rotation, supination, and/or ulnar deviation. In an example, a statistical method can analyze differences between first and second energy flows to determine if the locations of the flexible energy pathways relative to the surface of a person's body have shifted and to adjust estimation if such shifting occurs.

In an example, the relationship between energy flows and the motion and/or configuration of a portion of a person's body can be nonlinear and/or stochastic. In an example, joint analysis of first and second energy flows from first and second flexible arcuate energy pathways spanning a portion of a person's body can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, first and second flexible energy pathways can have longitudinal axes which span a portion of a person's body. In an example, first and second flexible arcuate energy pathways can diverge in a radial manner as they longitudinally span a portion of the person's body. In an example, first and second flexible arcuate energy pathways can be concentric and/or nested as they span a portion of a person's body. In an example, first and second flexible arcuate energy pathways can be pathways within an energy-transmitting mesh which spans a portion of a person's body.

In an example, a wearable device for measuring the configuration or motion of a human body joint can comprise: (a) a joint-spanning spiral member which is configured to spiral around the surface of a portion of the human body which contains a human body joint; and (b) a plurality of electromagnetic energy sensors which measure electromagnetic energy from different locations on the joint-spanning spiral member, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on the dorsal surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

In various examples, one or more applications for this invention can be selected from group consisting of: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); doing the funky chicken dance; health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

I claim:
1. Smart clothing with stretch sensors for measuring changes in body configuration comprising:
   a wearable layer which is configured to be worn by a person, wherein the wearable layer comprises a first electromagnetically-nonconductive material; and
   an electromagnetically-conductive pathway, wherein a distal portion of the electromagnetically-conductive pathway is more elastic or stretchable than a proximal portion of the electromagnetically-conductive pathway, or vice versa, wherein the electromagnetically-conductive pathway is created by printing electromagnetically-conductive ink onto the wearable layer, wherein the ink comprises a mixture of a second electromagnetically-nonconductive material and an electromagnetically-conductive material, wherein stretching the electromagnetically-conductive pathway causes changes in the transmission of electromagnetic energy through the electromagnetically-conductive pathway, and wherein the changes in the transmission of electromagnetic energy through the electromagnetically- conductive pathway are analyzed to measure changes in the configuration of the person's body.

2. The smart clothing in claim 1 wherein the first electromagnetically-nonconductive material, the second electromagnetically-nonconductive material, or both comprise a polymer.

3. The smart clothing in claim 1 wherein the first electromagnetically-nonconductive material, the second electromagnetically-nonconductive material, or both comprise polyurethane.

4. The smart clothing in claim 1 wherein the first electromagnetically-nonconductive material, the second electromagnetically-nonconductive material, or both comprise elastane.

5. The smart clothing in claim 1 wherein the electromagnetically-conductive material comprises aluminum, carbon, copper, gold, silver, or steel.

6. The smart clothing in claim 1 wherein the first electromagnetically-nonconductive polymer comprises polyurethane, the second electromagnetically-nonconductive polymer comprises polyurethane, and the electromagnetically-conductive material comprises aluminum.

7. The smart clothing in claim 1 wherein the first electromagnetically-nonconductive polymer comprises polyurethane, the second electromagnetically-nonconductive polymer comprises polyurethane, and the electromagnetically-conductive material comprises carbon.

8. The smart clothing in claim 1 wherein the first electromagnetically-nonconductive polymer comprises polyurethane, the second electromagnetically-nonconductive polymer comprises polyurethane, and the electromagnetically-conductive material comprises copper.

9. The smart clothing in claim 1 wherein the first electromagnetically-nonconductive polymer comprises polyurethane, the second electromagnetically-nonconductive polymer comprises polyurethane, and the electromagnetically-conductive material comprises gold.

10. The smart clothing in claim 1 wherein the first electromagnetically-nonconductive polymer comprises polyurethane, the second electromagnetically-nonconductive polymer comprises polyurethane, and the electromagnetically-conductive material comprises silver.

11. The smart clothing in claim 1 wherein the first electromagnetically-nonconductive polymer comprises polyurethane, the second electromagnetically-nonconductive polymer comprises polyurethane, and the electromagnetically-conductive material comprises steel.

12. The smart clothing in claim 1 wherein computer-guided 3D printing is used to print electromagnetically-conductive ink on the wearable layer.

13. The smart clothing in claim 1 wherein the smart clothing further comprises a data processor or other modular electronic members to create an electronically-functional article of clothing.

14. The smart clothing in claim 1 wherein computer-guided 3D printing is used to print modular members on the wearable layer to create an electronically-functional article of clothing.

15. The smart clothing in claim 1 wherein computer-guided 3D printing is used to place modular members on the wearable layer to create an electronically-functional article of clothing.

16. The smart clothing in claim 1 wherein computer-guided 3D printing is used to adhere modular members on the wearable layer to create an electronically-functional article of clothing.

17. The smart clothing in claim 1 wherein the electromagnetic energy pathway is helical.

18. The smart clothing in claim 1 wherein the changes in the transmission of electromagnetic energy through the pathway are measured by one or more parameters selected from the group consisting of: amperage, capacitance, conductivity, current, electromagnetic wave pattern, impedance, phase, resistance, and voltage.

19. The smart clothing in claim 1 wherein the smart clothing further comprises a first flexible energy pathway and a second flexible energy pathway; wherein the first energy pathway and the second energy pathway differ in elasticity level.

20. The smart clothing in claim 1 wherein the smart clothing further comprises a first flexible energy pathway and a second flexible energy pathway; wherein the first energy pathway and the second energy pathway have different cross-sectional shapes.

\* \* \* \* \*